US009365529B2

(12) United States Patent
Clary et al.

(10) Patent No.: US 9,365,529 B2
(45) Date of Patent: *Jun. 14, 2016

(54) BENZENESULFONAMIDE COMPOUNDS, METHOD FOR SYNTHESIZING SAME, AND USE THEREOF IN MEDICINE AS WELL AS IN COSMETICS

(71) Applicant: GALDERMA RESEARCH & DEVELOPMENT, Biot (FR)

(72) Inventors: Laurence Clary, La Colle sur Loup (FR); Sandrine Chambon, Le Cannet (FR); Laurent Chantalat, Grasse (FR); Carine Rosignoli, Mougins le Haut (FR); Olivier Roye, Fayence (FR); Jean-Claude Pascal, Nice (FR); Marlene Schuppli-Nollet, Le Rouret (FR)

(73) Assignee: GALDERMA RESEARCH & DEVLOPMENT, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/626,302

(22) Filed: Feb. 19, 2015

(65) Prior Publication Data

US 2015/0158834 A1  Jun. 11, 2015

Related U.S. Application Data

(60) Division of application No. 14/103,470, filed on Dec. 11, 2013, now Pat. No. 8,980,897, which is a continuation of application No. 13/774,023, filed on Feb. 22, 2013, now Pat. No. 8,633,196, which is a continuation of application No. 13/381,234, filed as application No. PCT/FR2010/051331 on Jun. 28, 2010, now Pat. No. 8,420,632.

(30) Foreign Application Priority Data

Jun. 30, 2009  (FR) ...................... 09 54460

(51) Int. Cl.
| | | |
|---|---|---|
| *C07D 295/26* | (2006.01) | |
| *C07D 471/04* | (2006.01) | |
| *C07D 209/26* | (2006.01) | |
| *C07D 261/20* | (2006.01) | |
| *C07D 215/14* | (2006.01) | |
| *C07D 213/68* | (2006.01) | |
| *A61K 31/497* | (2006.01) | |
| *A61K 31/551* | (2006.01) | |
| *A61K 31/4965* | (2006.01) | |
| *C07D 209/10* | (2006.01) | |
| *C07D 213/30* | (2006.01) | |
| *C07D 209/24* | (2006.01) | |
| *C07D 213/55* | (2006.01) | |
| *C07D 295/15* | (2006.01) | |
| *C07D 209/20* | (2006.01) | |
| *C07D 213/56* | (2006.01) | |

(52) U.S. Cl.
CPC ............ *C07D 295/26* (2013.01); *A61K 31/497* (2013.01); *A61K 31/4965* (2013.01); *A61K 31/551* (2013.01); *C07D 209/10* (2013.01); *C07D 209/20* (2013.01); *C07D 209/24* (2013.01); *C07D 209/26* (2013.01); *C07D 213/30* (2013.01); *C07D 213/55* (2013.01); *C07D 213/56* (2013.01); *C07D 213/68* (2013.01); *C07D 215/14* (2013.01); *C07D 261/20* (2013.01); *C07D 295/15* (2013.01); *C07D 471/04* (2013.01)

(58) Field of Classification Search
USPC ............. 514/253.06, 252.12, 253.01, 254.09, 514/254.04, 253.04, 255.02, 218; 544/363, 544/400, 360, 373, 368, 362, 383, 361
See application file for complete search history.

(56) References Cited

U.S. PATENT DOCUMENTS

| | | |
|---|---|---|
| 6,326,516 B1 | 12/2001 | Levin et al. |
| 7,511,144 B2 | 3/2009 | Shimano et al. |
| 8,420,632 B2 | 4/2013 | Clary et al. |
| 8,633,196 B2 | 1/2014 | Clary et al. |
| 8,980,897 B2 * | 3/2015 | Clary ................... C07D 209/10 514/252.12 |
| 2003/0130238 A1 | 7/2003 | Sandanayaka et al. |
| 2006/0079515 A1 | 4/2006 | Frost |
| 2008/0085893 A1 | 4/2008 | Yang et al. |
| 2012/0323006 A1 | 12/2012 | Clary et al. |

FOREIGN PATENT DOCUMENTS

| | | |
|---|---|---|
| CN | 1337944 | 2/2002 |
| EA | 002810 B1 | 10/2002 |
| EA | 004736 B1 | 8/2004 |
| JP | 2001-502326 A | 2/2001 |
| JP | 2002-503717 A | 2/2002 |
| RU | 2232751 C2 | 7/2004 |

(Continued)

OTHER PUBLICATIONS

Written Opinion of the international Searching Authority (Form PCT/ISA/237) issued in PCTIFR2010/051331 on Jan. 17, 2012, and an English language translation of the Written Opinion.

(Continued)

*Primary Examiner* — Kristin Vajda
(74) *Attorney, Agent, or Firm* — Dentons US LLP

(57) ABSTRACT

Benzenesulfonamide compounds having a structure of formula (I) are described. Also described, are methods for synthesizing the compounds and to the use thereof in pharmaceutical compositions for human or veterinary medicine and in cosmetic compositions.

17 Claims, No Drawings

(56) References Cited

FOREIGN PATENT DOCUMENTS

| WO | 9816506 A1 | 4/1998 |
|---|---|---|
| WO | 98/32748 A1 | 7/1998 |
| WO | 9942436 A1 | 8/1999 |
| WO | 00/37436 A1 | 6/2000 |
| WO | 00/44709 A2 | 8/2000 |
| WO | 00/44711 | 8/2000 |
| WO | 03022801 A1 | 3/2003 |
| WO | 2006042100 A2 | 4/2006 |
| WO | 2008/045671 A1 | 4/2008 |

OTHER PUBLICATIONS

Lohmander, et al., "The Structure of Aggrecan Fragments in Human Synovial Fluid," Arthritis & Rheumatism, Sep. 1993, pp. 1214-1222, vol. 36, No. 9, American College of Rheumatoiogy, US.

Schlondorff, et al., "Intracellular maturation and localization of the tumor necrosis factor a convertase (TACE)," Biochem. J., 2000, pp. 131-138, vol. 347, Biochemical Society, UK.

Black, et al., "A metalloproteinase disintegrin that releases tumour-necrosis factor-a from cells," Nature, Feb. 20, 1997, pp. 729-733, vol. 385, Nature Publishing Group, UK.

Tamura, et al., "Highly Selective and Orally Active Inhibitors of Type IV Collagenase (MNP-9 and MMP-2): N-Sulfonylamino Acid Derivatives," J. Med. Chem., 1998, pp. 840-849, vol. 41, American Chemical Society, US.

Moss et al., "Cloning of a disintegrin metalloproteinase that processes precursor tumour-necrosis factor-a," Nature, Feb. 20, 1997, pp. 733-736, vol. 385, Nature Publishing Group, UK.

MacPherson, et al., "Discovery of CGS 27023A, a Non-Peptidic, Potent, and Orally Active Stromelysin Inhibitor That Blocks Cartilage Degradation in Rabbits," J. Chem., 1997, pp. 2525-2532, vol. 40, American Chemical Society, US.

Kupper, "Immunologic Targets in Psoriasis," The New England Journal of Medicine, Nov. 20, 2003, pp. 1987-1990, vol. 349, Issue 21, Massachusetts Medical Society, US.

Bonifati, et al., "Correlated increases of tumor necrosis factor-a, interleukin-6 and granulocyte monoryte-colony stimulating factor levels in suction blister fluids and sera of psoriatic patients-relationships with disease severity," Chemical and Experimental Dermatology, 1994, pp. 383-387, vol. 19, Wiley-Blackwell, UK.

MacDonald, et al., "Tumour necrosis factor-alpha and interferon-gamma production measured at the single cell level in normal and inflamed human intestine," Clin. exp. Immunol., 1990, pp. 301-305, vol. 81, Blackwell Publishing, UK.

Elliot, et al., "Randomised double-blind comparison of chimeric monoclonal antibody to tumour necrosis factor a (cA2) versus placebo in rheumatoid arthritis," The Lancet, Oct. 22, 1994, pp. 1105-1110, vol. 344, Elservier, UK.

International Search Report (PCT/ISA/210) issued on Oct. 28, 2010, by the French Patent Office as the International Searching Authority for International Patent Application No. PCTIFR2010/051331.

Cancer [online], [retrieved on Jul. 8, 2007] Retrieved from the Internet. URL: http://www.nlm.nih.gov/medlineplus/cancer.html.

Lala, et al., "Role of nitric oxide in tumor progression: Lessons from experimental tumors," Cancer and Metastasis Reviews (1998), 17, 91-106.

Golub, et al., "Molecular Classification of Cancer: Class Discovery and Class Prediction by Gene Expression Monitoring," Science (1999), vol. 286, 531-537.

* cited by examiner

BENZENESULFONAMIDE COMPOUNDS, METHOD FOR SYNTHESIZING SAME, AND USE THEREOF IN MEDICINE AS WELL AS IN COSMETICS

PRIOR APPLICATIONS

This application is a Divisional of U.S. patent application Ser. No. 14/103,470, filed Dec. 11, 2013, now allowed, which is a Continuation of U.S. patent application Ser. No. 13/774, 023, filed Feb. 22, 2013, now U.S. Pat. No. 8,633,196, which is a Continuation of U.S. patent application Ser. No. 13/381, 234, filed Aug. 27, 2012, now U.S. Pat. No. 8,420,632 B2, which is the United States national phase of PCT/FR2010/ 051331, filed Jun. 28, 2010, which claims foreign priority under 35 U.S.C. §119 of FR 09/54460, filed Jun. 30, 2009, each hereby expressly incorporated by reference in its entirety.

TECHNICAL FIELD

The present invention relates to novel benzenesulfonamide compounds corresponding to general formula (I) below:

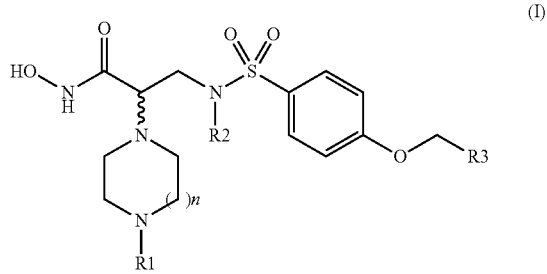

and also to the process for synthesizing same and to the use thereof in pharmaceutical compositions intended for use in human or veterinary medicine.

The compounds of the present invention act as inhibitors of TNFα-converting enzyme, also known as TACE. They are consequently of use in the treatment of diseases for which reducing TNFα production is of great interest.

The present invention also relates to the use of the compounds corresponding to general formula (I) in cosmetic compositions.

PRIOR ART

Adamalysins ("ADAM" or A Disintegrin and Metalloproteinase) are a subfamily of zinc metalloendopeptidase enzymes. Their ectodomain comprises a protease domain, the activation of which is zinc-dependent, a disintegrin domain and a cysteine-rich domain. To date, at least 30 different ADAMs have been identified, of which the first characterized was ADAM17, also known as TACE (TNFα-converting enzyme) [Gueydan C et al. Med. Sci 1997, 13, 83-88; Black R. A et al. Nature 1997, 385:729-733; Moss et al. Nature 1997, 385:733-736]. The TACE mRNA is present in many tissues and more particularly in monocytes, macrophages and T lymphocytes, but also in keratinocytes for example. TACE is responsible for the cleavage of pro-TNFα, a 26 kDa membrane protein, so as to result in the release of biologically active soluble TNFα, a 17 kDa protein [Schlondorff et al. Biochem. J. 2000, 347, 131-138]. The soluble TNFα released by the cell is capable of acting on sites very remote from the site of synthesis.

TNFα is involved in a large number of pro-inflammatory biological processes [Aggarwal et al, Eur. Cytokine Netw., 1996, 7: 93-124]. Several pharmacological and clinical studies have shown in an obvious manner that blocking the effects of TNFα with specific anti-TNFα antibodies or anti-TNFα biologicals (Etanercept, Adalimumab, Infliximab) is beneficial in the treatment of autoimmune diseases such as rheumatoid arthritis [Feldman et al. Lancet, 1994, 344, 1105], non-insulin-dependent diabetes mellitus [Lohmander L. S et al. Arthritis Rheum, 1993, 36, 1214-1222], or Crohn's disease [MacDonald et al. Clin. Exp. Immunol. 1990, 81, 301].

TNFα also plays a fundamental role during the inflammatory phenomenon triggered in psoriasis lesions. Serum TNFα levels are elevated in psoriatic patients [Mussi A et al. J. Biol. Regul. Homeost Agents, 1997, 11, 115-118]; TNFα levels are also elevated in the actual psoriasis plaques [Bonifati C. et al. Clin. Exp. Dermatol., 1994, 19, 383-387]. The key cells in the physiopathology of psoriasis are keratinocytes, dendritic cells and certain T lymphocytes. The interaction between these families of cells results in an inflammatory cascade that leads to the characteristic psoriasis lesions with release of TNFα [Kupper T S, N. Engl. J. Med, 2003, 349, 1987-1990]. Clinical studies for the treatment of moderate to severe plaque psoriasis with anti-TNFα biologicals (Etanercept, Adalimumab, Infliximab) have demonstrated their efficacy both on psoriasis lesions and on the quality of life of the patients [Ortonne J P, Annales de dermatologie et de venereologie {Annals of dermatology and venereology], 2005, 132 (8-9 pt2), 4S6-9 and 2005, 132, 9S01-9S70].

Thus, compounds which inhibit TNFα production are of great interest for the treatment of inflammatory diseases and diseases involving TNFα release.

SUMMARY OF THE INVENTION

Our invention therefore describes novel molecules which inhibit the TACE enzyme (TNFα-converting enzyme) and, as a result, inhibit the secretion of soluble TNFα (active form of TNFα) by cells. These novel molecules are therefore potential active ingredients for the treatment of pathological conditions which involves a decrease or an inhibition of TNFα production.

By way of illustration, and in a nonlimiting manner, these pathological conditions are, for example, septic shock, hemodynamic shock, malaria, inflammatory bowel diseases (IBDs) such as Crohn's disease and ulcerative colitis, inflammatory bone diseases, mycobacterial infections, meningitis, fibrotic diseases, cardiac diseases, ischemic attack, transplant rejection, cancer, atherosclerosis, obesity, diseases involving angiogenesis phenomena, autoimmune diseases, osteoarthritis, rheumatoid arthritis, ankylosing spondylitis, juvenile chronic arthritis, multiple sclerosis, HIV, non-insulin-dependent diabetes mellitus, allergic diseases, asthma, chronic obstructive pulmonary disease (COPD), occular inflammation, inflammatory skin diseases, psoriasis, atopic dermatitis and psoriatic arthritis.

These molecules are also potential active ingredients for the treatment of neurological pathological conditions that are inflammatory in nature, for which reducing TNFα production would be of great interest. These pathological conditions listed hereinafter in a nonlimiting manner are, for example, Alzheimer's disease, Parkinson's disease, parkinsonian disorders, amyotrophic lateral sclerosis, autoimmune diseases of the nervous system, autonomic diseases of the nervous system, dorsal pain, cerebral edema, cerebrovascular disorders, dementia, nervous system nerve fiber demyelinating autoimmune diseases, diabetic neuropathies, encephalitis, encephalomyelitis, epilepsy, chronic fatigue syndrome, giant cell arteritis, Guillain-Barré syndrome, headaches, multiple sclerosis, neuralgia, peripheral nervous system diseases, polyneuropathies, polyradiculoneuropathy, radiculopathy, respiratory paralysis, spinal cord diseases, Tourette's syndrome, central nervous system vasculitis, Huntington's disease and stroke. A large variety of TACE inhibitors is already known as indicated below. However, a large number of these inhibitors do not act selectively on the TACE enzyme compared with other enzymes of the family of ADAMs and/or of matrix metalloproteinases (MMPs).

As it happens, the nonselective inhibition of these enzyme families induces adverse side effects observed in vivo. For example, the inhibition of MMP-1 (collagenase-1) has been associated with musculoskeletal toxicity problems.

As a nonselective inhibitor, mention may also be made of Apratastat, a known inhibitor tested clinically in phase 2 for the treatment of rheumatoid arthritis (Curr Opin Investig Drugs. 2006 November; 7(11), 1014-1019). This inhibitor is not selective for the TACE enzyme compared with certain MMPs (WO 00/44709; page 251, table 10, example 61).

Other TACE inhibitors which are also known and are part of the same family as Apratastat, namely that of cyclic benzenesulfonamide derivatives, have been described in WO 00/44709 and WO 97/18194. Other patents (WO 96/00214, WO 97/22587) claim MMP and/or TACE inhibitors for which the benzenesulfonamide part is separated from the hydroxamic acid function by a single carbon atom. Publications describing MMP inhibitors of this type more broadly are also the publication by MacPherson et al. J. Med. Chem. 1997, 40, 2525 and the publication by Tamura et al. J. Med. Chem. 1998, 41, 640. Other examples of MMP/TACE inhibitors for which the sulfonamide function is separated from the hydroxamic acid by a series of two carbon atoms forming a ring are described in patents WO 98/16503, WO 98/16506, WO 98/16514 and WO 98/16520. Other examples of MMP inhibitors for which the sulfonamide function is separated from the hydroxamic acid by a series of two carbon atoms are also described in WO 2008/045671.

As it happens, the applicant has now discovered, unexpectedly and surprisingly, that novel compounds of general formula (I) exhibit a very good TACE-inhibiting activity, and in particular inhibit the TACE enzyme selectively compared with other ADAMs and MMPs.

Thus, the present invention relates to compounds of general formula (I) below:

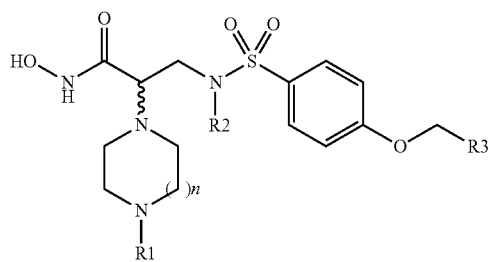

(I)

in which:
R$_1$ represents a hydrogen, an alkyl radical, a substituted alkyl radical, an alkenyl radical, a substituted alkenyl radical, an alkynyl radical, a substituted alkynyl radical, an aralkyl radical, a substituted aralkyl radical, a heteroaralkyl radical, a substituted heteroaralkyl radical, a —C(O)—R$_4$ radical, an —SO$_2$—R$_4$ radical, or a C(O)OR$_4$ radical, R$_4$ having the meanings given hereinafter;

R$_2$ is a hydrogen atom or a lower alkyl radical;

R$_3$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, a substituted aralkyl radical, a heterocyclic radical, a substituted heterocyclic radical, a cycloalkyl radical, a substituted cycloalkyl radical, a heteroaryl radical, a substituted heteroaryl radical, a heteroaralkyl radical or a substituted heteroaralkyl radical;

R$_4$ is an alkyl radical, a substituted alkyl radical, an alkenyl radical, a substituted alkenyl radical, an alkynyl radical, a substituted alkynyl radical, an aryl radical, a substituted aryl radical, an aralkyl radical or a substituted aralkyl radical;

n can take the values of 0, 1, 2 or 3;

and also the addition salts of the compounds of general formula (I) with a pharmaceutically acceptable acid, the addition salts of the compounds of general formula (I) with a pharmaceutically acceptable base, and the enantiomers of the compounds of general formula (I).

Among the addition salts of the compounds of general formula (I) with a pharmaceutically acceptable acid, mention may preferably be made of the salts with an organic acid or with an inorganic acid.

The suitable inorganic acids are, for example, hydrohalic acids such as hydrochloric acid or hydrobromic acid, sulfuric acid, nitric acid and phosphoric acid.

The suitable organic acids are, for example, acetic acid, trifluoroacetic acid, trichloroacetic acid, propionic acid, glycolic acid, pyruvic acid, succinic acid, benzoic acid, cinnamic acid, mandelic acid, methanesulfonic acid, para-toluenesulfonic acid, salicylic acid, picric acid, citric acid, oxalic acid, tartaric acid, malonic acid, maleic acid, camphorsulfonic acid and fumaric acid.

Among the addition salts of the compounds of general formula (I) with a pharmaceutically acceptable base, mention may preferably be made of the salts with an organic base or with an inorganic base.

The inorganic bases are, for example, potassium hydroxide, sodium hydroxide, lithium hydroxide or calcium hydroxide.

The suitable organic bases comprise amines and amino acids. Among the amines, mention may, for example, be made of aliphatic or aromatic, primary, secondary or tertiary amines, such as methylamine, ethylamine, ethanolamine, propylamine, isopropylamine, the 4 isomers of butylamine, dimethylamine, diethylamine, diethanolamine, dipropylamine, diisopropylamine, di-n-butylamine, pyrrolidine, piperidine, morpholine, diethanolphenylamine, trimethylamine, triethylamine, tripropylamine, quinuclidine, pyridine, quinoline or isoquinoline.

Among the amino acids, mention may, for example, be made of lysine, arginine and ornithine.

According to the present invention, the term "lower alkyl radical" denotes a linear or branched, saturated hydrocarbon-based chain containing from 1 to 4 carbon atoms.

According to the present invention, the term "alkyl radical" denotes a linear or branched, saturated hydrocarbon-based chain containing from 1 to 10 carbon atoms.

According to the present invention, the term "alkenyl radical" denotes a linear or branched, unsaturated hydrocarbon-based chain containing from 2 to 10 carbon atoms and comprising one or more double bonds.

According to the present invention, the term "alkynyl radical" denotes a linear or branched, unsaturated hydrocarbon-based chain containing from 2 to 10 carbon atoms and comprising one or more triple bonds.

According to the present invention, the term "substituted alkyl radical" denotes a linear or branched, saturated hydrocarbon-based chain containing from 1 to 10 carbon atoms and substituted with one or more radicals chosen from a halogen atom, an alkoxy radical and a hydroxyl radical.

According to the present invention, the term "substituted alkenyl radical" denotes a linear or branched, unsaturated hydrocarbon-based chain containing from 2 to 10 carbon atoms, comprising one or more double bonds and substituted with one or more radicals chosen from a halogen atom, an alkoxy radical and a hydroxyl radical.

According to the present invention, the term "substituted alkynyl radical" denotes a linear or branched, unsaturated hydrocarbon-based chain containing from 2 to 10 carbon atoms, comprising one or more triple bonds and substituted with one or more radicals chosen from a halogen atom, an alkoxy radical and a hydroxyl radical.

According to the present invention, the term "cycloalkyl" denotes a cyclic saturated hydrocarbon-based chain containing from 3 to 7 carbon atoms.

According to the present invention, the term "substituted cycloalkyl" denotes a cyclic saturated hydrocarbon-based chain containing from 3 to 7 carbon atoms and substituted with one or more radicals chosen from a halogen atom, an alkoxy radical and a hydroxyl radical.

According to the present invention, the term "aryl radical" denotes an aromatic hydrocarbon-based ring or two fused aromatic hydrocarbon-based rings.

The preferred aryl radicals are chosen from phenyl and naphthyl radicals.

According to the present invention, the term "substituted aryl radical" denotes an aromatic hydrocarbon-based ring or two fused aromatic hydrocarbon-based rings which is (are) substituted with one or more groups of atoms chosen from an alkyl, an alkoxy, an aryl, a halogen, a hydroxyl, a cyano, a trifluoromethyl and a nitro.

According to the present invention, the term "aralkyl radical" denotes an alkyl substituted with an aryl.

According to the present invention, the term "substituted aralkyl radical" denotes an alkyl substituted with a substituted aryl.

According to the present invention, the term "heterocyclic radical" denotes a saturated or unsaturated, cyclic or polycyclic hydrocarbon-based chain comprising one or more heteroatoms chosen from O, S and N.

According to the present invention, the term "substituted heterocyclic radical" denotes a heterocyclic radical substituted with one or more groups of atoms chosen from an alkyl, an alkoxy, a halogen, a hydroxyl, a cyano, a trifluoromethyl and a nitro.

According to the present invention, the term "heteroaryl radical" denotes an aromatic heterocyclic radical, i.e. a cyclic or polycyclic aromatic hydrocarbon-based chain, comprising one or more heteroatoms chosen from O, S and N.

According to the present invention, the term "substituted heteroaryl radical" denotes a heteroaryl radical substituted with one or more groups of atoms chosen, for example, from an alkyl, an alkoxy, an aryl, a substituted aryl, a halogen, a hydroxyl, a cyano, a trifluoromethyl and a nitro.

According to the present invention, the term "heteroaralkyl radical" denotes an alkyl radical substituted with a heteroaryl radical.

According to the present invention, the term "substituted heteroaralkyl radical" denotes a heteroaralkyl radical substituted with one or more groups of atoms chosen from an alkyl, an alkoxy, a halogen, a hydroxyl, a cyano, a trifluoromethyl and a nitro.

According to the present invention, the term "alkoxy radical" denotes an oxygen atom substituted with an alkyl radical.

According to the present invention, the term "halogen atom" denotes a fluorine, chlorine, bromine or iodine atom.

Among the compounds of general formula (I) which fall within the context of the present invention, mention may in particular be made of the following compounds:

1) 3-[(4-but-2-ynyloxybenzenesulfonyl)methylamino]-N-hydroxy-2-(4-methanesulfonylpiperazin-1-yl)propionamide
2) (S)-3-(4-but-2-ynyloxybenzenesulfonylamino)-N-hydroxy-2-(4-methanesulfonylpiperazin-1-yl)propionamide
3) (S)-3-(4-benzyloxybenzenesulfonylamino)-N-hydroxy-2-(4-methanesulfonylpiperazin-1-yl)propionamide
4) (S)-3-[(4-benzyloxybenzenesulfonyl)methylamino]-N-hydroxy-2-(4-methanesulfonylpiperazin-1-yl)propionamide
5) (S)-N-hydroxy-2-(4-methanesulfonylpiperazin-1-yl)-3-[4-(2-methylquinolin-4-ylmethoxy)benzenesulfonylamino]propionamide
6) (S)-N-hydroxy-2-(4-methanesulfonylpiperazin-1-yl)-3-[4-(naphthalen-1-ylmethoxy)benzenesulfonylamino]propionamide
7) (S)-N-hydroxy-2-(4-methanesulfonylpiperazin-1-yl)-3-(4-propoxybenzenesulfonylamino)propionamide
8) (S)-3-[4-(3-cyanobenzyloxy)benzenesulfonylamino]-N-hydroxy-2-(4-methanesulfonylpiperazin-1-yl)propionamide
9) (S)-3-[4-(4-cyanobenzyloxy)benzenesulfonylamino]-N-hydroxy-2-(4-methanesulfonylpiperazin-1-yl)propionamide
10) benzyl 4-{(S)-1-hydroxycarbamoyl-2-[4-(2-methylquinolin-4-ylmethoxy)benzenesulfonylamino]ethyl}piperazine-1-carboxylate
11) (S)-N-hydroxy-2-(4-methanesulfonylpiperazin-1-yl)-3-[4-(2-phenylpyridin-4-ylmethoxy)benzenesulfonylamino]propionamide
12) (R)-N-hydroxy-2-(4-methanesulfonylpiperazin-1-yl)-3-[4-(2-methylquinolin-4-ylmethoxy)benzenesulfonylamino]propionamide
13) (S)-N-hydroxy-3-[4-(2-methylquinolin-4-ylmethoxy)benzenesulfonylamino]-2-piperazin-1-yl-propionamide
14) (S)-N-hydroxy-2-(4-methanesulfonylpiperazin-1-yl)-3-[4-(2-methylquinolin-4-ylmethoxy)benzenesulfonylamino]propionamide hydrochloride
15) tert-butyl 3-{4-[(S)-2-hydroxycarbamoyl-2-(4-methanesulfonylpiperazin-1-yl)ethylsulfamoyl]phenoxymethyl}-2-methylindole-1-carboxylate di(trifluoroacetate)
16) (S)-N-hydroxy-2-(4-methanesulfonylpiperazin-1-yl)-3-[4-(quinolin-4-ylmethoxy)benzenesulfonylamino]propionamide
17) (S)-2-(4-benzylpiperazin-1-yl)-N-hydroxy-3-[4-(2-methylquinolin-4-ylmethoxy)benzenesulfonylamino]propionamide
18) (S)-2-[4-(4-fluorobenzyl)piperazin-1-yl]-N-hydroxy-3-[4-(2-methylquinolin-4-ylmethoxy)benzenesulfonylamino]propionamide
19) (S)-2-(4-ethylpiperazin-1-yl)-N-hydroxy-3-[4-(2-methylquinolin-4-ylmethoxy)benzenesulfonylamino]propionamide 20) (S)-N-hydroxy-3-[4-(2-methylquinolin-4-ylmethoxy) benzenesulfonylamino]-2-[4-(4-trifluoromethyl-benzyl) piperazin-1-yl]propionamide
21) (S)-N-hydroxy-2-[4-(4-methylbenzyl)piperazin-1-yl]-3-[4-(2-methylquinolin-4-ylmethoxy)benzenesulfonylamino]propionamide
22) (S)-3-[4-(benzoisoxazol-3-ylmethoxy)benzenesulfonylamino]-N-hydroxy-2-(4-methanesulfonylpiperazin-1-yl) propionamide
23) (S)-N-hydroxy-2-(4-isobutyrylpiperazin-1-yl)-3-[4-(2-methylquinolin-4-ylmethoxy)benzenesulfonylamino]propionamide
24) (S)-N-hydroxy-2-[4-(2-methylpropane-1-sulfonyl)piperazin-1-I]-3-[4-(2-methylquinolin-4-ylmethoxy)benzenesulfonylamino]propionamide
25) (S)-N-hydroxy-2-(4-methanesulfonylpiperazin-1-yl)-3-[4-(2-trifluoromethylpyrazolo[1,5-α]pyridin-3-ylmethoxy)benzenesulfonylamino]propionamide
26) (S)-N-hydroxy-3-[4-(2-methylquinolin-4-ylmethoxy) benzenesulfonylamino]-2-[4-(propane-2-sulfonyl)piperazin-1-yl]propionamide
27) (S)-2-(4-benzylpiperazin-1-yl)-N-hydroxy-3-[4-(2-trifluoromethylpyrazolo[1,5-α]pyridin-3-ylmethoxy)benzenesulfonylamino]propionamide
28) (S)-2-(4-acetylpiperazin-1-yl)-N-hydroxy-3-[4-(2-methylquinolin-4-ylmethoxy)benzenesulfonylamino]propionamide
29) (S)-N-hydroxy-2-(4-methanesulfonylpiperazin-1-yl)-3-{propyl-[4-(quinolin-4-ylmethoxy)benzenesulfonyl]amino}propionamide
30) (S)-2-(4-benzenesulfonylpiperazin-1-yl)-N-hydroxy-3-[4-(pyrazolo[1,5-α]pyridin-3-ylmethoxy)benzenesulfonylamino]propionamide
31) (S)-2-(4-benzylpiperazin-1-yl)-N-hydroxy-3-[4-(1-methylpiperidin-4-ylmethoxy)benzenesulfonylamino]propionamide
32) (S)-2-[4-(4-fluorobenzoyl)piperazin-1-yl]-N-hydroxy-3-[4-(3-m-tolyl-propoxy)benzenesulfonylamino]propionamide
33) (S)-N-hydroxy-3-[4-(2-methylnaphthalen-1-ylmethoxy) benzenesulfonylamino]-2-(4-propionylpiperazin-1-yl) propionamide
34) (S)-N-hydroxy-3-[4-(4-methylpentyloxy)benzenesulfonylamino]-2-(4-phenylacetylpiperazin-1-yl)propionamide
35) (S)-N-hydroxy-2-(4-methanesulfonylpiperazin-1-yl)-3-[4-(2-methylpyridin-4-ylmethoxy)benzenesulfonylamino]propionamide
36) (S)-2-(3-acetylimidazolidin-1-yl)-N-hydroxy-3-[4-(2-methylquinolin-4-ylmethoxy)benzenesulfonylamino]propionamide
37) (S)-3-[4-(3,5-dimethylbenzyloxy)benzenesulfonylamino]-N-hydroxy-2-imidazolidin-1-ylpropionamide
38) (S)- N-hydroxy-2-(4-methanesulfonyl-[1,4]diazepan-1-yl)-3-[4-(2-methylquinolin-4-ylmethoxy)benzenesulfonylamino]propionamide
39) (S)-2-(4-benzyl-[1,4]diazepan-1-yl)-N-hydroxy-3-[4-(2-methylquinolin-4-ylmethoxy)benzenesulfonylamino]propionamide
40) (S)-2-[1,4]diazocan-1-yl-N-hydroxy-3-[4-(2-methylquinolin-4-ylmethoxy)benzenesulfonylamino]propionamide.
41) (S)-N-hydroxy-3-[4-(2-methylbenzofuran-3-ylmethoxy) benzenesulfonylamino]-2-[4-(propane-2-sulfonyl)piperazin-1-yl]propionamide
42) (S)-2-(4-benzylpiperazin-1-yl)-N-hydroxy-3-[4-(2-isopropyl-1H-indol-3-ylmethoxy)benzenesulfonylamino] propionamide The compounds of general formula (I) are prepared according to the reaction scheme (Scheme 1) presented below.

Scheme 1

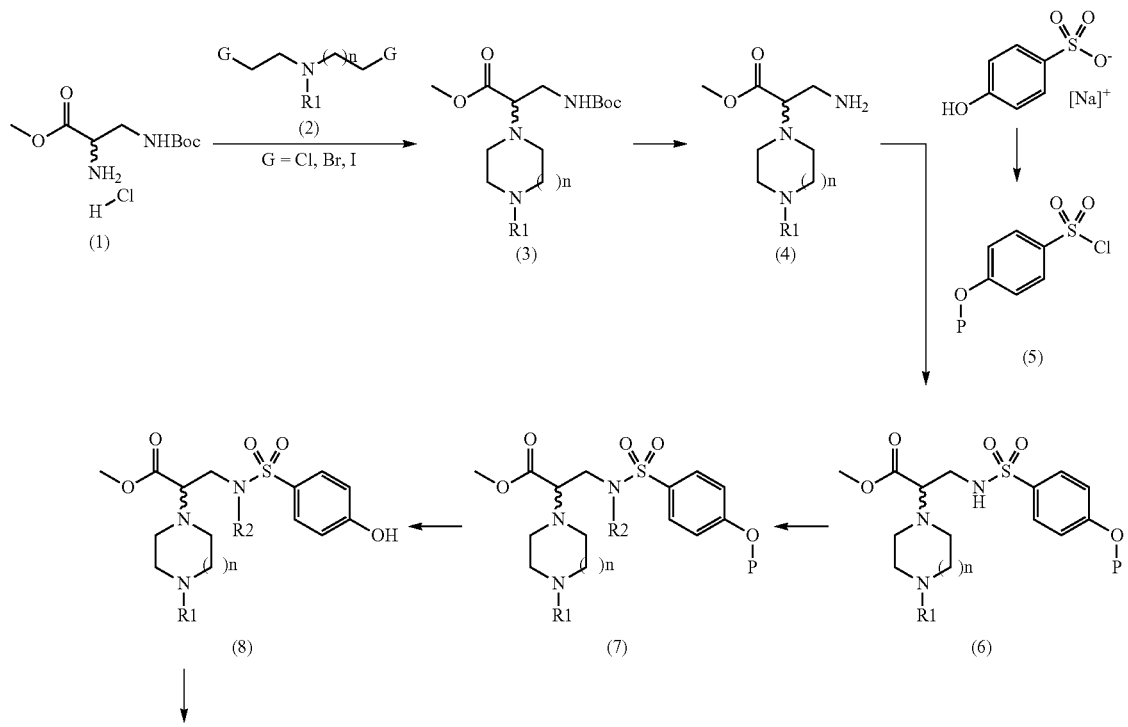

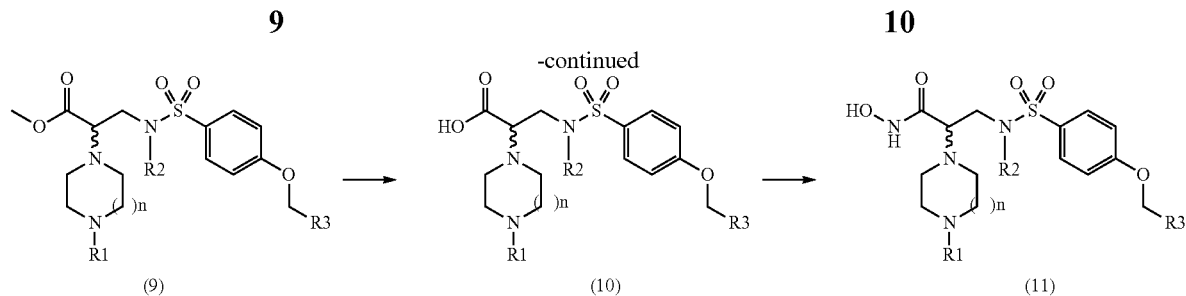

(9) → (10) → (11)

According to Scheme 1, the compounds (3) are obtained by reaction between the amino acid (1) H-DAP(Boc)-OMe.HCl or H-(D)-DAP(Boc)-OMe.HCl and the compound (2) (commercial or prepared beforehand) in the presence of an organic tertiary base such as diisopropylethylamine or triethylamine at a temperature of between 60° C. and 120° C. The compounds (4) are obtained by deprotection of the amine function of compounds (3) according to conventional methods such as, for example, the use of a solution of hydrochloric acid in isopropanol.

A reaction between the compound (4) and 4-hydroxybenzenesulfonyl chloride O-protected with a benzyl group for example (P=CH$_2$-Ph) (5) in the presence of a tertiary amine such as, for example, triethylamine in dichloromethane, produces the compound (6). An N-alkylation of the sulfonamide function can then be carried out by reaction with an alkyl halide in the presence of a base such as, for example, potassium carbonate in a solvent such as DMF, so as to give the derivative (7). The compound (8) is obtained by deprotection according to methods known by those skilled in the art for deprotecting a phenol function. The compound (9) is obtained by alkylation of the phenol function of the compound (8) by reaction with an alkyl halide in the presence of a base such as, for example, cesium carbonate in acetone, or via a Mitsunobu reaction with a primary alcohol derivative in the presence of triphenylphosphine and of diisopropyl azodicarboxylate for example. The compound (10) is obtained via a saponification reaction in the presence of a base such as lithium hydroxide in the presence of water and of tetrahydrofuran for example. In a final step, the compound (11) is obtained by coupling between O-(tert-butyldimethylsilyl)hydroxylamine for example and the derivative (10) under conventional peptide coupling conditions, using, for example, 1-(3-dimethylaminopropyl)-3-ethylcarbodiimide hydrochloride, hydroxybenzotriazole or TBTU as coupling agents, and triethylamine or diisopropylethylamine as base, in a solvent such as dichloromethane or dimethylformamide. The deprotection of the silylated hydroxamic acid intermediately formed is carried out in situ or by washing with a slightly acidic aqueous solution, so as to give the compound (11).

Another alternative for obtaining the compound (11) is presented in Scheme 2 below.

Scheme 2

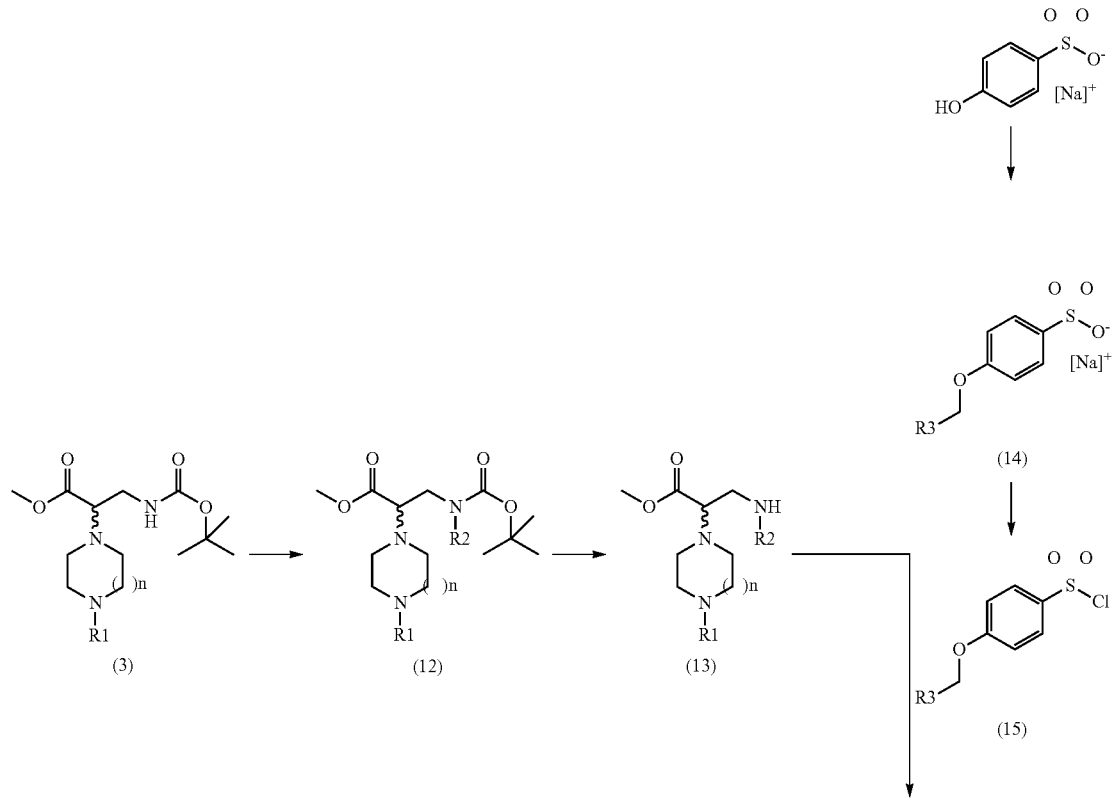

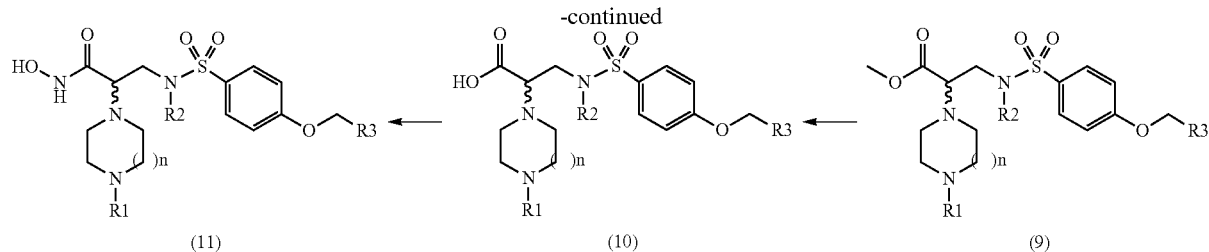

According to the synthesis scheme of Scheme 2, the derivative (3) can optionally be alkylated in the presence of a base such as sodium hydride and of an alkyl halide in dimethylformamide, for example, so as to give the compound (12), from which the compound (13) is obtained according to conventional methods for deprotecting amines, for instance the use of a solution of hydrochloric acid in isopropanol.

The compound (14) is prepared beforehand from the commercially available 4-hydroxybenzenesulfonic acid sodium salt by alkylation with an alkyl halide in the presence of a base such as sodium hydroxide, for example, in a mixture of solvents such as isopropanol and water, for example. The compound (15) is then obtained by reacting the derivative (14) with oxalyl chloride in the presence of dimethylformamide in dichloromethane, for example.

The derivative (9) is obtained by reaction between the compounds (13) and (15) in the presence of a base such as triethylamine in dichloromethane, for example.

An alternative synthesis pathway for obtaining the compound (11) is also presented in Scheme 3 below.

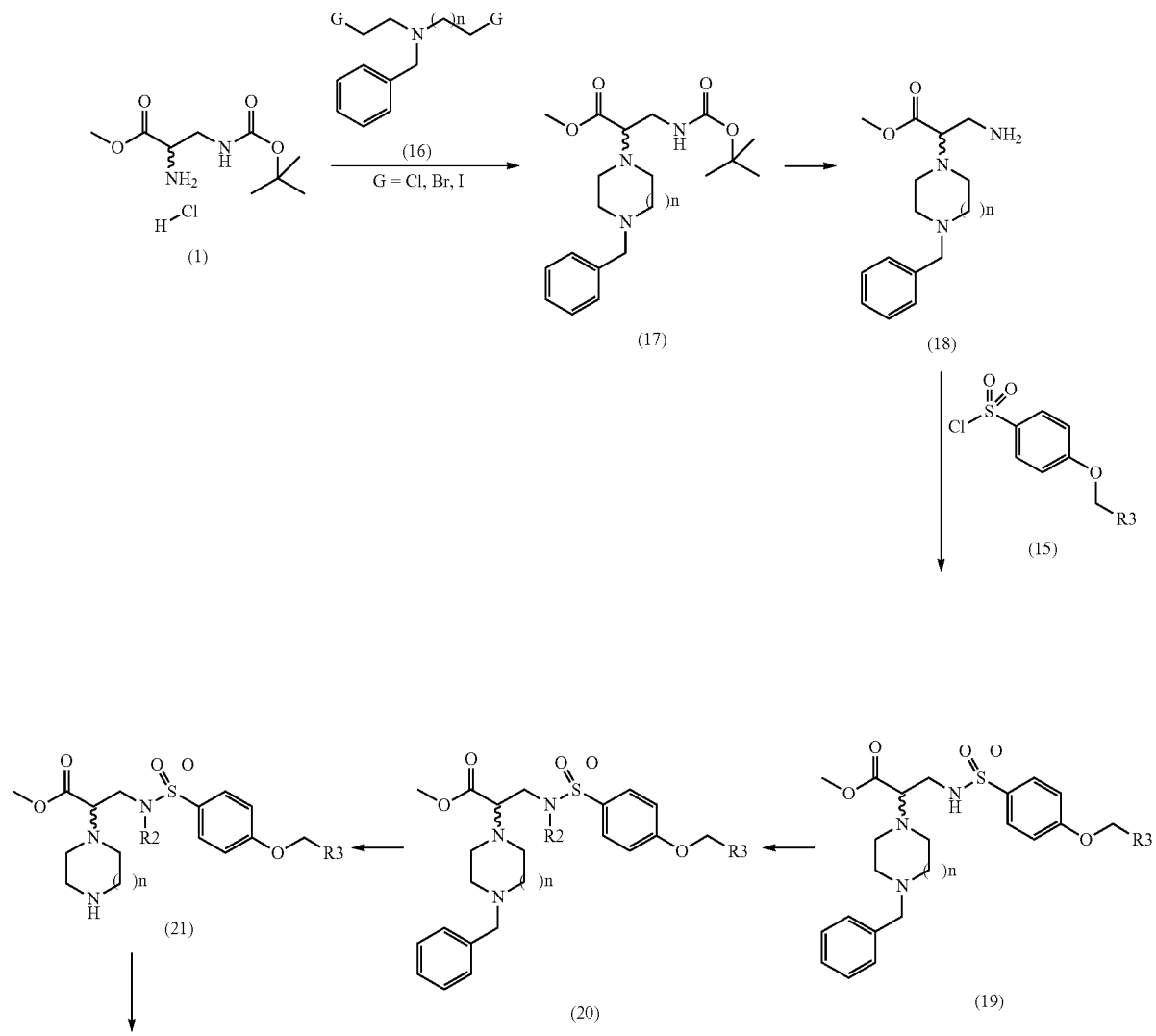

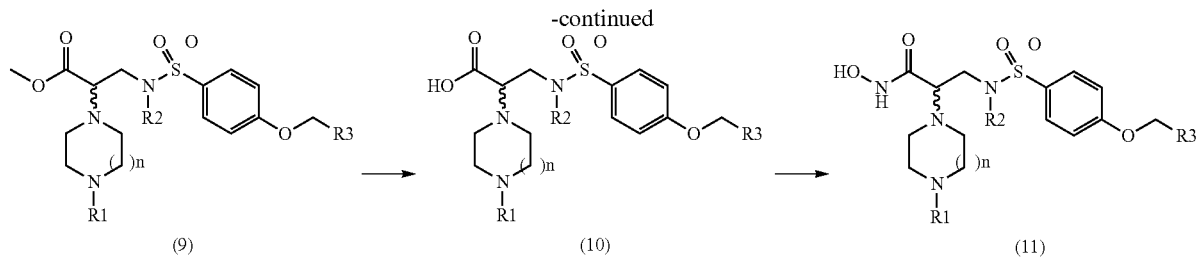

According to Scheme 3, the compound (17) is obtained by reaction between the amino acid (1) H-DAP(Boc)-OMe.HCl or H-(D)-DAP(Boc)-OMe.HCl and the compound (16) (prepared beforehand by reacting bis(2-chloroethyl)amine for example and benzyl bromide in the presence of potassium carbonate in acetonitrile) in the presence of an organic tertiary base such as diisopropylethylamine at a temperature of approximately 120° C. After deprotection of the amine function, the compound (18) is condensed with sulfonyl chloride (15) so as to give the derivative (19). An N-alkylation of the sulfonamide function can then be carried out by reaction with an alkyl halide in the presence of a base such as, for example, potassium carbonate in a solvent such as DMF, so as to give the derivative (20). The compound (21) is obtained according to the conventional conditions for hydrogenation of the compound (20) in the presence of palladium-on-carbon in a solvent such as ethanol for example. The compound (9) is obtained according to the conventional synthesis methods, for example, by reaction of the compound (21) with an acyl chloride, or a sulfonyl chloride in the presence of triethylamine, or by reaction with an alkyl halide in the presence of a base such as sodium hydride, for example. The compound (10) is obtained via a saponification reaction in the presence of a base such as lithium hydroxide in the presence of water and of tetrahydrofuran, for example. In a final step, the compound (11) is obtained by coupling between O-(tert-butyldimethylsilyl)hydroxylamine, for example, and the derivative (10) under conventional peptide coupling conditions, using, for example, 1-(3-dimethylaminopropyl)-3-ethylcarbodiimide hydrochloride, hydroxybenzotriazole or TBTU as coupling agents, and triethylamine or diisopropylethylamine as base, in a solvent such as dichloromethane or dimethylformamide. The deprotection of the silylated hydroxamic acid intermediately formed is carried out in situ or by washing with an acidic aqueous solution, so as to give the compound (11).

An alternative synthesis pathway for the compounds with R1 representing a —(CO)—R$_4$ radical is described in Scheme 4.

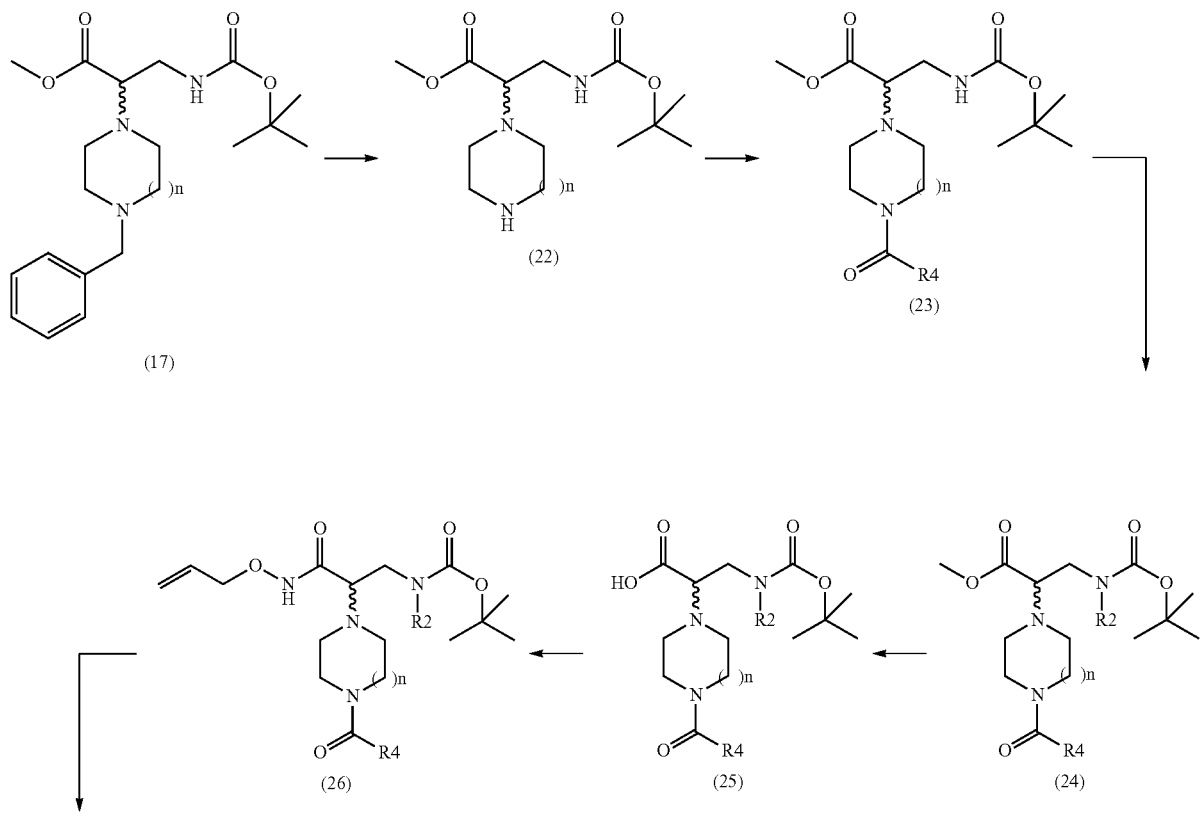

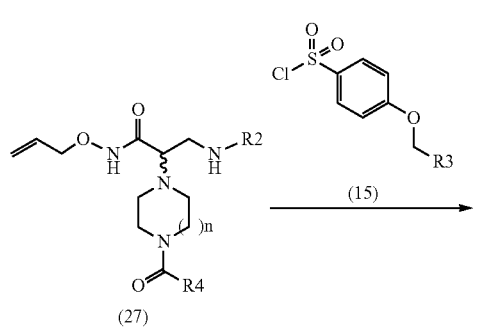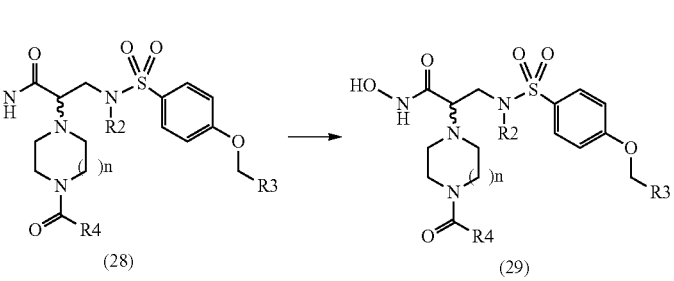

After deprotection of the amine function of the compound (17) according to conventional conditions for hydrogenation in the presence of palladium-on-carbon in a solvent such as ethanol for example, the compound (22) is obtained. The compound (23) is obtained by reaction with an acyl chloride, $R_4COCl$, in the presence of a base such as triethylamine. When $R_2$ represents a lower alkyl radical, an N-alkylation of the carbamate is then carried out by reaction with an alkyl halide in the presence of a base such as, for example, potassium carbonate in a solvent such as DMF, so as to give the derivative (24). The compound (25) is prepared via a saponification reaction in the presence of a base such as lithium hydroxide in the presence of water and of tetrahydrofuran, for example. Coupling between O-allylhydroxylamine hydrochloride, for example, and the derivative (25) makes it possible to obtain the compound (26) under conventional peptide coupling conditions. For this, use is made, for example, of 1-(3-dimethylaminopropyl)-3-ethylcarbodiimide hydrochloride, hydroxybenzotriazole or TBTU as coupling agents, and triethylamine or diisopropylethylamine as base. The reaction is carried out in a solvent such as dichloromethane or dimethylformamide. After deprotection of the amine function of the compound (26) according to conventional methods, the compound (27) is obtained. It is condensed with sulfonyl chloride (15) so as to give the compound (28). In a final step, the compound (29) is obtained by deprotection of the hydroxylamine function of the compound (28) according to conventional methods such as, for example, treatment with tetrakis(triphenylphosphine)palladium(0) and potassium carbonate in methanol.

According to the present invention, the preferred compounds of general formula (I) are those for which:
$R_1$ represents a hydrogen, an alkyl radical, a substituted alkyl radical, an alkenyl radical, a substituted alkenyl radical, an alkynyl radical, a substituted alkynyl radical, an aralkyl radical, a substituted aralkyl radical, a heteroaralkyl radical, a substituted heteroaralkyl radical, a —C(O)—$R_4$ radical, an —$SO_2$—$R_4$ radical or a C(O)$OR_4$ radical, $R_4$ having the meanings given hereinafter;
$R_2$ is a hydrogen atom or a a lower alkyl radical;
$R_3$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;
$R_4$ is an alkyl radical, a substituted alkyl radical, an alkenyl radical, a substituted alkenyl radical, an alkynyl radical, a substituted alkynyl radical, an aryl radical, a substituted aryl radical, an aralkyl radical or a substituted aralkyl radical;
n can take the values of 0, 1 or 2;
and also their addition salts with a pharmaceutically acceptable acid, their addition salts with a pharmaceutically acceptable base, and the enantiomers of said compounds.

According to the present invention, the particularly preferred compounds of general formula (I) are those for which:
$R_1$ represents a hydrogen, an alkyl radical, a substituted alkyl radical, an alkenyl radical, a substituted alkenyl radical, an alkynyl radical, a substituted alkynyl radical, an aralkyl radical, a substituted aralkyl radical, a —C(O)—$R_4$ radical or an —$SO_2$—$R_4$ radical, $R_4$ having the meanings given hereinafter;
$R_2$ is a hydrogen atom or a lower alkyl radical;
$R_3$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;
$R_4$ is an alkyl radical, a substituted alkyl radical, an aryl radical, a substituted aryl radical, an aralkyl radical or a substituted aralkyl radical;
n can take the values of 1 or 2;
and also their addition salts with a pharmaceutically acceptable acid, their addition salts with a pharmaceutically acceptable base, and the enantiomers of said compounds.

According to the present invention, the more particularly preferred compounds of general formula (I) are those for which:
$R_1$ represents an alkyl radical, a substituted alkyl radical, an aralkyl radical, a substituted aralkyl radical, a —C(O)—$R_4$ radical or an —$SO_2$—$R_4$ radical, $R_4$ having the meanings given hereinafter;
$R_2$ is a hydrogen atom;
$R_3$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;
$R_4$ is an alkyl radical, a substituted alkyl radical, an aryl radical, a substituted aryl radical, an aralkyl radical or a substituted aralkyl radical;
n takes the value of 1;
and also their addition salts with a pharmaceutically acceptable acid, their addition salts with a pharmaceutically acceptable base, and the enantiomers of said compounds.

According to the present invention, the even more particularly preferred compounds of general formula (I) are those for which:
$R_1$ represents an alkyl radical, a substituted alkyl radical, an aralkyl radical, a substituted aralkyl radical, a —C(O)—$R_4$ radical or an —$SO_2$—$R_4$ radical, $R_4$ having the meanings given hereinafter;

$R_2$ is a hydrogen atom;

$R_3$ is a heterocyclic radical, a substituted heterocyclic radical, a heteroaryl radical, a substituted heteroaryl radical, a heteroaralkyl radical or a substituted heteroaralkyl radical;

$R_4$ is an alkyl radical, a substituted alkyl radical, an aryl radical, a substituted aryl radical, an aralkyl radical or a substituted aralkyl radical;

n takes the value of 1;

and also their addition salts with a pharmaceutically acceptable acid, their addition salts with a pharmaceutically acceptable base, and the enantiomers of said compounds.

According to the present invention, the most particularly preferred compounds of general formula (I) are those for which:

$R_1$ represents an alkyl radical, a substituted alkyl radical, an aralkyl radical, a substituted aralkyl radical, a —C(O)—$R_4$ radical or an —$SO_2$—$R_4$ radical, $R_4$ having the meanings given hereinafter;

$R_2$ is a hydrogen atom;

$R_3$ is a heteroaryl radical or a substituted heteroaryl radical;

$R_4$ is an alkyl radical, a substituted alkyl radical, an aryl radical, a substituted aryl radical, an aralkyl radical or a substituted aralkyl radical;

n takes the value of 1;

and also their addition salts with a pharmaceutically acceptable acid, their addition salts with a pharmaceutically acceptable base, and the enantiomers of said compounds.

The compounds according to the invention exhibit a very good TACE-inhibiting activity and, in particular, they inhibit the TACE enzyme selectively compared with other ADAMs and MMPs. This TACE enzyme-inhibiting activity is measured in an enzymatic assay and quantified via the measurement of an $IC_{50}$ (inhibitory concentration necessary to obtain 50% inhibition of the TACE enzyme), as described in example 28. The compounds of the present invention have an $IC_{50}$ for TACE less than or equal to 10 μM and more particularly less than or equal to 1 μM. Advantageously, the compounds of the present invention have an $IC_{50}$ for TACE less than or equal to 0.5 μM.

Advantageously, these compounds are also very selective for TACE compared with the other ADAMs and MMPs (assay described in example 29): their inhibitory activity is at least 10 times greater for TACE than for other ADAMs and MMPs (i.e. the $IC_{50}$ value for TACE is at least 10 times smaller than that for other ADAMs and MMPs), and more advantageously at least 100 times greater.

TACE (TNFα-converting enzyme) catalyses the formation of soluble TNF-alpha from the precursor protein (transmembrane TNFα) bound to the membranes of certain cells. TNFα is a pro-inflammatory cytokine which is known to play a role in many pathological conditions with an inflammatory nature.

The invention is therefore directed toward the use of at least one compound of general formula (I) as defined above, for the treatment of pathological conditions and disorders linked to TNFα release. A TACE enzyme inhibitor of general formula (I) decreases TNFα production. As a result, it is of use for the treatment of pathological conditions linked to TNFα release.

The invention is also directed toward the use of at least one compound of general formula (I) as defined above, for preparing a pharmaceutical or cosmetic composition in which said compound has TACE enzyme-inhibiting activity.

It is therefore directed toward the use of at least one compound of general formula (I) as defined above, for the treatment of pathological conditions or disorders which are improved by inhibiting the TACE enzyme.

The invention also relates to a method of therapeutic (human or animal) or cosmetic treatment, which consists of the administration or the application of a pharmaceutical or cosmetic composition comprising a compound of general formula (I) as a TACE inhibitor and, consequently, as an inhibitor of soluble TNFα production.

Thus, the invention relates to the use of at least one compound of general formula (I) as defined above, for the treatment of pathological conditions or disorders linked to TNFα production.

The invention also relates to the use of a compound of general formula (I) as defined above, for preparing a medicament intended for the treatment of pathological conditions for which reducing TNFα production would be of great interest.

Indeed, the compounds used according to the invention are particularly suitable for the treatment and prevention of disorders/diseases such as the inflammatory diseases listed hereinafter, but are not limited thereto, such as septic shock, hemodynamic shock, malaria, inflammatory bowel diseases (IBDs) such as Crohn's disease and ulcerative colitis, inflammatory bone diseases, mycobacterial infections, meningitis, fibrotic diseases, cardiac diseases, atherosclerosis, obesity, ischemic attack, transplant rejection, cancer, diseases involving angiogenesis phenomena, autoimmune diseases, osteoarthritis, rheumatoid arthritis, ankylosing spondylitis, juvenile chronic arthritis, multiple sclerosis, HIV, non-insulin-dependent diabetes mellitus, allergic diseases, asthma, chronic obstructive pulmonary disease (COPD), inflammatory skin diseases, psoriasis, atopic dermatitis and psoriatic arthritis.

These molecules are also potential active ingredients for the treatment of neurological pathological conditions with an inflammatory nature, for which reducing TNFα production would be of great interest. These pathological conditions listed hereinafter in a nonlimiting manner are, for example, Alzheimer's disease, Parkinson's disease, parkinsonian disorders, amyotrophic lateral sclerosis, autoimmune diseases of the nervous system, autonomic diseases of the nervous system, dorsal pain, cerebral edema, cerebrovascular disorders, dementia, nervous system nerve fiber demyelinating autoimmune diseases, diabetic neuropathies, encephalitis, encephalomyelitis, epilepsy, chronic fatigue syndrome, giant cell arteritis, Guillain-Barré syndrome, headaches, multiple sclerosis, neuralgia, peripheral nervous system diseases, polyneuropathies, polyradiculoneuropathy, radiculopathy, respiratory paralysis, spinal cord diseases, Tourette's syndrome, central nervous system vasculitis, Huntington's disease and stroke.

The invention relates to the use of a compound of general formula (I) as defined above, for preparing a medicament intended for the treatment of pathological conditions with an inflammatory nature, in which TNFα is involved.

The invention relates to the use of a compound of general formula (I) as defined above, for preparing a medicament intended for the treatment of inflammatory skin diseases, of psoriasis, of atopic dermatitis or of psoriatic arthritis.

A subject of the present invention is also a pharmaceutical composition intended in particular for the treatment of the abovementioned conditions, and which is characterized in that it comprises, in a carrier which is pharmaceutically acceptable and compatible with the method of administration selected for this composition, at least one compound of general formula (I). This compound of general formula (I) can also be in one of its enantiomeric forms or in the form of one of its pharmaceutically acceptable salts. Several examples of preparation of active compounds of formula (I) according to the invention, and also of the results of biological activity of such compounds, will now be given by way of illustration and without being in any way limiting in nature.

EXEMPLARY EMBODIMENTS

The compounds of general formula (I) are characterized by proton NMR analysis on a Bruker Avance 400 MHz instrument.

Example 1

3-[(4-but-2-ynyloxybenzenesulfonyl)methylamino]-N-hydroxy-2-(4-methanesulfonylpiperazin-1-yl) propionamide

1-1: Dimethyl 2-(4-tert-butoxycarbonylpiperazin-1-yl)malonate 19.5 g (141 mmol) of potassium carbonate and then 19.5 ml (134 mmol) of dimethyl bromomalonate are added to a solution of 25 g (134 mmol) of tert-butyl piperazine-1-carboxylate in 300 ml of acetonitrile. The reaction medium is stirred at ambient temperature for 24 h and then filtered in order to remove the insoluble salts, and concentrated under vacuum. The crude residue obtained is purified by chromatography on silica gel, elution being carried out with a 70/30 heptane/ethyl acetate mixture. 41 g (97%) of dimethyl 2-(4-tert-butoxycarbonylpiperazin-1-yl)malonate are obtained in the form of a light oil.

1-2: Dimethyl 2-(4-tert-butoxycarbonylpiperazin-1-yl)-2-(1,3-dioxo-1,3-dihydroisoindol-2-ylmethyl) malonate 3.5 g (87 mmol) of sodium hydride are added portionwise to a solution of 25 g (87 mmol) of dimethyl 2-(4-tert-butoxycarbonylpiperazin-1-yl)malonate in 250 ml of tetrahydrofuran cooled to 2° C. The reaction medium is stirred at ambient temperature for 30 minutes and then brought back to 2° C., before adding, dropwise, 21 g (87 mmol) of 2-bromomethyl-isoindole-1,3-dione in 200 ml of tetrahydrofuran. The reaction medium is stirred at ambient temperature for 20 h, treated by adding 500 ml of water and then extracted with ethyl acetate. The organic phase is dried over magnesium sulfate, filtered, and concentrated under vacuum.

The crude product obtained is purified by chromatography on silica gel, elution being carried out with a 70/30 heptane/ethyl acetate mixture. 27.5 g (73%) of dimethyl 2-(4-tert-butoxycarbonylpiperazin-1-yl)-2-(1,3-dioxo-1,3-dihydroisoindol-2-ylmethyl)malonate are obtained in the form of a white solid.

1-3: Dimethyl 2-aminomethyl-2-(4-tert-butoxycarbonylpiperazin-1-yl)malonate A solution of 2.9 ml (64 mmol) of hydrazine hydrate in 8 ml of methanol is added to a solution of 27.5 g (58 mmol) of dimethyl 2-(4-tert-butoxycarbonylpiperazin-1-yl)-2-(1,3-dioxo-1,3-dihydroisoindol-2-ylmethyl)malonate in 300 ml of methanol cooled beforehand to −5° C. The reaction medium is stirred at from −5° C. to ambient temperature over the course of 3 h. After evaporation and addition of 300 ml of water, the reaction medium is extracted with ethyl acetate. The organic phases are washed with a saturated aqueous solution of sodium hydrogen carbonate, dried over magnesium sulfate, filtered and evaporated. The residue obtained is purified by chromatography on silica gel, elution being carried out with an 8/2 heptane/ethyl acetate mixture and then an increase in polarity up to a 90/10 ethyl acetate/methanol mixture. 10 g (50%) of dimethyl 2-aminomethyl-2-(4-tert-butoxycarbonylpiperazin-1-yl)malonate are thus obtained in the form of a light oil.

1-4: Dimethyl 2-(4-tert-butoxycarbonylpiperazin-1-yl)-2-[(4-but-2-ynyloxybenzenesulfonylamino)methyl]malonate 1.1 ml (8 mmol) of triethylamine and then 1.8 ml (7 mmol) of 4-but-2-ynyloxybenzenesulfonyl chloride are added to a solution of 2.5 g (7 mmol) of dimethyl 2-aminomethyl-2-(4-tert-butoxycarbonylpiperazin-1-yl)malonate in 30 ml of dichloromethane. The reaction medium is stirred at ambient temperature for 2 hours and then concentrated under vacuum. The crude product obtained is purified by chromatography on silica gel, elution being carried out with a 70/30 heptane/ethyl acetate mixture. 2.1 g (51%) of dimethyl 2-(4-tert-butoxycarbonylpiperazin-1-yl)-2-[(4-but-2-ynyloxybenzenesulfonylamino)methyl]malonate are obtained in the form of a white solid.

1-5: Dimethyl 2-[(4-but-2-ynyloxybenzenesulfonylamino)methyl]-2-piperazin-1-ylmalonate 2.8 ml of trifluoroacetic acid are added to a solution of 2.1 g (4 mmol) of dimethyl 2-(4-tert-butoxycarbonylpiperazin-1-yl)-2-[(4-but-2-ynyloxybenzenesulfonylamino)methyl] malonate diluted in 30 ml of dichloromethane. After stirring at ambient temperature for 24 h, a saturated aqueous solution of sodium hydrogen carbonate is added to pH=8 and the reaction medium is extracted with dichloromethane. The organic phases are combined, washed with water, dried over magnesium sulfate, and then filtered and evaporated. 1.7 g (98%) of dimethyl 2-[(4-but-2-ynyloxybenzenesulfonylamino)methyl]-2-piperazin-1-ylmalonate are obtained in the form of a white solid.

1-6: Dimethyl 2-[(4-but-2-ynyloxybenzenesulfonylamino)methyl]-2-(4-methanesulfonylpiperazin-1-yl) malonate 0.6 ml (4 mmol) of triethylamine and then 0.3 ml (4 mmol) of methanesulfonyl chloride are added to a solution of 1.6 g (4 mmol) of dimethyl 2-[(4-but-2-ynyloxybenzenesulfonylamino)methyl]-2-piperazin-1-ylmalonate diluted in 30 ml of dichloromethane. The reaction medium is then stirred at ambient temperature for 3 h and then evaporated to dryness. The crude residue is purified by chromatography on silica gel, elution being carried out with a 99/1 dichloromethane/methanol mixture. 1.1 g (58%) of dimethyl 2-[(4-but-2-ynyloxybenzenesulfonylamino)methyl]-2-(4-methanesulfonylpiperazin-1-yl)malonate are obtained in the form of a white solid.

1-7: Dimethyl 2-{(4-but-2-ynyloxybenzenesulfonyl) methylamino]methyl}-2-(4-methanesulfonylpiperazin-1-yl)malonate 120 mg (0.9 mmol) of potassium carbonate and then 56 μl (0.9 mmol) of methyl iodide are added to a solution of 400 mg (0.8 mmol) of dimethyl 2-[(4-but-2-ynyloxybenzenesulfonylamino)methyl]-2-(4-methanesulfonylpiperazin-1-yl)malonate in 10 ml of dimethylformamide. The reaction medium is then stirred at ambient temperature for 18 h and then hydrolyzed by adding water and extracted with ethyl acetate. The organic phases are washed with water and then dried over magnesium sulfate, filtered and concentrated under vacuum. The crude product obtained is purified by chromatography on silica gel, elution being carried out with a 50/50 heptane/ethyl acetate mixture. 410 mg (100%) of dimethyl 2-{[(4-but-2-ynyloxybenzenesulfonyl)methylamino]methyl}-2-(4-methanesulfonylpiperazin-1-yl)malonate are obtained in the form of a white solid.

1-8: 3-[(4-But-2-ynyloxybenzenesulfonyl)methylamino]-2-(4-methanesulfonylpiperazin-1-yl)propanoic Acid 1.7 ml (1.7 mmol) of an aqueous solution of sodium hydroxide having a concentration of 1M are added to a solution of 270 mg (0.5 mmol) of dimethyl 2-{[(4-but-2-ynyloxybenzenesulfonyl)methylamino]methyl}-2-(4-methanesulfonylpiperazin-1-yl)malonate in 7 ml of tetrahydrofuran and 2 ml of methanol. The reaction medium is stirred at 40° C. for 15 h and then brought back to pH=6 by adding an aqueous solution of hydrochloric acid having a concentration of 1M. After evaporation of the solvents under vacuum, the product precipitates. The residue obtained is taken up in 5 ml of water and stirred for 30 min until precipitation occurs. The product is filtered off, rinsed with water and then dried under vacuum. 200 mg (87%) of 3-[(4-but-2-ynyloxybenzenesulfonyl)methylamino]-2-(4-methanesulfonylpiperazin-1-yl)propanoic acid are obtained in the form of a white solid.

1-9: 3-[(4-But-2-ynyloxybenzenesulfonyl)methylamino]-N-hydroxy-2-(4-methanesulfonylpiperazin-1-yl)propionamide 63 mg (0.5 mmol) of 1-hydroxybenzotriazole and then 88 mg (0.5 mmol) of 1-ethyl-3-(3-dimethylaminopropyl)carbodiimide hydrochloride are added to a solution of 200 mg (0.4 mmol) of 3-[(4-but-2-ynyloxybenzenesulfonyl)methylamino]-2-(4-methanesulfonylpiperazin-1-yl)propanoic acid in 6 ml of dimethylformamide. The reaction medium is stirred for 10 min at ambient temperature and then 68 mg (0.5 mmol) of O-tert-butyldimethysilylhydroxylamine are added. The reaction medium is then stirred at ambient temperature for 24 h, hydrolyzed by adding 2 ml of a 5% aqueous citric acid solution, and stirred for a further 30 minutes. After extraction with ethyl acetate, the organic phase is washed with water, dried over magnesium sulfate, filtered and concentrated. The crude residue is purified by chromatography on silica gel, elution being carried out with a 95/5 dichloromethane/methanol mixture. 100 mg (50%) of 3-[(4-but-2-ynyloxybenzenesulfonyl)methylamino]-N-hydroxy-2-(4-methanesulfonylpiperazin-1-yl)propionamide are obtained in the form of a white solid with a melting point of 86° C.

$^1$H NMR (δ, DMSO): 1.91 (s, 3H); 2.63-2.68 (m, 2H); 2.72 (s, 3H); 2.72-2.75 (m, 2H); 2.92 (s, 3H); 3.05-3.15 (m, 5H); 3.30-3.38 (m, 2H); 4.93 (s, 2H); 7.24 (d, J=6.8 Hz, 2H); 7.79 (d, J=6.8 Hz, 2H); 9.06 (s, 1H); 10.77 (s, 1H).

Example 2

(S)-3-(4-but-2-ynyloxybenzenesulfonylamino)-N-hydroxy-2-(4-methanesulfonylpiperazin-1-yl)propionamide

2.1: Sodium Salt of 4-but-2-ynyloxybenzenesulfonic Acid 50 g (370 mmol) of 1-bromo-2-butyne are added to a solution of 43 g (185 mmol) of commercial sodium salt of 4-hydroxybenzenesulfonic acid and of 185 ml (185 mmol) of an aqueous solution of sodium hydroxide having a concentration of 1M, in 800 ml of isopropanol. The reaction medium is heated at 70° C. for 18 h.

After evaporation of the isopropanol, the product obtained is filtered, rinsed with isopropanol and with diethyl ether and then dried under vacuum. 46 g (100%) of the sodium salt of 4-but-2-ynyloxybenzenesulfonic acid are obtained in the form of a white solid.

2.2: 4-But-2-ynyloxybenzenesulfonyl Chloride 30 g (107 mmol) of the sodium salt of 4-but-2-ynyloxybenzenesulfonic acid in 120 ml of dimethylformamide are added dropwise to a solution of 28 ml (321 mmol) of oxalyl chloride in 120 ml of dichloromethane, cooled beforehand to −10° C., and then the reaction medium is stirred at ambient temperature for 18 h. 800 ml of ice are added and the medium is extracted with ethyl acetate. The organic phases are combined, washed with water, dried over magnesium sulfate, filtered and concentrated under vacuum. 22 g (84%) of 4-but-2-ynyloxybenzenesulfonyl chloride are obtained in the form of a beige solid.

2.3: N,N-bis(2-Chloroethyl)methanesulfonamide 8.6 ml (62 mmol) of triethylamine are added to a solution of 5 g (28 mmol) of bis(2-chloroethyl)amine hydrochloride in 60 ml of dichloromethane. The triethylammonium chloride salts precipitate and are filtered off. 2.4 ml (31 mmol) of methylsulfonyl chloride are then added to the filtrate obtained, and the reaction medium is stirred at ambient temperature for 3 h. After the addition of water, the product is extracted with dichloromethane. The organic phase is washed with water, dried over magnesium sulfate, filtered and concentrated. 5.8 g (94%) of N,N-bis(2-chloroethyl)methanesulfonamide are obtained in the form of a beige solid.

2.4: Methyl (S)-3-tert-butoxycarbonylamino-2-(4-methanesulfonylpiperazin-1-yl)propanoate In a Schlenk tube, a solution of 5 g (20 mmol) of methyl (S)-2-amino-3-tert-butoxycarbonylaminopropanoate hydrochloride and 4.3 g (20 mmol) of N,N-bis(2-chloroethyl)methanesulfonamide in 65 ml of N,N-diisopropylethylamine is heated at 127° C. with vigorous stirring for 18 h. After the addition of water, the product is extracted with ethyl acetate. The organic phases are combined, washed with water, dried over magnesium sulfate, filtered and concentrated under vacuum. The crude product obtained is purified by chromatography on silica gel, elution being carried out with a 50/50 heptane/ethyl acetate mixture. 3.3 g (46%) of methyl (S)-3-tert-butoxycarbonylamino-2-(4-methanesulfonylpiperazin-1-yl)propanoate are obtained in the form of a white solid.

2.5: Methyl (S)-3-amino-2-(4-methanesulfonylpiperazin-1-yl)propanoate Hydrochloride 15 ml of a solution of hydrochloric acid in isopropanol, having a concentration of 5-6N are added dropwise to a solution of 2.7 g (7.4 mmol) of methyl (S)-3-tert-butoxycarbonylamino-2-(4-methanesulfonylpiperazin-1-yl)propanoate in 30 ml of methanol. The reaction medium is stirred at 40° C. for 2 h, concentrated under vacuum, and then taken up in 20 ml of methanol and 150 ml of diethyl ether. The product precipitates, and is filtered off under vacuum, rinsed with diethyl ether and then dried under vacuum. 2.3 g (100%)

of methyl (S)-3-amino-2-(4-methanesulfonylpiperazin-1-yl) propanoate hydrochloride are obtained in the form of a white solid.

2.6: Methyl (S)-3-(4-but-2-ynyloxybenzenesulfonylamino)-2-(4-methanesulfonylpiperazin-1-yl)propanoate 0.3 ml (2 mmol) of triethylamine and 270 mg (1 mmol) of 4-but-2-ynyloxybenzenesulfonyl chloride (prepared as described in 2.2) are added to a solution of 300 mg (1 mmol) of methyl (S)-3-amino-2-(4-methanesulfonylpiperazin-1-yl) propanoate hydrochloride (prepared as described in 2.5) in 8 ml of dichloromethane. After stirring at ambient temperature for 18 h, water is added and the reaction medium is extracted with dichloromethane. The organic phases are washed with water, dried over magnesium sulfate, filtered and concentrated.

The crude product obtained is purified by chromatography on silica gel, elution being carried out with a 50/50 heptane/ethyl acetate mixture. 400 mg (85%) of methyl (S)-3-(4-but-2-ynyloxybenzenesulfonylamino)-2-(4-methanesulfonylpiperazin-1-yl)propanoate are obtained in the form of a white solid.

2.7: (S)-3-(4-But-2-ynyloxybenzenesulfonylamino)-2-(4-methanesulfonylpiperazin-1-yl)propanoic Acid 1.3 ml (1.3 mmol) of an aqueous solution of lithium hydroxide having a concentration of 1M are added to a solution of 400 mg (0.8 mmol) of methyl (S)-3-(4-but-2-ynyloxybenzenesulfonylamino)-2-(4-methanesulfonylpiperazin-1-yl)propanoate diluted in 10 ml of tetrahydrofuran cooled beforehand to 0° C. The reaction medium is stirred at ambient temperature for 20 h. After evaporation to dryness, 1.5 ml of an aqueous solution of acetic acid having a concentration of 1M are added so as to obtain a pH=6. The product precipitates, and is filtered off, rinsed with water and then with diethyl ether and dried under vacuum. 340 mg (89%) of (S)-3-(4-but-2-ynyloxybenzenesulfonylamino)-2-(4-methanesulfonylpiperazin-1-yl)propanoic acid are obtained in the form of a white solid.

2.8: (S)-3-(4-But-2-ynyloxybenzenesulfonylamino)-N-hydroxy-2-(4-methanesulfonylpiperazin-1-yl) propionamide 120 mg (0.9 mmol) of 1-hydroxybenzotriazole and 170 mg (0.9 mmol) of 1-ethyl-3-(3-dimethylaminopropyl)carbodiimide hydrochloride are added to a solution of 340 mg (0.7 mmol) of (S)-3-(4-but-2-ynyloxybenzenesulfonylamino)-2-(4-methanesulfonylpiperazin-1-yl)propanoic acid in 8 ml of dimethylformamide. The reaction medium is stirred for 30 min, and then 120 mg (0.8 mmol) of O-tert-butyldimethysilylhydroxylamine in 3 ml of dimethylformamide are added. The reaction medium is then stirred at ambient temperature for 20 h, and then hydrolyzed with 2 ml of water and 2 ml of a 5% aqueous solution of citric acid. After stirring for 30 min, a saturated aqueous solution of sodium hydrogen carbonate is added to pH=8, and then the reaction medium is extracted with ethyl acetate. The organic phase is dried over magnesium sulfate, filtered and concentrated. The residue is taken up in dichloromethane, filtered, and then dried under vacuum. 80 mg (23%) of (S)-3-(4-but-2-ynyloxybenzenesulfonylamino)-N-hydroxy-2-(4-methanesulfonylpiperazin-1-yl) propionamide are obtained in the form of a white solid with a melting point of 150° C.

$^1$H NMR (δ, DMSO): 1.86 (s, 3H); 2.55 (m, 4H); 2.83 (s, 3H); 2.85-2.88 (m, 1H); 2.97-3.00 (m, 3H); 3.00-3.06 (m, 2H); 3.10-3.12 (t, J=4.8 Hz, 1H); 4.86 (s, 2H); 7.15 (d, J=9.2 Hz, 2H); 7.51 (s, 1H); 7.75 (d, J=9.2 Hz, 2H); 8.94 (s, 1H); 10.6 (s, 1H).

Example 3

(S)-3-(4-benzyloxy-benzenesulfonylamino)-N-hydroxy-2-(4-methanesulfonylpiperazin-1-yl)propionamide

3.1: N,N-bis-(2-Chloroethyl)methanesulfonamide 14.3 ml (185 mmol) of methanesulfonyl chloride are added slowly to a solution of 15 g (84 mmol) of commercial bis(2-chloroethylamine) hydrochloride and 26 ml (185 mmol) of triethylamine in 200 ml of dichloromethane and 70 ml of tetrahydrofuran previously stirred for 15 min and then filtered in order to remove the triethylammonium chloride. The reaction medium is then stirred at ambient temperature for 18 h, extracted with dichloromethane, and washed with water. The organic phase is dried over magnesium sulfate, filtered and evaporated. The residue obtained is washed with diisopropyl ether, filtered and then dried under vacuum. 15.3 g (82%) of N,N-bis-(2-chloroethyl)methanesulfonamide are obtained in the form of a solid.

3.2: Methyl (S)-3-tert-butoxycarbonylamino-2-(4-methanesulfonylpiperazin-1-yl)propanoate A solution of 9.6 g (44 mmol) of N,N-bis-(2-chloroethyl) methanesulfonamide and 11.1 g (44 mmol) of methyl 2-amino-3-tert-butoxypropanoate hydrochloride in 90 ml of diisopropylethylamine is heated at 127° C. for 18 h. The reaction medium is evaporated to dryness. 31 g of crude residue are obtained and purified by chromatography on silica gel, elution being carried out with a 9/1 heptane/ethyl acetate mixture and then an increase in polarity up to 4/6. 5.5 g (35%) of methyl (S)-3-tert-butoxycarbonylamino-2-(4-methanesulfonylpiperazin-1-yl)propanoate are obtained.

3.3: Methyl (S)-3-amino-2-(4-methanesulfonylpiperazin-1-yl)propanoate Dihydrochloride A solution of 4 g (11 mmol) of methyl (S)-3-tert-butoxycarbonylamino-2-(4-methanesulfonylpiperazin-1-yl)propanoate (prepared as described in example 2.4) in 40 ml of methanol and 20 ml of a solution of hydrochloric acid in isopropanol, having a concentration of 5 or 6M, is stirred at 40° C. for 18 h and then concentrated under vacuum. The residue obtained is taken up in 200 ml of diethyl ether, filtered, and then dried under vacuum. 3.5 g (94%) of methyl (S)-3-amino-2-(4-methanesulfonylpiperazin-1-yl)propanoate dihydrochloride are obtained in the form of a beige solid.

3.4: Sodium Salt of 4-benzyloxybenzenesulfonic Acid 64 ml (539 mmol) of benzyl bromide are added to a solution of 50 g (215 mmol) of the sodium salt of 4-hydroxybenzenesulfonic acid dihydrate in 700 ml of isopropanol and 250 ml (250 mmol) of an aqueous solution of sodium hydroxide having a concentration of 1M. The reaction medium is heated at 70° C. for 20 h. After concentration of the isopropanol under vacuum, the product precipitates and is filtered off. 61 g (100%) of the sodium salt of 4-benzyloxybenzenesulfonic acid are obtained in the form of a white solid.

3.5: 4-Benzyloxybenzenesulfonyl Chloride

A solution of 55 ml (639 mmol) of oxalyl chloride in 250 ml of dichloromethane is added dropwise to a solution of 61 g (213 mmol) of the sodium salt of 4-benzyloxybenzenesulfonic acid in 200 ml of dimethylformamide, while maintaining the temperature between −20° C. and −10° C. After addition, the reaction medium is slowly brought back to ambient temperature and then stirred for 18 h, poured onto ice and extracted with ethyl acetate. The organic phase is washed with water and with a saturated aqueous solution of sodium chloride and concentrated under vacuum. 54 g (89%) of 4-benzyloxybenzenesulfonyl chloride are obtained in the form of a white solid.

3.6: Methyl (S)-3-(4-benzyloxybenzenesulfonylamino)-2-(4-methanesulfonylpiperazin-1-yl)propanoate 1.1 ml (7.8 mmol) of triethylamine and then 730 mg (2.6 mmol) of 4-benzyloxybenzenesulfonyl chloride in 8 ml of dichloromethane are added to a solution of 800 mg (2.4 mmol) of methyl (S)-3-amino-2-(4-methanesulfonylpiperazin-1-yl)propanoate dihydrochloride in 20 ml of dichloromethane and the reaction medium is stirred at ambient temperature for 3 h. After the addition of water, the product is extracted with dichloromethane. The organic phase is washed with water, dried over magnesium sulfate, filtered and concentrated.

The residue obtained is purified by chromatography on silica gel, elution being carried out with an 8/2 heptane/ethyl acetate mixture. 0.9 g (75%) of methyl (S)-3-(4-benzyloxybenzenesulfonylamino)-2-(4-methanesulfonylpiperazin-1-yl)propanoate are obtained in the form of a white solid.

3.7: (S)-3-(4-Benzyloxybenzenesulfonylamino)-2-(4-methanesulfonylpiperazin-1-yl)propanoic Acid 2.6 ml (2.6 mmol) of an aqueous solution of lithium hydroxide having a concentration of 1M are added to a solution of 900 mg (1.8 mmol) of methyl (S)-3-(4-benzyloxybenzenesulfonylamino)-2-(4-methanesulfonylpiperazin-1-yl)propanoate in 20 ml of tetrahydrofuran and 0.5 ml of water. The reaction medium is stirred at ambient temperature for 18 h and then the THF is evaporated off under vacuum. 2.8 ml of an aqueous solution of acetic acid having of concentration of 1M and then 30 ml of water are added and the product precipitates. The suspension is stirred for 30 min at 100° C. and then brought back to ambient temperature, filtered and dried under vacuum. 750 mg (86%) of (S)-3-(4-benzyloxybenzenesulfonylamino)-2-(4-methanesulfonylpiperazin-1-yl)propanoic acid are obtained in the form of a white solid.

3.8: (S)-3-(4-Benzyloxybenzenesulfonylamino)-N-hydroxy-2-(4-methanesulfonyl-piperazin-1-yl)propionamide 224 mg (1.7 mmol) of 1-hydroxybenzotriazole and 318 mg (1.7 mmol) of 1-ethyl-3-(3-dimethylaminopropyl)carbodiimide hydrochloride are added successively to 750 mg (1.5 mmol) of (S)-3-(4-benzyloxybenzenesulfonylamino)-2-(4-methanesulfonylpiperazin-1-yl)propanoic acid in 20 ml of dimethylformamide. After stirring at ambient temperature for 20 min, a solution of 244 mg (1.7 mmol) of O-tert-butyldimethylsilylhydroxylamine in 3 ml of dimethylformamide is added. The reaction medium is then stirred at ambient temperature for 18 h and then 2 ml of a saturated aqueous solution of sodium hydrogen carbonate and finally 2 ml of water are added. After extraction with ethyl acetate, the organic phase is washed with a saturated aqueous solution of sodium hydrogen carbonate, dried over magnesium sulfate, filtered and concentrated. The crude residue obtained is taken up in 15 ml of ethyl acetate, heated to 70° C. and then brought back to ambient temperature, filtered and dried under vacuum.

300 mg (34%) of (S)-3-(4-benzyloxybenzenesulfonylamino)-N-hydroxy-2-(4-methanesulfonylpiperazin-1-yl)propionamide are obtained in the form of a white solid having a melting point of 165° C.

$^1$H NMR (δ, DMSO): 2.40-2.50 (m, 2H); 2.50-2.60 (m, 2H); 2.84 (s, 3H), 3.00-3.05 (m, 4H); 3.06-3.09 (m, 2H); 3.34 (s, 1H); 5.19 (s, 2H); 7.19 (d, J=8.4 Hz, 2H); 7.30-7.34 (m, 1H); 7.35-7.47 (m, 5H); 7.73 (d, J=8.4 Hz, 2H); 8.93 (s, 1H); 10.65 (s, 1H).

Example 4

(S)-3-[(4-Benzyloxybenzenesulfonyl)methylamino]-N-hydroxy-2-(4-methanesulfonylpiperazin-1-yl)propionamide

4.1: Methyl (S)-3-[(4-benzyloxybenzenesulfonyl)methylamino]-2-(4-methanesulfonylpiperazin-1-yl)propanoate 300 mg (1.9 mmol) of potassium carbonate and then 0.2 ml (3.1 mmol) of methyl iodide are added to a solution of 800 mg (1.6 mmol) of methyl (S)-3-(4-benzyloxybenzenesulfonylamino)-2-(4-methanesulfonylpiperazin-1-yl)propanoate (prepared as described in 3.6) in 15 ml of dimethylformamide. The reaction medium is then stirred at ambient temperature for 20 h, hydrolyzed, and then diluted with ethyl acetate. The product is extracted with ethyl acetate. The organic phases are washed with water, dried over magnesium sulfate and filtered.

The filtrate is concentrated under vacuum, to give 820 mg (100%) of methyl (S)-3-(4-benzyloxybenzenesulfonylamino)-2-(4-methanesulfonylpiperazin-1-yl)propanoate in the form of a white solid.

4.2: (S)-3-[(4-Benzyloxybenzenesulfonyl)methylamino]-2-(4-methanesulfonylpiperazin-1-yl)propanoic Acid In a manner analogous to example 3.7, using 820 mg (1.6 mmol) of methyl (S)-3-[(4-benzyloxybenzenesulfonyl)methylamino]-2-(4-methanesulfonylpiperazin-1-yl)propanoate, 720 mg (90%) of (S)-3-[(4-benzyloxybenzenesulfonyl)methylamino]-2-(4-methanesulfonylpiperazin-1-yl)propanoic acid are obtained in the form of a white solid.

4.3: (S)-3-[(4-Benzyloxybenzenesulfonyl)methylamino]-N-hydroxy-2-(4-methanesulfonylpiperazin-1-yl)propionamide In a manner analogous to example 3.8, using 720 mg (1.4 mmol) of (S)-3-[(4-benzyloxybenzenesulfonyl)methylamino]-2-(4-methanesulfonylpiperazin-1-yl)propanoic acid, 360 mg (49%) of (S)-3-[(4-benzyloxybenzenesulfonyl)methylamino]-N-hydroxy-2-(4-methanesulfonylpiperazin-1-yl)propionamide are obtained in the form of a white solid with a melting point of 110° C.

¹H NMR (δ, DMSO): 2.58-2.63 (m, 2H); 2.65 (s, 3H); 2.67-2.73 (m, 2H); 2.86 (s, 3H); 2.98-3.05 (m, 4H); 3.05-3.09 (m, 1H); 3.24-3.25 (m, 1H); 3.28-3.31 (m, 1H); 5.21 (s, 2H); 7.24 (d, J=8.9 Hz, 2H); 7.34-7.44 (m, 3H); 7.48 (d, J=7.2 Hz, 2H); 7.72 (d, J=8.9 Hz, 2H); 8.99 (s, 1H); 10.69 (s, 1H).

Example 5

(S)-N-Hydroxy-2-(4-methanesulfonylpiperazin-1-yl)-3-[4-(2-methylquinolin-4-ylmethoxy)benzenesulfonylamino]propionamide 5.1: Methyl (S)-3-(4-hydroxybenzenesulfonylamino)-2-(4-methanesulfonylpiperazin-1-yl)propanoate A solution of 2.0 g (3.9 mmol) of methyl (S)-3-(4-benzyloxybenzenesulfonylamino)-2-(4-methanesulfonylpiperazin-1-yl)propanoate (prepared as described in example 3.6) in 60 ml of ethanol, 30 ml of dioxane and 0.5 ml of glacial acetic acid is degassed under a nitrogen stream and then 200 mg (10% by weight) of palladium-on-carbon at 10% in suspension in 3 ml of dioxane are added. The reaction medium is placed under a hydrogen atmosphere and stirred at ambient temperature for 18 h. After filtration through celite, the filtrate is hydrolyzed and then the product is extracted with ethyl acetate. The organic phase is washed with water and then with a saturated aqueous solution of sodium chloride, dried over magnesium sulfate, filtered and concentrated under vacuum. 1.65 g (100%) of methyl (S)-3-(4-hydroxybenzenesulfonylamino)-2-(4-methanesulfonylpiperazin-1-yl)propanoate are obtained in the form of a white solid.

5.2: Methyl (S)-2-(4-methanesulfonylpiperazin-1-yl)-3-[4-(2-methylquinolin-4-ylmethoxy)benzenesulfonylamino]propanoate 280 mg (0.85 mmol) of cesium carbonate followed by 160 mg (0.85 mmol) of 4-chloromethyl-2-methylquinoline and by 15 mg of potassium iodide are added to a solution of 300 mg (0.71 mmol) of methyl (S)-3-(4-hydroxybenzenesulfonylamino)-2-(4-methanesulfonylpiperazin-1-yl)propanoate in 10 ml of acetone. The reaction medium is stirred at ambient temperature for 18 h, filtered and concentrated under vacuum. The crude product is purified by chromatography on silica gel, elution being carried out with a 40/60 heptane/ethyl acetate mixture. 130 mg (32%) of methyl (S)-2-(4-methanesulfonylpiperazin-1-yl)-3-[4-(2-methylquinolin-4-ylmethoxy)benzenesulfonylamino]propanoate are obtained in the form of a white solid.

5.3: (S)-2-(4-Methanesulfonylpiperazin-1-yl)-3-[4-(2-methylquinolin-4-ylmethoxy)benzenesulfonylamino]propanoic Acid In a manner analogous to example 3.7, using 130 mg (0.2 mmol) of methyl (S)-2-(4-methanesulfonyl-piperidin-1-yl)-3-[4-(2-methylquinolin-4-ylmethoxy)benzenesulfonylamino]propanoate, 120 mg (99%) of (S)-2-(4-methanesulfonylpiperidin-1-yl)-3-[4-(2-methylquinolin-4-ylmethoxy)benzenesulfonylamino]-propanoic acid are obtained in the form of a white solid.

5.4: (S)-N-Hydroxy-2-(4-methanesulfonylpiperazin-1-yl)-3-[4-(2-methylquinolin-4-ylmethoxy)benzenesulfonylamino]propionamide In a manner analogous to example 3.8, using 123 mg (0.2 mmol) of (S)-2-(4-methanesulfonylpiperazin-1-yl)-3-[4-(2-methylquinolin-4-ylmethoxy)benzenesulfonylamino]propanoic acid, 90 mg (69%) of (S)-N-hydroxy-2-(4-methanesulfonylpiperazin-1-yl)-3-[4-(2-methylquinolin-4-ylmethoxy)benzenesulfonylamino]propionamide are obtained in the form of a solid with a melting point of 185° C.

¹H NMR (δ, DMSO): 2.54-2.60 (m, 4H); 2.72 (s, 3H); 2.88 (s, 3H), 2.88-2.93 (m, 1H); 3.01-3.05 (m, 1H); 3.06-3.12 (m, 4H); 3.13-3.16 (t, J=7 Hz, 1H); 5.76 (s, 2H); 7.38 (d, J=8 Hz, 2H); 7.57 (s, 1H); 7.61-7.66 (m, 2H); 7.78-7.85 (m, 3H); 8.02 (d, J=8.2 Hz, 1H); 8.15 (d, J=8.2 Hz, 1H); 8.98 (s, 1H); 10.71 (s, 1H).

Example 6

(S)-N-Hydroxy-2-(4-methanesulfonylpiperazin-1-yl)-3-[4-(naphthalen-1-ylmethoxy)benzenesulfonylamino]propionamide 6.1: Methyl (S)-2-(4-methanesulfonylpiperazin-1-yl)-3-[4-(2-methylquinolin-4-ylmethoxy)benzenesulfonylamino]propanoate In a manner analogous to example 5.2, using 160 mg (0.9 mmol) of 4-chloromethyl-2-methylquinoline and 300 mg (0.7 mmol) of methyl (S)-3-(4-hydroxy-benzenesulfonylamino)-2-(4-methanesulfonylpiperazin-1-yl)propanoate (prepared as described in 5.1), 130 mg (32%) of methyl (S)-2-(4-methanesulfonylpiperazin-1-yl)-3-[4-(2-methylquinolin-4-ylmethoxy)benzenesulfonylamino]propanoate are obtained in the form of a white solid.

6.2: (S)-2-(4-Methanesulfonylpiperazin-1-yl)-3-[4-(naphthalen-1-ylmethoxy)benzenesulfonylamino]propanoic Acid In a manner analogous to example 3.7, using 240 mg (0.6 mmol) of methyl (S)-2-(4-methanesulfonylpiperazin-1-yl)-3-[4-(naphthalen-1-ylmethoxy)benzenesulfonylamino]propanoate, 210 mg (91%) of (S)-2-(4-methanesulfonylpiperazin-1-yl)-3-[4-(naphthalen-1-ylmethoxy)benzenesulfonylamino]-propanoic acid are obtained in the form of a white solid.

6.3: (S)—N-Hydroxy-2-(4-methanesulfonylpiperazin-1-yl)-3-[4-(naphthalen-1-ylmethoxy)benzenesulfonylamino]propionamide In a manner analogous to example 3.8, using 210 mg (0.4 mmol) of (S)-2-(4-methanesulfonylpiperazin-1-yl)-3-[4-(naphthalen-1-ylmethoxy)benzenesulfonylamino]propanoic acid, 70 mg (33%) of (S)-N-hydroxy-2-(4-methanesulfonylpiperazin-1-yl)-3-[4-(naphthalen-1-ylmethoxy)benzenesulfonylamino]propionamide are obtained in the form of a beige solid with a melting point of 148° C.

¹H NMR (δ, DMSO): 2.45 (m, 2H); 2.60 (m, 2H); 2.85 (s, 3H); 2.90-3.05 (m, 4H); 3.06-3.15 (m, 2H); 3.35 (s, 1H); 5.66 (s, 2H); 7.30 (d, J=8.4 Hz, 2H); 7.50-7.60 (m, 4H); 7.70 (d, J=6.2 Hz, 1H); 7.77 (d, J=8.2 Hz, 2H); 7.95-8.05 (m, 2H); 8.10 (d, J=6.4 Hz, 1H); 8.94 (s, 1H); 10.70 (s, 1H).

Example 7

(S)-N-Hydroxy-2-(4-methanesulfonylpiperazin-1-yl)-3-(4-propoxybenzenesulfonylamino)propionamide 7.1: Methyl (S)-2-(4-methanesulfonylpiperazin-1-yl)-3-(4-propoxybenzenesulfonylamino)propanoate In a manner analogous to example 5.2, using 0.1 ml (1.3 mmol) of 1-bromopropane and 400 mg (0.95 mmol) of methyl (S)-3-(4-hydroxybenzenesulfonylamino)-2-(4-methanesulfonylpiperazin-1-yl)propanoate (prepared as described in 5.1), 220 mg (50%) of methyl (S)-2-(4-methanesulfonylpiperazin-1-yl)-3-(4-propoxybenzenesulfonylamino)propanoate are obtained in the form of a colorless oil.

7.2: (S)-2-(4-Methanesulfonylpiperazin-1-yl)-3-(4-propoxybenzenesulfonylamino)propanoic Acid In a manner analogous to example 3.7, using 220 mg (0.5 mmol) of methyl (S)-2-(4-methanesulfonylpiperazin-1-yl)-3-(4-propoxybenzenesulfonylamino)propanoate, 190 mg (90%) of (S)-2-(4-methanesulfonylpiperazin-1-yl)-3-(4-propoxybenzenesulfonylamino)propanoic acid are obtained in the form of a white solid.

7.3: (S)-N-Hydroxy-2-(4-methanesulfonylpiperazin-1-yl)-3-(4-propoxybenzenesulfonylamino)propionamide In a manner analogous to example 3.8, using 190 mg (0.4 mmol) of (S)-2-(4-methanesulfonylpiperazin-1-yl)-3-(4-propoxybenzenesulfonylamino)propanoic acid, 30 mg (16%) of (S)-N-hydroxy-2-(4-methanesulfonylpiperazin-1-yl)-3-(4-propoxybenzenesulfonylamino)propionamide are obtained in the form of a white solid with a melting point of 137° C.

$^1$H NMR ($\delta$, DMSO): 0.91 (t, J=7.3 Hz, 3H); 1.63-1.73 (m, 2H); 2.45 (m, 2H); 2.55 (m, 2H); 2.77 (s, 3H); 2.82 (m, 1H); 2.83-2.95 (m, 4H); 2.95-3.05 (m, 2H); 3.94 (t, J=6.4 Hz, 2H); 7.03 (d, J=8.7 Hz, 2H); 7.38 (m, 1H); 7.65 (d, J=8.7 Hz, 2H); 8.85 (s, 1H); 10.58 (s, 1H).

Example 8

(S)-3-[4-(3-Cyanobenzyloxy)benzenesulfonylamino]-N-hydroxy-2-(4-methanesulfonylpiperazin-1-yl)propionamide

8.1: Methyl (S)-3-[4-(3-cyanobenzyloxy)benzenesulfonylamino]-2-(4-methanesulfonylpiperazin-1-yl)propanoate In a manner analogous to example 5.2, using 205 mg (1 mmol) of 3-(bromomethyl)benzonitrile and 400 mg (0.95 mmol) of methyl (S)-3-(4-hydroxybenzenesulfonylamino)-2-(4-methanesulfonylpiperazin-1-yl)propanoate (prepared as described in example 5.1), 295 mg (58%) of methyl (S)-3-[4-(3-cyanobenzyloxy)benzenesulfonylamino]-2-(4-methanesulfonylpiperazin-1-yl)propanoate are obtained in the form of a white solid.

8.2: (S)-3-[4-(3-Cyanobenzyloxy)benzenesulfonylamino]-2-(4-methanesulfonylpiperazin-1-yl)propanoic Acid In a manner analogous to example 3.7, using 295 mg (0.5 mmol) of methyl (S)-3-[4-(3-cyanobenzyloxy)benzenesulfonylamino]-2-(4-methanesulfonylpiperazin-1-yl)propanoate, 270 mg (94%) of (S)-3-[4-(3-cyanobenzyloxy)benzenesulfonylamino]-2-(4-methanesulfonylpiperazin-1-yl)propanoic acid are obtained in the form of a white solid.

8.3: (S)-3-[4-(4-Cyanobenzyloxy)benzenesulfonylamino]-N-hydroxy-2-(4-methanesulfonylpiperazin-1-yl)propionamide In a manner analogous to example 3.8, using 264 mg (0.5 mmol) of (S)-3-[4-(3-cyanobenzyloxy)benzenesulfonylamino]-2-(4-methanesulfonylpiperazin-1-yl)propanoic acid, 107 mg (40%) of (S)-3-[4-(3-cyanobenzyloxy)benzenesulfonylamino]-N-hydroxy-2-(4-methanesulfonylpiperazin-1-yl)propionamide are obtained in the form of a beige powder with a melting point of 108° C.

$^1$H NMR ($\delta$, DMSO): 2.55 (m, 4H); 2.84 (s, 3H); 2.95-3.05 (m, 4H); 3.10 (t, J=6.4 Hz, 1H); 3.34 (m; 2H); 5.26 (s, 2H); 7.22 (d, J=8.6 Hz, 2H); 7.50 (s, 1H); 7.64 (t, J=7.6 Hz, 1H); 7.76 (d, J=8.6 Hz, 2H); 7.83 (t, J=8 Hz, 2H); 7.96 (s, 1H); 8.93 (s, 1H); 10.66 (s, 1H).

Example 9

(S)-3-[4-(4-Cyanobenzyloxy)benzenesulfonylamino] N-hydroxy-2-(4-methanesulfonylpiperazin-1-yl) propionamide

9.1: Methyl (S)-3-[4-(4-cyanobenzyloxy)benzenesulfonylamino]-2-(4-methanesulfonylpiperazin-1-yl) propanoate In a manner analogous to example 5.2, using 400 mg (1 mmol) of methyl (S)-3-(4-hydroxybenzenesulfonylamino)-2-(4-methanesulfonylpiperazin-1-yl)propanoate (prepared as described in 5.1) and 205 mg (1.1 mmol) of 4-(bromomethyl)benzonitrile, 229 mg (45%) of methyl (S)-3-[4-(4-cyanobenzyloxy)benzenesulfonylamino]-2-(4-methanesulfonylpiperazin-1-yl)propanoate are obtained in the form of a white solid.

9.2: (S)-3-[4-(4-Cyanobenzyloxy)benzenesulfonylamino]-2-(4-methanesulfonylpiperazin-1-yl)propanoic Acid In a manner analogous to example 3.7, using 229 mg (0.4 mmol) of methyl (S)-3-[4-(4-cyanobenzyloxy)benzenesulfonylamino]-2-(4-methanesulfonylpiperazin-1-yl)propanoate, 202 mg (91%) (S)-3-[4-(4-cyanobenzyloxy)benzenesulfonylamino]-2-(4-methanesulfonylpiperazin-1-yl)propanoic acid are obtained in the form of a white solid.

9.3: (S)-3-[4-(4-Cyanobenzyloxy)benzenesulfonylamino]-N-hydroxy-2-(4-methanesulfonylpiperazin-1-yl)propionamide In a manner analogous to example 3.8, using 197 mg (0.4 mmol) of (S)-3-[4-(4-cyanobenzyloxy)benzenesulfonylamino]-2-(4-methanesulfonylpiperazin-1-yl)-propanoic acid, 81 mg (40%) of (S)-3-[4-(4-cyanobenzyloxy)benzenesulfonylamino]-N-hydroxy-2-(4-methanesulfonylpiperazin-1-yl)propionamide are obtained in the form of a beige powder with a melting point of 109° C.

$^1$H NMR ($\delta$, DMSO): 2.50-2.60 (m, 4H); 2.84 (s, 3H); 2.96-3.01 (m, 4H); 3.09 (t, J=7 Hz, 1H); 3.34 (s, 2H); 5.32 (s, 2H); 7.22 (d, J=8.8 Hz, 2H); 7.50 (m, 1H); 7.66 (d, J=8.1 Hz, 2H); 7.75 (d, J=8.8 Hz, 2H); 7.89 (d, J=8.1 Hz, 2H); 8.93 (s, 1H); 10.66 (s, 1H).

Example 10

Benzyl 4-{(S)-1-hydroxycarbamoyl-2-[4-(2-methylquinolin-4-ylmethoxy)benzenesulfonylamino] ethyl}piperazine-1-carboxylate

10.1: Benzyl bis(2-chloroethyl)carbamate 13.2 ml (92 mmol) of benzyl chloroformate are added slowly to a solution, cooled to 0° C., of 15 g (84 mmol) of bis(2-chloroethylamine) hydrochloride, 26 ml (185 mmol) of triethylamine in 200 ml of dichloromethane and 70 ml of tetrahydrofuran, stirred beforehand for 15 min and then filtered in order to remove the triethylammonium chloride. The reaction medium is stirred at ambient temperature for 18 h. After the addition of water, the reaction medium is extracted with ethyl acetate. The organic phase is dried over magnesium sulfate, filtered and evaporated. 20 g of crude residue are obtained and purified by chromatography on silica gel, elution being carried out with an 8/2 heptane/ethyl acetate mixture. 6 g (26%) of benzyl bis(2-chloroethyl)carbamate are thus obtained.

10.2: Benzyl 4-((S)-2-tert-butoxycarbonylamino-1-methoxycarbonylethyl)piperazine-1-carboxylate A solution of 5.5 g (20 mmol) of benzyl bis(2-chloroethyl) carbamate and 5.1 g (20 mmol) of methyl 2-amino-3-tert-butoxypropanoate hydrochloride in 40 ml of diisopropylethylamine is heated at 127° C. for 18 h. After cooling, the reaction medium is evaporated to dryness. 17 g of crude residue are obtained and purified by chromatography on silica gel, elution being carried out with a 9/1 up to 4/6 heptane/ethyl acetate mixture. 1.6 g (19%) of benzyl 4-((S)-2-tert-butoxycarbonylamino-1-methoxycarbonylethyl)piperazine-1-carboxylate.

10.3: Benzyl 4-(2-amino-1-methoxycarbonylethyl) piperazine-1-carboxylate Dihydrochloride A solution of 1.45 g (3.4 mmol) of benzyl 4-((S)-2-tert-butoxycarbonylamino-1-methoxycarbonylethyl)piperazine-1-carboxylate in 3.5 ml of a solution of hydrochloric acid in isopropanol, having a concentration 5-6N, and 10 ml of methanol is heated at 40° C. for 3 h and then evaporated. The residue is taken up in diethyl ether and filtered. 1.2 g (90%) of benzyl 4-(2-amino-1-methoxycarbonylethyl)piperazine-1-carboxylate dihydrochloride are obtained in the form of a solid.

10.4: Benzyl 4-[(S)-2-(4-hydroxybenzenesulfonylamino)-1-methoxycarbonylethyl]piperazine-1-carboxylate 2.1 ml (15 mmol) of triethylamine and then 920 mg (5 mmol) of 4-hydroxybenzenesulfonyl chloride in 20 ml of dichloromethane are added dropwise to a solution of 1.1 g (3 mmol) of benzyl 4-(2-amino-1-methoxycarbonylethyl)piperazine-1-carboxylate dihydrochloride in 30 ml of dichloromethane, cooled beforehand to 0° C. The reaction medium is then stirred at ambient temperature for 18 h. After the addition of water, the reaction medium is extracted with dichloromethane. The organic phase is with water and then dried over magnesium sulfate, filtered and concentrated under vacuum. The crude residue obtained is purified by chromatography on silica gel, elution being carried out with a 50/50 heptane/ethyl acetate mixture. 60 mg (46%) of benzyl 4-[2-(4-hydroxybenzenesulfonylamino)-1-methoxycarbonylethyl]piperazine-1-carboxylate are obtained in the form of a white solid.

10.5: Benzyl 4-{(S)-1-methoxycarbonyl-2-[4-(2-methylquinolin-4-ylmethoxy)benzenesulfonylamino] ethyl}piperazine-1-carboxylate In a manner analogous to example 5.2, using 260 mg (1.4 mmol) of 4-chloromethyl-2-methylquinoline and 600 mg (1.3 mmol) of benzyl 4-[(S)-2-(4-hydroxybenzenesulfonylamino)-1-methoxycarbonylethyl]piperazine-1-carboxylate, 320 mg (40%) of benzyl 4-{(S)-1-methoxycarbonyl-2-[4-(2-methylquinolin-4-ylmethoxy)benzenesulfonylamino] ethyl}piperazine-1-carboxylate are obtained in the form of a white solid.

10.6: Benzyl 4-{(S)-1-carboxy-2-[4-(2-methylquinolin-4-ylmethoxybenzenesulfonylamino] ethyl}piperazine-1-carboxylate In a manner analogous to example 3.7, using 160 mg (0.25 mmol) of benzyl 4-{(S)-1-methoxycarbonyl-2-[4-(2-methylquinolin-4-ylmethoxy)benzenesulfonylamino] ethyl}piperazine-1-carboxylate, 135 mg (87%) of benzyl 4-{(S)-1-carboxy-2-[4-(2-methylquinolin-4-ylmethoxybenzenesulfonylamino]ethyl}piperazine-1-carboxylate are obtained in the form of a beige solid.

10.7: Benzyl 4-{(S)-1-hydroxycarbamoyl-2-[4-(2-methylquinolin-4-ylmethoxy)benzenesulfonylamino] ethyl}piperazine-1-carboxylate In a manner analogous to example 3.8, using 135 mg (0.2 mmol) of benzyl 4-{(S)-1-carboxy-2-[4-(2-methylquinolin-4-ylmethoxybenzenesulfonylamino]ethyl}piperazine-1-carboxylate, 115 mg (82%) of benzyl 4-{(S)-1-hydroxycarbamoyl-2-[4-(2-methylquinolin-4-ylmethoxy) benzenesulfonylamino]ethyl}piperazine-1-carboxylate are obtained in the form of a white solid with a melting point of 162° C.

$^1$H NMR (δ, DMSO): 2.35-2.45 (m, 4H); 2.70 (s, 3H); 2.80-2.90 (m, 1H); 2.95-3.05 (m, 1H); 3.05-3.10 (m, 1H); 3.25-3.40 (m, 4H); 5.05 (s, 2H); 5.74 (s, 2H); 7.29-7.40 (m, 7H); 7.55 (m, 1H); 7.60-7.70 (m, 2H); 7.79 (d, J=8.8 Hz, 3H); 8.01 (d, J=8 Hz, 1H); 8.14 (d, J=8 Hz, 1H); 8.91 (s, 1H); 10.67 (s, 1H).

Example 11

(S)-N-Hydroxy-2-(4-methanesulfonylpiperazin-1-yl)-3-[4-(2-phenylpyridin-4-ylmethoxy)benzenesulfonylamino]propionamide 11.1: Methyl (S)-2-(4-methanesulfonylpiperazin-1-yl)-3-[4-(2-phenylpyridin-4-ylmethoxy)benzenesulfonylamino]propanoate 0.23 ml (1.4 mmol) of diethyl azodicarboxylate is added slowly to a solution of 400 mg (0.9 mmol) of methyl (S)-3-(4-hydroxybenzenesulfonylamino)-2-(4-methanesulfonylpiperazin-1-yl)propanoate (prepared as described in example 5.1), 193 mg (1.0 mmol) of (2-phenylpyridin-4-yl) methanol and 373 mg (1.4 mmol) of triphenylphosphine in 4 ml of tetrahydrofuran. The reaction mixture is stirred for one hour at ambient temperature and then evaporated to dryness. The residue obtained is purified by chromatography on silica gel, elution being carried out with a 60/40 heptane/ethyl acetate mixture. 318 mg (57%) of methyl (S)-2-(4-methanesulfonylpiperazin-1-yl)-3-[4-(2-phenylpyridin-4-ylmethoxy)-benzenesulfonylamino]propanoate are obtained in the form of a white powder.

11.2: (S)-2-(4-Methanesulfonylpiperazin-1-yl)-3-[4-(2-phenylpyridin-4-ylmethoxy)benzenesulfonylamino]propanoic Acid In a manner analogous to example 3.7, using 317 mg (0.5 mmol) of methyl (S)-2-(4-methanesulfonylpiperazin-1-yl)-

3-[4-(2-phenylpyridin-4-ylmethoxy)benzenesulfonylamino]propanoate, 298 mg (96%) of (S)-2-(4-methanesulfonylpiperazin-1-yl)-3-[4-(2-phenylpyridin-4-ylmethoxy)benzenesulfonylamino]propanoic acid are obtained in the form of a white solid.

11.3: (S)-N-Hydroxy-2-(4-methanesulfonylpiperazin-1-yl)-3-[4-(2-phenylpyridin-4-ylmethoxy)benzenesulfonylamino]propionamide In a manner analogous to example 3.8, using 293 mg (0.5 mmol) of (S)-2-(4-methanesulfonylpiperazin-1-yl)-3-[4-(2-phenylpyridin-4-ylmethoxy)benzenesulfonylamino]propanoic acid, 64 mg (21%) of (S)—N-hydroxy-2-(4-methanesulfonylpiperazin-1-yl)-3-[4-(2-phenylpyridin-4-ylmethoxy)benzenesulfonylamino]propionamide are obtained in the form of a white powder with a melting point of 100° C.

$^1$H NMR (δ, DMSO): 2.52-2.59 (m, 4H); 2.84 (s, 3H); 2.85-2.90 (m, 1H); 2.90-3.00 (m, 1H); 3.00-3.08 (m, 4H); 3.10 (t, J=7.0 Hz, 1H); 5.35 (s, 2H); 7.26 (d, J=8.9 Hz, 2H); 7.42 (m, 1H); 7.45-7.55 (m, 4H); 7.78 (d, J=8.8 Hz, 2H); 8.03 (s, 1H); 8.10 (d, J=7.0 Hz, 2H); 8.69 (d, J=5.0 Hz, 1H); 8.93 (s, 1H); 10.66 (s, 1H).

Example 12

(R)-N-Hydroxy-2-(4-methanesulfonylpiperazin-1-yl)-3-[4-(2-methylquinolin-4-ylmethoxy)benzenesulfonylamino]propionamide

12.1: Methyl (R)-3-tert-butoxycarbonylamino-2-(4-methanesulfonylpiperazin-1-yl)propanoate In a manner analogous to example 3.2, using 3.8 g (17 mmol) of N,N-bis(2-chloroethyl)-methanesulfonamide (prepared as described in 3.1) and 4 g (16 mmol) of commercial methyl (R)-2-amino-3-tert-butoxypropanoate hydrochloride, 2.6 g (46%) of methyl (R)-3-tert-butoxycarbonylamino-2-(4-methanesulfonylpiperazin-1-yl)propanoate are obtained in the form of a light yellow solid.

12.2: Methyl (R)-3-amino-2-(4-methanesulfonylpiperazin-1-yl)propanoate Dihydrochloride In a manner analogous to example 3.3, using 2.5 g (7 mmol) of methyl (R)-3-tert-butoxycarbonylamino-2-(4-methanesulfonylpiperazin-1-yl)propanoate, 2.3 g (100%) of methyl (R)-3-amino-2-(4-methanesulfonylpiperazin-1-yl)propanoate are obtained.

12.3: Methyl (R)-3-(4-benzyloxybenzenesulfonylamino)-2-(4-methanesulfonylpiperazin-1-yl)propanoate In a manner analogous to example 3.6, using 2.4 g (8.4 mmol) of 4-benzyloxybenzenesulfonyl chloride (prepared as described in example 3.5) and 2.3 g (7.6 mmol) of methyl (R)-3-amino-2-(4-methanesulfonylpiperazin-1-yl)propanoate dihydrochloride, 3 g (77%) of methyl (R)-3-(4-benzyloxybenzenesulfonylamino)-2-(4-methanesulfonylpiperazin-1-yl)propanoate are obtained in the form of a solid.

12.4: Methyl (R)-3-(4-hydroxybenzenesulfonylamino)-2-(4-methanesulfonylpiperazin-1-yl)propanoate In a manner analogous to example 5.1, using 3 g (5.9 mmol) of methyl (R)-3-(4-benzyloxybenzenesulfonylamino)-2-(4-methanesulfonylpiperazin-1-yl)propanoate, 2 g (80%) of methyl (R)-3-(4-hydroxybenzenesulfonylamino)-2-(4-methanesulfonylpiperazin-1-yl)propanoate are obtained in the form of a white solid.

12.5: Methyl (R)-2-(4-methanesulfonylpiperazin-1-yl)-3-[4-(2-methylquinolin-4-ylmeth-oxy)benzenesulfonylamino]propanoate In a manner analogous to example 5.2, using 1 g (2.4 mmol) of methyl (R)-3-(4-hydroxy-benzenesulfonylamino)-2-(4-methanesulfonylpiperazin-1-yl)propanoate and 500 mg (2.6 mmol) of 4-chloromethyl-2-methylquinoline, 740 mg (53%) of methyl (R)-2-(4-methanesulfonylpiperazin-1-yl)-3-[4-(2-methylquinolin-4-ylmethoxy)benzenesulfonylamino]propanoate are obtained in the form of a solid.

12.6: (R)-2-(4-Methanesulfonylpiperazin-1-yl)-3-[4-(2-methylquinolin-4-ylmethoxy)benzenesulfonylamino]propanoic acid In a manner analogous to example 3.7, using 740 mg (1.3 mmol) of methyl (R)-2-(4-methanesulfonylpiperazin-1-yl)-3-[4-(2-methylquinolin-4-ylmethoxy)benzenesulfonylamino]propanoate, 622 mg (86%) of (R)-2-(4-methanesulfonylpiperazin-1-yl)-3-[4-(2-methylquinolin-4-ylmethoxy)-benzenesulfonylamino]propanoic acid are obtained.

12.7: (R)-N-Hydroxy-2-(4-methanesulfonylpiperazin-1-yl)-3-[4-(2-methylquinolin-4-ylmethoxy)benzenesulfonylamino]propionamide In a manner analogous to example 3.8, using 620 mg (1.1 mmol) of (R)-2-(4-methanesulfonylpiperazin-1-yl)-3-[4-(2-methylquinolin-4-ylmethoxy)benzenesulfonylamino]propanoic acid, 465 mg (73%) of (R)-N-hydroxy-2-(4-methanesulfonylpiperazin-1-yl)-3-[4-(2-methylquinolin-4-ylmethoxy)benzenesulfonylamino]propionamide are obtained in the form of a white solid.

$^1$H NMR (δ, DMSO): 2.53 (m, 4H); 2.68 (s, 3H); 2.84 (s, 3H); 2.85 (m, 2H); 2.95-3.05 (m, 4H); 3.10 (m, 1H); 5.72 (s, 2H); 7.35 (d, J=8.8 Hz, 2H); 7.52 (m, 1H); 7.57-7.62 (m, 2H); 7.75-7.82 (m, 3H); 7.98 (d, J=8.4 Hz, 1H); 8.11 (d, J=8.16 Hz, 1H); 8.93 (s, 1H); 10.70 (s, 1H).

Example 13

(S)-N-Hydroxy-3-[4-(2-methylquinolin-4-ylmethoxy)benzenesulfonylamino]-2-piperazin-1-yl-propionamide

13.1: Benzyl 4-{(S)-1-hydroxycarbamoyl-2-[4-(2-methylquinolin-4-ylmethoxy)benzenesulfonylamino]ethyl}piperazine-1-carboxylate In a manner analogous to example 3.8, using 135 mg (0.2 mmol) of benzyl 4-{(S)-1-carboxy-2-[4-(2-methylquinolin-4-ylmethoxybenzenesulfonylamino]ethyl}piperazine-1-carboxylate (prepared as described in 10.6), 115 mg (82%) of benzyl 4-{(S)-1-hydroxycarbamoyl-2-[4-(2-methylquinolin-4-ylmethoxy)benzenesulfonylamino]ethyl}piperazine-1-carboxylate are obtained in the form of a white solid with a melting point of 162° C.

13.2: (S)-N-Hydroxy-3-[4-(2-methylquinolin-4-yl-methoxy)benzenesulfonylamino]-2-piperazin-1-yl-propionamide 90 mg (0.15 mmol) of benzyl 4-{(S)-1-hydroxycarbamoyl-2-[4-(2-methylquinolin-4-ylmethoxy)benzenesulfonylamino]ethyl}piperazine-1-carboxylate are placed in solution in 5 ml of dichloromethane and 5 ml of trifluoroacetic acid. The reaction medium is then stirred at ambient temperature for 96 h. After evaporation of the trifluoroacetic acid, the residue is taken up with 5 ml of saturated aqueous solution of sodium hydrogen carbonate and extracted with n-butanol. The organic phase is washed with water and then with a saturated aqueous solution of sodium chloride, dried over magnesium sulfate, filtered and concentrated under vacuum. The crude product obtained is taken up in a 50/50 heptane/ethyl acetate mixture, stirred for 1 h and then filtered and dried under vacuum. 50 mg (70%) of (S)-N-hydroxy-3-[4-(2-methylquinolin-4-ylmethoxy)benzenesulfonylamino]-2-piperazin-1-ylpropionamide are obtained in the form of a beige solid with a melting point of 225° C.

$^1$H NMR (δ, DMSO): 2.35-2.45 (m, 4H); 2.67 (s, 3H); 2.70 (m, 4H); 2.80-3.00 (m, 2H); 3.15 (s, 1H); 5.72 (s, 2H); 7.35 (d, J=8.6 Hz, 2H); 7.70-7.80 (m, 3H); 7.98 (d, J=8.4 Hz, 1H); 8.12 (d, J=8.2 Hz, 1H).

Example 14

(S)-N-Hydroxy-2-(4-methanesulfonylpiperazin-1-yl)-3-[4-(2-methylquinolin-4-ylmethoxy)benzenesulfonylamino]propionamide hydrochloride 0.2 ml (1.3 mmol) of a solution of hydrochloric acid in isopropanol having a concentration of 5-6N is added to a solution of 301 mg (0.5 mmol) of (S)-N-hydroxy-2-(4-methanesulfonylpiperazin-1-yl)-3-[4-(2-methylquinolin-4-ylmethoxy)benzenesulfonylamino]propionamide (prepared as described in example 14) in 10 ml of isopropanol. After stirring at ambient temperature for 1 h, the product precipitates. Through filtration, 927 mg of (S)-N-hydroxy-2-(4-methanesulfonylpiperazin-1-yl)-3-[4-(2-methylquinolin-4-ylmethoxy)benzenesulfonylamino]propionamide hydrochloride are obtained in the form of a white powder. This solid is recrystallized from a 30 ml/5 ml isopropanol/water mixture. 176 mg (52%) of (S)—N-hydroxy-2-(4-methanesulfonylpiperazin-1-yl)-3-[4-(2-methylquinolin-4-ylmethoxy)benzenesulfonylamino]propionamide are obtained in the form of a white powder with a melting point of 209° C.

$^1$H NMR (δ, DMSO): 2.67 (m, 4H); 2.87 (s, 3H); 2.93 (s, 3H); 3.00-3.15 (m, 4H); 3.22 (m, 1H); 3.35-3.90 (m, 2H); 5.94 (s, 2H); 7.42 (d, J=8.7 Hz, 2H); 7.64 (m, 1H); 7.83-7.90 (m, 3H); 7.98 (m, 1H); 8.05 (m, 1H); 8.30 (d, J=7.6 Hz, 1H); 8.38 (d, J=8.5 Hz, 1H); 9.00 (m, 1H); 10.75 (m, 1H).

Example 15 tert-Butyl 3-{4-[(S)-2-hydroxycarbamoyl-2-(4-methanesulfonylpiperazin-1-yl)ethylsulfamoyl]phenoxymethyl}-2-methylindole-1-carboxylate di(trifluoroacetate)

15.1: tert-Butyl 3-{4-[(S)-2-(4-methanesulfonylpiperazin-1-yl)-2-methoxycarbonylethylsulfamoyl]phenoxymethyl}-2-methylindole-1-carboxylate In a manner analogous to example 11.1, using 400 mg (0.95 mmol) of methyl (S)-3-(4-hydroxybenzenesulfonylamino)-2-(4-methanesulfonylpiperazin-1-yl)propanoate (prepared as described in example 5.1) and 248 mg (0.95 mmol) of commercial tert-butyl 3-hydroxymethyl-2-methylindole-1-carboxylate, 326 mg (52%) of tert-butyl 3-{4-[(S)-2-(4-methanesulfonylpiperazin-1-yl)-2-methoxycarbonylethylsulfamoyl]phenoxymethyl}-2-methylindole-1-carboxylate are obtained in the form of a beige powder.

15.2: tert-Butyl 3-{4-[(S)-2-carboxy-2-(4-methanesulfonylpiperazin-1-yl)-ethylsulfamoyl]phenoxymethyl}-2-methylindole-1-carboxylate In a manner analogous to example 3.7, using 325 mg (0.5 mmol) of tert-butyl 3-{4-[(S)-2-(4-methanesulfonylpiperazin-1-yl)-2-methoxycarbonylethylsulfamoyl]phenoxymethyl}-2-methylindole-1-carboxylate, 179 mg (100%) of tert-butyl 3-{4-[(S)-2-carboxy-2-(4-methanesulfonylpiperazin-1-yl)ethylsulfamoyl]phenoxymethyl}-2-methylindole-1-carboxylate are obtained in the form of a yellow powder.

15.3: tert-Butyl 3-{4-[(S)-2-hydroxycarbamoyl-2-(4-methanesulfonylpiperazin-1-yl)ethylsulfamoyl]phenoxymethyl}-2-methylindole-1-carboxylate di(trifluoroacetate)

45 mg (0.3 mmol) of O-tert-butyldimethylsilylhydroxylamine in solution in 1 ml of dimethylformamide are added to a solution of 179 mg (0.3 mmol) of tert-butyl 3-{4-[(S)-2-carboxy-2-(4-methanesulfonylpiperazin-1-yl)ethylsulfamoyl]phenoxymethyl}-2-methylindole-1-carboxylate, 41 mg (0.3 mmol) of 1-hydroxybenzotriazole and 58 mg (0.3 mmol) of 1-ethyl-3-(3-dimethylaminopropyl)carbodiimide hydrochloride in 3 ml of dimethylformamide. The reaction mixture is stirred at ambient temperature for 18 h. After the addition of water and then extraction with ethyl acetate, the organic phases are combined, washed with a saturated solution of sodium hydrogen carbonate and then dried over sodium sulfate, filtered and evaporated. The residue is purified by preparative HPLC (Gemini C6 phenyl column, 150×3 mm, 3 μm; UV detector: 190-420 nm; flow rate: 0.3 ml/mn; solvent A: CH$_3$CN+0.02% trifluoroacetic acid; solvent B: water+0.02% trifluoroacetic acid).
Gradient:

| Time | Composition | |
| --- | --- | --- |
| 0.0 min | A = 5% | B = 95% |
| 20.0 min | A = 98% | B = 2% |
| 30.0 min | A = 98% | B = 2% |

Retention time: 14.6 min, M+1=666.1.

After concentration of the various fractions, 21 mg (10%) of tert-butyl 3-{4-[(S)-2-hydroxycarbamoyl-2-(4-methanesulfonylpiperazin-1-yl)ethylsulfamoyl]phenoxymethyl}-2-methylindole-1-carboxylate di(trifluoroacetate) are obtained.

Example 16

(S)-N-Hydroxy-2-(4-methanesulfonylpiperazin-1-yl)-3-[4-(quinolin-4-ylmethoxy)benzenesulfonylamino]propionamide

16.1: Methyl (S)-2-(4-methanesulfonylpiperazin-1-yl)-3-[4-(quinolin-4-ylmethoxy)benzenesulfonylamino]propanoate In a manner analogous to example 5.2, using 440 mg (2.5 mmol) of 4-chloromethylquinoline and 950 mg (2.2 mmol) of methyl (S)-3-(4-hydroxybenzenesulfonylamino)-2-(4-methanesulfonylpiperazin-1-yl)propanoate (prepared as described in 5.1), 550 mg (43%) of methyl (S)-2-(4-methanesulfonylpiperazin-1-yl)-3-[4-(quinolin-4-ylmethoxy)benzenesulfonylamino]propanoate are obtained in the form of a colorless oil.

16.2: (S)-2-(4-Methanesulfonylpiperazin-1-34)-3-[4-(quinolin-4-ylmethoxy)benzenesulfonylamino]propanoic Acid In a manner analogous to example 3.7, using 550 mg (1.0 mmol) of methyl (S)-2-(4-methanesulfonylpiperazin-1-yl)-3-[4-(quinolin-4-ylmethoxy)benzenesulfonylamino]propanoate, 450 mg (83%) (S)-2-(4-methanesulfonylpiperazin-1-yl)-3-[4-(quinolin-4-ylmethoxy)benzenesulfonylamino]propanoic acid are obtained in the form of a white solid.

16.3: (S)-N-Hydroxy-2-(4-methanesulfonylpiperazin-1-yl)-3-[4-(quinolin-4-ylmethoxy)benzenesulfonylamino]propionamide In a manner analogous to example 3.8, using 450 mg (0.8 mmol) of (S)-2-(4-methanesulfonylpiperazin-1-yl)-3-[4-(quinolin-4-ylmethoxy)benzenesulfonylamino]propanoic acid, 260 mg (56%) of (S)—N-hydroxy-2-(4-methanesulfonylpiperazin-1-yl)-3-[4-(quinolin-4-ylmethoxy)benzenesulfonylamino]propionamide are obtained in the form of a white solid with a melting point of 180° C.
$^1$H NMR (δ, DMSO): 2.52-2.54 (m, 4H); 2.84 (s, 3H); 2.87 (m, 1H); 2.97 (m, 1H); 2.98-3.05 (m, 4H); 3.11 (t, J=7 Hz, 1H); 5.78 (s, 2H); 7.34 (d, J=8.8 Hz, 2H); 7.52 (m, 1H); 7.66-7.72 (m, 2H); 7.78-7.84 (m, 3H); 8.10 (d, J=8.3 Hz, 1H); 8.19 (d, J=8.2 Hz, 1H); 8.93 (s, 1H); 8.94 (s, 1H); 10.67 (s, 1H).

Example 17

(S)-2-(4-Benzylpiperazin-1-yl)-N-hydroxy-3-[4-(2-methylquinolin-4-ylmethoxy)benzenesulfonylamino]propionamide 17.1: Sodium Salt of 4-(2-methylquinolin-4-ylmethoxy)benzenesulfonic Acid 100 g (438 mmol) of 4-chloromethyl-2-methylquinoline hydrochloride are added to a solution of 77 g (395 mmol) of the sodium salt of 4-hydroxybenzenesulfonic acid and of 84 ml (84 mmol) of an aqueous solution of sodium hydroxide, having a concentration of 1M, in 800 ml of isopropanol. The reaction medium is heated at 70° C. for 5 h and then at 40° C. for 18 h.
After evaporation of the isopropanol, the product obtained is filtered, rinsed with isopropanol and with diethyl ether and then dried under vacuum. 114 g (75%) of the sodium salt of 4-(2-methylquinolin-4-ylmethoxy)benzenesulfonic acid are obtained in the form of a white solid.

17.2: 4-(2-Methylquinolin-4-ylmethoxy)benzenesulfonyl Chloride 76 g (216 mmol) of the sodium salt of 4-(2-methylquinolin-4-ylmethoxy)benzenesulfonic acid in 500 ml of dimethylformamide are added dropwise to a solution of 55 ml (649 mmol) of oxalyl chloride in 100 ml of dichloromethane, cooled beforehand to −10° C. After the addition, the reaction medium is stirred at ambient temperature for 18 h. The reaction medium is then poured into 1 l of ice and then extracted with ethyl acetate. The organic phases are combined, washed with water and then with a saturated aqueous solution of sodium chloride, dried over magnesium sulfate, filtered and concentrated under vacuum. 77 g (92%) of 4-(2-methylquinolin-4-ylmethoxy)benzenesulfonyl chloride hydrochloride are obtained in the form of a beige solid.

17.3: Benzylbis(2-chloroethyl)amine 21 g (152 mmol) of potassium carbonate and then 8 ml (67 mmol) of benzyl bromide are added to a solution of 10 g (56 mmol) of bis(2-chloroethyl)amine hydrochloride in 130 ml of acetonitrile, and then the reaction medium is heated at 60° C. for 24 h. After filtration, the filtrate is concentrated under vacuum. The crude residue is purified by chromatography on silica gel, elution being carried out with a 90/10 heptane/ethyl acetate mixture, to give 8.5 g (65%) of benzylbis(2-chloroethyl)amine.

17.4: Methyl (S)-2-(4-benzylpiperazin-1-yl)-3-tert-butoxycarbonylaminopropanoate A solution of 5.9 g (23 mmol) of commercial methyl (S)-2-amino-3-tert-butoxycarbonylaminopropanoate hydrochloride and of 9.6 g (23 mmol) of benzylbis(2-chloroethyl)amine in 50 ml of N,N-diisopropylethylamine is heated at 127° C. for 3 h 30. After evaporation of the N,N-diisopropylethylamine, the reaction medium is hydrolyzed and then extracted with ethyl acetate. The organic phase is washed with an aqueous solution of sodium hydroxide having a concentration of 1N, and with water, and then dried over magnesium sulfate, filtered and concentrated under vacuum. The crude product obtained is purified by chromatography on silica gel, elution being carried out with a 50/50 heptane/ethyl acetate mixture. 8.9 g (64%) of methyl (S)-2-(4-benzylpiperazin-1-yl)-3-tert-butoxycarbonylaminopropanoate are obtained in the form of a yellow oil.

17.5: Methyl (S)-3-amino-2-(4-benzylpiperazin-1-yl) propanoate Trihydrochloride 8.9 g (23.5 mmol) of methyl (S)-2-(4-benzylpiperazin-1-yl)-3-tert-butoxycarbonylaminopropanoate are placed in solution in 60 ml of methanol and in 20 ml of isopropanolic hydrochloric acid having a concentration of 5-6N. The reaction medium is stirred at 40° C. for 18 h and then concentrated under vacuum. 9.0 g (100%) of methyl (S)-3-amino-2-(4-benzylpiperazin-1-yl)propanoate trihydrochloride are obtained in the form of a beige solid.

17.6: Methyl (S)-2-(4-benzylpiperazin-1-yl)-3-[4-(2-methylquinolin-4-ylmethoxy)benzenesulfonylamino] propanoate In a manner analogous to example 3.6, using 1.0 g (2.6 mmol) of methyl (S)-3-amino-2-(4-benzylpiperazin-1-yl) propanoate trihydrochloride and 1.1 g (2.8 mmol) of 4-(2-methylquinolin-4-ylmethoxy)benzenesulfonyl chloride in hydrochloride form, 750 mg (50%) of methyl (S)-2-(4-benzylpiperazin-1-yl)-3-[4-(2-methylquinolin-4-ylmethoxy) benzenesulfonylamino]propanoate are obtained in the form a beige solid.

17.7: (S)-2-(4-Benzylpiperazin-1-yl)-3-[4-(2-methylquinolin-4-ylmethoxy)benzenesulfonylamino]propanoic Acid In a manner analogous to example 3.7, using 750 mg (1.3 mmol) of methyl (S)-2-(4-benzylpiperazin-1-yl)-3-[4-(2-methylquinolin-4-ylmethoxy)benzenesulfonylamino]propanoate, 680 mg (93%) of (S)-2-(4-benzylpiperazin-1-yl)-3-[4-(2-methylquinolin-4-ylmethoxy)benzenesulfonylamino]propanoic acid are obtained in the form of a white solid.

17.8: (S)-2-(4-Benzylpiperazin-1-yl)-N-hydroxy-3-[4-(2-methylquinolin-4-ylmethoxy)benzenesulfonylamino]propionamide In a manner analogous to example 3.8, using 680 mg (1.2 mmol) of (S)-2-(4-benzylpiperazin-1-yl)-3-[4-(2-methylquinolin-4-ylmethoxy)benzenesulfonylamino]propanoic acid, 250 mg (36%) of (S)-2-(4-benzylpiperazin-1-yl)-N-hydroxy-3-[4-(2-methylquinolin-4-ylmethoxy)benzenesulfonylamino]propionamide are obtained in the form of a white solid with a melting point of 188° C.
$^1$H NMR (δ, DMSO): 2.33 (m, 4H); 2.49 (m, 4H); 2.73 (s, 3H); 2.80-2.90 (m, 1H); 3.00-3.10 (m, 2H); 2.46 (m, 2H); 5.77 (s, 2H); 7.25-7.40 (m, 7H); 7.50 (m, 1H); 7.61-7.67 (m, 2H); 7.78-7.85 (m, 3H); 8.04 (d, J=8 Hz, 1H); 8.17 (d, J=8.2 Hz, 1H); 8.95 (s, 1H); 10.65 (s, 1H).

Example 18

(S)-2-[4-(4-Fluorobenzyl)piperazin-1-yl]-N-hydroxy-3-[4-(2-methylquinolin-4-ylmethoxy)benzenesulfonylamino]propionamide

18.1: Bis(2-chloroethyl)(4-fluorobenzyl)amine

In a manner analogous to example 17.3, using 5 g (28 mmol) of bis(2-chloroethyl)amine hydrochloride and 3.8 ml (31 mmol) of 1-bromomethyl-4-fluorobenzene, 6.9 g (98%) of bis(2-chloroethyl)(4-fluorobenzyl)amine are obtained.

18.2: Methyl (S)-3-tert-butoxycarbonylamino-2-[4-(4-fluorobenzyl)piperazin-1-yl]propanoate In a manner analogous to example 17.4, using 7.1 g (28 mmol) of methyl (S)-2-amino-3-tert-butoxycarbonylaminopropanoate hydrochloride and 6.9 g (28 mmol) of bis(2-chloroethyl)(4-fluorobenzyl)amine, 5.3 g (48%) of methyl (S)-3-tert-butoxycarbonylamino-2-[4-(4-fluorobenzyl)piperazin-1-yl]propanoate are obtained in the form of an oil.

18.3: Methyl (S)-3-amino-2-[4-(4-fluorobenzyl)piperazin-1-yl]propanoate trihydrochloride In a manner analogous to example 17.5, using 5.3 g (13.4 mmol) of methyl (S)-3-tert-butoxycarbonylamino-2-[4-(4-fluorobenzyl)piperazin-1-yl]propanoate, 5.4 g (100%) of methyl (S)-3-amino-2-[4-(4-fluorobenzyl)piperazin-1-yl]propanoate trihydrochloride are obtained in the form of a beige solid.

18.4: Methyl (S)-2-[4-(4-fluorobenzyl)piperazin-1-yl]-3-[4-(2-methylquinolin-4-ylmethoxy)benzenesulfonylamino]propanoate In a manner analogous to example 3.6, using 1.5 g (3.7 mmol) of methyl (S)-3-amino-2-[4-(4-fluorobenzyl)piperazin-1-yl]propanoate trihydrochloride and 1.6 g (4.1 mmol) of 4-(2-methylquinolin-4-ylmethoxy)benzenesulfonyl chloride hydrochloride (prepared as described in 17.2), 1.0 g (46%) of methyl (S)-2-[4-(4-fluorobenzyl)piperazin-1-yl]-3-[4-(2-methylquinolin-4-ylmethoxy)benzenesulfonylamino]propanoate is obtained in the form of a white solid.

18.5: (S)-2-[4-(4-fluorobenzyl)piperazin-1-yl]-3-[4-(2-methylquinolin-4-ylmethoxy)benzenesulfonylamino]propanoic Acid In a manner analogous to example 3.7, using 1.1 g (1.7 mmol) of methyl (S)-2-[4-(4-fluorobenzyl)piperazin-1-yl]-3-[4-(2-methylquinolin-4-ylmethoxy)benzenesulfonylamino]propanoate, 1.0 g (100%) of (S)-2-[4-(4-fluorobenzyl)piperazin-1-yl]-3-[4-(2-methylquinolin-4-ylmethoxy)benzenesulfonylamino]propanoic acid are obtained in the form of a white solid.

18.6: (S)-2-[4-(4-Fluorobenzyl)piperazin-1-yl]-N-hydroxy-3-[4-(2-methylquinolin-4-ylmethoxy)benzenesulfonylamino]propionamide In a manner analogous to example 3.8, using 990 mg (1.7 mmol) of (S)-2-[4-(4-fluorobenzyl)-piperazin-1-yl]-3-[4-(2-methylquinolin-4-ylmethoxy)benzenesulfonylamino]propanoic acid, 330 mg (33%) of (S)-2-[4-(4-fluorobenzyl)piperazin-1-yl]-N-hydroxy-3-[4-(2-methylquinolin-4-ylmethoxy)benzenesulfonylamino]propionamide are obtained in the form of a white solid with a melting point of 180° C.
$^1$H NMR (δ, DMSO): 2.20-2.30 (m, 4H); 2.35-2.45 (m, 4H); 2.66 (s, 3H); 2.72-2.80 (m, 1H); 2.87-3.00 (m, 2H); 3.38 (s, 2H); 5.70 (s, 2H); 7.10 (t, J=8.8 Hz, 2H); 7.26-7.33 (m, 4H); 7.56-7.60 (m, 2H); 7.73-7.78 (m, 3H); 7.97 (d, J=8.4 Hz, 1H); 8.10 (d, J=8.2 Hz, 1H).

Example 19

(S)-2-(4-ethyl-piperazin-1-yl)-N-hydroxy-3-[4-(2-methylquinolin-4-yl-methoxy)benzenesulfonylamino]propionamide

19.1: bis(2-Chloroethyl)ethylamine 24 ml (330 mmol) of thionyl chloride are added dropwise to a solution of 20 g (150 mmol) of 2-[ethyl(2-hydroxyethyl)amino]ethanol in 200 ml of dichloromethane cooled beforehand to 0° C., and then the reaction medium is stirred at ambient temperature for 20 h. After the addition of a saturated aqueous solution of sodium hydrogen carbonate, the product is extracted with dichloromethane. The organic phase obtained is then washed with water, dried over magnesium sulfate, filtered and concentrated under vacuum. 19.5 g (76%) of bis(2-chloroethyl)ethylamine are obtained in the form of an oil.

19.2: Methyl (S)-3-tert-butoxycarbonylamino-2-(4-ethylpiperazin-1-yl)propanoate A solution of 5.0 g (19.6 mmol) of commercial methyl (S)-2-amino-3-tert-butoxycarbonylaminopropanoate hydrochloride and 3.3 g (19.6 mmol) of bis(2-chloroethyl)ethylamine in 50 ml of N,N-diisopropylethylamine is heated at 127° C. for 5 h. After evaporation of a maximum amount of diisopropylethylamine, the reaction medium is diluted with ethyl acetate and washed with an aqueous solution of sodium hydroxide having a concentration of 1N. The organic phase obtained is then washed with water, dried over magnesium sulfate, filtered and concentrated under vacuum. The crude product obtained is purified by chromatography on silica gel, elution being carried out with a 30/70 heptane/ethyl acetate mixture. 2.5 g (40%) of methyl (S)-3-tert-butoxycarbonylamino-2-(4-ethylpiperazin-1-yl)propanoate are obtained in the form of an oil.

19.3: Methyl (S)-3-amino-2-(4-ethylpiperazin-1-yl) propanoate Trihydrochloride 2.5 g (7.9 mmol) of methyl (S)-3-tert-butoxycarbonylamino-2-(4-ethylpiperazin-1-yl)propanoate are placed in 20 ml of methanol and 10 ml of isopropanolic hydrochloric acid having a concentration of 5-6N. The reaction medium is heated at 40° C. for 3 h and then evaporated to dryness. The residue is taken up in 50 ml of ethanol, stirred for 1 h at ambient temperature and then filtered. 1.4 g (54%) of methyl (S)-3-amino-2-(4-ethylpiperazin-1-yl)propanoate trihydrochloride are obtained in the form of a beige solid.

19.4: Methyl (S)-2-(4-ethylpiperazin-1-yl)-3-[4-(2-methylquinolin-4-ylmethoxy)benzenesulfonylamino] propanoate In a manner analogous to example 3.6, using 700 mg (2.1 mmol) of methyl (S)-3-amino-2-(4-ethylpiperazin-1-yl)propanoate trihydrochloride and 900 mg (2.3 mmol) of 4-(2-methylquinolin-4-ylmethoxy)benzenesulfonyl chloride hydrochloride (prepared as described in 17.2), 740 mg (67%) of methyl (S)-2-(4-ethylpiperazin-1-yl)-3-[4-(2-methylquinolin-4-ylmethoxy)benzenesulfonylamino]propanoate are obtained in the form of a white solid.

19.5: (S)-2-(4-Ethylpiperazin-1-yl)-3-[4-(2-methylquinolin-4-ylmethoxy)benzenesulfonylamino]propanoic Acid In a manner analogous to example 3.7, using 740 mg (1.4 mmol) of methyl (S)-2-(4-ethylpiperazin-1-yl)-3-[4-(2-methylquinolin-4-ylmethoxy)benzenesulfonylamino]propanoate, 630 mg (87%) of (S)-2-(4-ethylpiperazin-1-yl)-3-[4-(2-methylquinolin-4-ylmethoxy)benzenesulfonylamino] propanoic acid are obtained in the form of a white solid.

19.6: (S)-2-(4-Ethylpiperazin-1-yl)-N-hydroxy-3-[4-(2-methylquinolin-4-ylmethoxy)benzenesulfonylamino]propionamide In a manner analogous to example 3.8, using 630 mg (1.2 mmol) of (S)-2-(4-ethylpiperazin-1-yl)-3-[4-(2-methylquinolin-4-ylmethoxy)benzenesulfonylamino]propanoic acid, 60 mg (8%) of (S)-2-(4-ethylpiperazin-1-yl)-N-hydroxy-3-[4-(2-methylquinolin-4-ylmethoxy)benzenesulfonylamino]propionamide are obtained in the form of a white solid with a melting point of 150° C.

$^1$H NMR (δ, DMSO): 2.49 (s, 3H); 2.55-2.65 (m, 2H); 2.69 (s, 3H); 2.70-2.90 (m, 6H); 2.90-3.00 (m, 2H); 3.13 (t, J=7.3 Hz, 1H); 3.20-3.35 (m, 2H); 3.36 (s, 2H); 5.72 (s, 2H); 7.35 (d, J=8.9 Hz, 2H); 7.58-7.62 (m, 3H); 7.74-7.81 (m, 3H); 7.98 (d, J=7.9 Hz, 1H); 8.12 (d, J=8.3 Hz, 1H); 9.03 (s, 1H), 10.82 (s, 1H).

Example 20

(S)-N-Hydroxy-3-[4-(2-methylquinolin-4-ylmethoxy)benzenesulfonylamino]-2-[4-(4-trifluoromethylbenzyl)piperazin-1-yl]propionamide

20.1: bis-(2-Chloroethyl)(4-trifluoromethylbenzyl)amine

In a manner analogous to example 32.3, using 5.0 g (28 mmol) of bis(2-chloroethyl)amine hydrochloride and 7.4 g (31 mmol) of 1-bromomethyl-4-trifluoromethylbenzene, 5 g (59%) of a bis(2-chloroethyl)(4-trifluoromethylbenzyl) amine mixture are obtained in the form of a colorless oil.

20.2: Methyl (S)-3-tert-butoxycarbonylamino-2-[4-(4-trifluoromethylbenzyl)piperazin-1-yl]propanoate A solution of 4.2 g (16.5 mmol) of methyl (S)-2-amino-3-tert-butoxycarbonylaminopropanoate hydrochloride and 4.95 g (16.5 mmol) of bis(2-chloroethyl)(4-trifluoromethylbenzyl)amine in 25 ml of N,N-diisopropylethylamine is heated at 127° C. for 6 h. After evaporation of a maximum amount of diisopropylethylamine, the reaction medium is diluted with ethyl acetate and washed with an aqueous solution of sodium hydroxide having a concentration of 1N. The organic phase obtained is washed with water, dried over magnesium sulfate, filtered and concentrated under vacuum. The crude residue is purified by chromatography on silica gel, elution being carried out with a 60/40 heptane/ethyl acetate mixture. 4.0 g (55%) of methyl (S)-3-tert-butoxycarbonylamino-2-[4-(4-trifluoromethylbenzyl)piperazin-1-yl]propanoate are obtained in the form of an oil.

20.3: Methyl (S)-3-amino-2-[4-(4-trifluoromethylbenzyl)piperazin-1-yl]propanoate Trihydrochloride In a manner analogous to example 17.5, using 4 g (9.1 mmol) of methyl (S)-3-tert-butoxycarbonylamino-2-[4-(4-trifluoromethylbenzyl)piperazin-1-yl]propanoate, 3.8 g (93%) of methyl (S)-3-amino-2-[4-(4-trifluoromethylbenzyl)piperazin-1-yl]propanoate are obtained in the form of a beige solid.

20.4: Methyl (S)-3-[4-(2-methylquinolin-4-ylmethoxy)benzenesulfonylamino]-2-[4-(4-trifluoromethylbenzyl)piperazin-1-yl]propanoate In a manner analogous to example 3.6, using 1.0 g (2.2 mmol) of methyl (S)-3-amino-2-[4-(4-trifluoromethylbenzyl)piperazin-1-yl]propanoate trihydrochloride and 1.2 g (3.1 mmol) of 4-(2-methylquinolin-4-ylmethoxy)benzenesulfonyl chloride hydrochloride (prepared as described in example 17.2), 910 mg (65%) of methyl (S)-3-[4-(2-methylquinolin-4-ylmethoxy)benzenesulfonylamino]-2-[4-(4-trifluoromethylbenzyl)piperazin-1-yl]propanoate are obtained in the form of a white solid.

20.5: (S)-3-[4-(2-Methylquinolin-4-ylmethoxy)benzenesulfonylamino]-2-[4-(4-trifluoromethylbenzyl) piperazin-1-yl]propanoic Acid In a manner analogous to example 3.7, using 910 mg (1.4 mmol) of methyl (S)-3-[4-(2-methylquinolin-4-ylmethoxy) benzenesulfonylamino]-2-[4-(4-trifluoromethylbenzyl)piperazin-1-yl]-propanoate, 790 mg (88%) of (S)-3-[4-(2-methylquinolin-4-ylmethoxy)benzenesulfonylamino]-2-[4-(4- trifluoromethylbenzyl)-piperazin-1-yl]propanoic acid are obtained in the form of a white solid.

20.6: S)—N-Hydroxy-3-[4-(2-methylquinolin-4-ylmethoxy)benzenesulfonylamino]-2-[4-(4-trifluoromethylbenzyl)piperazin-1-yl]propionamide In a manner analogous to example 3.8, using 790 mg (1.2 mmol) of (S)-3-[4-(2-methylquinolin-4-ylmethoxy)benzenesulfonylamino]-2-[4-(4-trifluoromethylbenzyl)piperazin-1-yl]propanoic acid, 550 mg (68%) of (S)-N-hydroxy-3-[4-(2-methylquinolin-4-ylmethoxy)benzenesulfonylamino]-2-[4-(4-trifluoro-methylbenzyl)piperazin-1-yl]propionamide are obtained in the form of a white solid with a melting point of 148° C.

$^1$H NMR (δ, DMSO): 2.21 (m, 4H); 2.38 (m, 4H); 2.58 (s, 3H); 2.69-2.75 (m, 1H); 2.85-2.93 (m, 1H); 2.93-2.98 (m, 1H); 3.42 (s, 2H); 5.63 (s, 2H); 7.25 (d, J=9 Hz, 2H); 7.40 (d, J=8 Hz, 3H); 7.47-7.53 (m, 2H); 7.57 (d, J=8.1 Hz, 2H); 7.65-7.72 (m, 3H); 7.90 (d, J=7.9 Hz, 1H); 8.03 (d, J=7.8 Hz, 1H); 8.83 (s, 1H), 10.56 (s, 1H).

Example 21

(S)-N-hydroxy-2-[4-(4-methylbenzyl)piperazin-1-yl]-3-[4-(2-methylquinolin-4-ylmethoxy)benzenesulfonylamino]propionamide

21.1: bis(2-Chloroethyl)(4-methylbenzyl)amine

In a manner analogous to example 17.3, using 5.0 g (28 mmol) of bis(2-chloroethyl)amine hydrochloride and 5.7 g (31 mmol) of 1-bromomethyl-4-methylbenzene, 4.9 g (71%) of bis(2-chloroethyl)(4-methylbenzyl)amine are obtained.

21.2: Methyl (S)-3-tert-butoxycarbonylamino-2-[4-(4-methylbenzyl)piperazin-1-yl]propanoate In a manner analogous to example 17.4, using 5.1 g (20 mmol) of commercial methyl (S)-2-amino-3-tert-butoxycarbonylaminopropanoate hydrochloride and 4.9 g (20 mmol) of bis(2-chloroethyl)(4-methylbenzyl)amine, 4.1 g (53%) of methyl (S)-3-tert-butoxycarbonylamino-2-[4-(4-methylbenzyl)piperazin-1-yl]propanoate are obtained in the form of an oil.

21.3: Methyl (S)-3-amino-2-[4-(4-methylbenzyl)piperazin-1-yl]propanoate trihydrochloride In a manner analogous to example 19.3, using 4.1 g (10.5 mmol) of methyl (S)-3-tert-butoxycarbonylamino-2-[4-(4-methylbenzyl)piperazin-1-yl]propanoate, 3.95 g (94%) of methyl (S)-3-amino-2-[4-(4-methylbenzyl)piperazin-1-yl]propanoate trihydrochloride are obtained in the form of a cream solid.

21.4: Methyl (S)-3-[4-(2-methylquinolin-4-ylmethoxy)benzenesulfonylamino]-2-[4-(4-methylbenzyl)piperazin-1-yl]propanoate In a manner analogous to example 3.6, using 1.0 g (2.5 mmol) of methyl (S)-3-amino-2-[4-(4-methylbenzyl)piperazin-1-yl]propanoate trihydrochloride and 1.3 g (3.5 mmol) of 4-(2-methylquinolin-4-ylmethoxy)benzenesulfonyl chloride hydrochloride (prepared as described in example 17.2), 950 mg (63%) of methyl (S)-3-[4-(2-methylquinolin-4-ylmethoxy)benzenesulfonylamino]-2-[4-(4-methylbenzyl)piperazin-1-yl]propanoate are obtained in the form of a white solid.

21.5: (S)-2-[4-(4-Methylbenzyl)piperazin-1-yl]-3-[4-(2-methylquinolin-4-ylmethoxy)benzenesulfonylamino]propanoic Acid In a manner analogous to example 3.7, using 950 mg (1.6 mmol) of methyl (S)-2-[4-(4-methylbenzyl)piperazin-1-yl]-3-[4-(2-methylquinolin-4-ylmethoxy)benzenesulfonylamino]propanoate, 880 mg (95%) of (S)-2-[4-(4-methylbenzyl)piperazin-1-yl]-3-[4-(2-methylquinolin-4-ylmethoxy) benzenesulfonylamino]propanoic acid are obtained in the form of a cream solid.

21.6: (S)—N-Hydroxy-3-[4-(2-methylquinolin-4-ylmethoxy)benzenesulfonylamino]-2-[4-(4-methylbenzyl)piperazin-1-yl]propionamide In a manner analogous to example 3.8, using 880 mg (1.5 mmol) of (S)-3-[4-(2-methylquinolin-4-ylmethoxy)benzenesulfonylamino]-2-[4-(4-methylbenzyl)piperazin-1-yl]propanoic acid, 150 mg (17%) of (S)—N-hydroxy-3-[4-(2-methylquinolin-4-ylmethoxy)benzenesulfonylamino]-2-[4-(4-methylbenzyl)piperazin-1-yl]propionamide are obtained in the form of a white solid with a melting point of 170° C.

$^1$H NMR (δ, DMSO): 2.25 (m, 4H); 2.25 (s, 3H); 2.43 (m, 4H); 2.67 (s, 3H); 2.80 (m, 1H); 2.95-3.05 (m, 2H); 3.37 (m, 2H); 5.71 (s, 2H); 7.10 (q, J=8 Hz, 4H); 7.33 (d, J=8.9 Hz, 2H); 7.43 (m, 1H); 7.56-7.61 (m, 2H); 7.73-7.79 (m, 3H); 7.98 (d, J=8.3 Hz, 1H); 8.11 (d, J=8.2 Hz, 1H); 8.89 (s, 1H); 10.59 (s, 1H).

Example 22

(S)-3-[4-(benzoisoxazol-3-ylmethoxy)benzenesulfonylamino]-N-hydroxy-2-(4-methanesulfonylpiperazin-1-yl)propionamide

22.1: Benzoisoxazol-3-ylmethanol 589 mg (3.0 mmol) of ethyl 1.2-benzoisoxazole-3-carboxylate in solution in 10 ml of tetrahydrofuran are added to a suspension of 129 mg (3.5 mmol) of lithium aluminum hydride in 5 ml of tetrahydrofuran. The reaction mixture is stirred for one hour at 60° C. and then treated by adding 2 ml of methanol dropwise, filtered through celite and rinsed with ethyl acetate. The organic phases are combined, dried over sodium sulfate and evaporated. The residue obtained is purified by chromatography on silica gel, elution being carried out with a 60/40 heptane/ethyl acetate mixture. 180 mg (39%) of benzoisoxazol-3-ylmethanol are obtained in the form of a white solid.

22.2: Methyl (S)-3-[4-(benzoisoxazol-3-ylmethoxy)benzenesulfonylamino]-2-(4-methanesulfonylpiperazin-1-yl)propanoate In a manner analogous to example 11.1, using 494 mg (1.2 mmol) of methyl (S)-3-(4-hydroxy-benzenesulfonylamino)-2-(4-methanesulfonylpiperazin-1-yl)propanoate (prepared as described in 5.1) and 175 mg (1.2 mmol) of benzoisoxazol-3-ylmethanol, 459 mg (71%) of methyl (S)-3-[4-(benzoisoxazol-3-ylmethoxy)benzenesulfonylamino]-2-(4-methanesulfonylpiperazin-1-yl)propanoate are obtained in the form of an oil.

22.3: (S)-3-[4-(benzoisoxazol-3-ylmethoxy)benzenesulfonylamino]-2-(4-methanesulfonylpiperazin-1-yl)propanoic acid In a manner analogous to example 3.7, using 458 mg (0.8 mmol) of methyl (S)-3-[4-(benzoisoxazol-3-ylmethoxy)benzenesulfonylamino]-2-(4-methanesulfonylpiperazin-1-yl)propanoate, 283 mg (63%) of (S)-3-[4-(benzoisoxazol-3-ylmethoxy)benzenesulfonylamino]-2-(4-methanesulfonylpiperazin-1-yl)propanoic acid are obtained in the form of a white solid.

22.4: (S)-3-[4-(benzoisoxazol-3-ylmethoxy)benzenesulfonylamino]-N-hydroxy-2-(4-methanesulfonylpiperazin-1-yl)propionamide In a manner analogous to example 3.8, using 283 mg (0.5 mmol) of (S)-3-[4-(benzoisoxazol-3-ylmethoxy)benzenesulfonylamino]-2-(4-ethanesulfonylpiperazin-1-yl)propanoic acid, 231 mg (80%) of (S)-3-[4-(benzoisoxazol-3-ylmethoxy)benzenesulfonylamino]-N-hydroxy-2-(4-methanesulfonylpiperazin-1-yl)propionamide are obtained in the form of a beige solid with a melting point of 107° C.
$^1$H NMR (δ, DMSO): 2.53-2.55 (m, 4H); 2.88 (s, 3H); 2.90-2.93 (m, 2H); 3.00-3.10 (m, 4H); 3.13 (t, J=6.9 Hz, 1H); 5.77 (s, 2H); 7.35 (d, J=8.8 Hz, 2H); 7.49 (t, J=7.5 Hz, 1H); 7.57 (m, 1H); 7.75 (t, J=7.4 Hz, 1H); 7.78-7.87 (m, 3H); 8.01 (d, J=8 Hz, 1H); 8.96 (m, 1H); 10.67 (m, 1H).

Example 23

(S)-N-hydroxy-2-(4-isobutyrylpiperazin-1-yl)-3-[4-(2-methylquinolin-4-ylmethoxy)-benzenesulfonylamino]propionamide

23.1: Methyl (S)-3-tert-butoxycarbonylamino-2-piperazin-1-ylpropanoate 2 g (25% by weight) of palladium-on-carbon at 10% are added to a solution of 8 g (21 mmol) of methyl(S)-2-(4-benzylpiperazin-1-yl)-3-tert-butoxycarbonylaminopropanoate (prepared as described in example 17.4) in 120 ml of ethanol, degassed beforehand under a nitrogen stream. The reaction medium is then placed under a hydrogen atmospheric pressure for 24 h and then filtered through celite and thoroughly rinsed with dichloromethane. After concentration under vacuum, 6.1 g (100%) of methyl (S)-3-tert-butoxycarbonylamino-2-piperazin-1-ylpropanoate are obtained.

23.2: Methyl (S)-3-tert-butoxycarbonylamino-2-(4-isobutyrylpiperazin-1-yl)propanoate 1.2 ml (8.3 mmol) of triethylamine and then 0.8 ml (7.6 mmol) of isobutyryl chloride are added to a solution of 2.0 g (6.9 mmol) of methyl (S)-3-tert-butoxycarbonylamino-2-piperazin-1-ylpropanoate in 20 ml of dichloromethane, cooled beforehand to 0° C. After stirring at ambient temperature for 1 h 30, water is added. The reaction medium is extracted with dichloromethane. The organic phase is washed with water, dried over magnesium sulfate, filtered and concentrated under vacuum. The crude residue obtained is purified by chromatography on silica gel, elution being carried out with a 50/50 heptane/ethyl acetate mixture. 2.0 g (81%) of methyl (S)-3-tert-butoxycarbonylamino-2-(4-isobutyrylpiperazin-1-yl)propanoate are obtained in the form of a colorless oil.

23.3: (S)-3-tert-butoxycarbonylamino-2-(4-isobutyrylpiperazin-1-yl)propanoic acid 10 ml (10 mmol) of an aqueous solution of lithium hydroxide having a concentration of 1N are added to a solution of 2.0 g (5.6 mmol) of methyl (S)-3-tert-butoxycarbonylamino-2-(4-isobutyrylpiperazin-1-yl)propanoate in 40 ml of tetrahydrofuran and 8 ml of water, and then the reaction medium is stirred at ambient temperature for 20 h. After the addition of an aqueous solution of acetic acid having a concentration of 1N, the product is extracted with n-butanol. The organic phase is dried over magnesium sulfate, filtered and concentrated under vacuum, 1.5 g (78%) of (S)-3-tert-butoxycarbonylamino-2-(4-isobutyrylpiperazin-1-yl)propanoic acid are obtained in the form of a white solid.

23.4: tert-Butyl [(S)-2-allyloxycarbamoyl-2-(4-isobutyrylpiperazin-1-yl)ethyl]carbamate 1.4 g (4.4 mmol) of 0-(benzotriazol-1-yl)-N,N,N',N'-tetramethyluroniumtetrafluoroborate and then 2.3 ml (13.1 mmol) of diisopropylethylamine are added to a solution of 1.5 g (4.4 mmol) of (S)-3-tert-butoxycarbonylamino-2-(4-isobutyrylpiperazin-1-yl)propanoic acid in 20 ml of dimethylformamide. After stirring at ambient temperature for 15 min, a solution of 500 mg (4.6 mmol) of O-allylhydroxylamine hydrochloride and of 0.8 ml (4.6 mmol) of diisopropylethylamine in 10 ml of dimethylformamide is added. The reaction medium is stirred at ambient temperature for 20 h, hydrolyzed with a saturated aqueous solution of sodium hydrogen carbonate, and then diluted with ethyl acetate. The organic phase is washed with a saturated aqueous solution of sodium chloride, dried over magnesium sulfate, filtered and concentrated under vacuum, 1.45 g (83%) of tert-butyl [(S)-2-allyloxycarbamoyl-2-(4-isobutyrylpiperazin-1-yl)ethyl]carbamate are obtained in the form of a colorless oil.

23.5: (S)-N-allyloxy-3-amino-2-(4-isobutyrylpiperazin-1-yl)propionamide dihydrochloride In a manner analogous to example 19.3, using 1.45 g (3.6 mmol) of tert-butyl [(S)-2-allyloxycarbamoyl-2-(4-isobutyrylpiperazin-1-yl)ethyl]carbamate, 1.4 g (100%) of (S)-N-allyloxy-3-amino-2-(4-isobutyrylpiperazin-1-yl)propionamide dihydrochloride are obtained in the form of a white solid.

23.6: (S)-N-allyloxy-2-(4-isobutyrylpiperazin-1-yl)-3-[4-(2-methylquinolin-4-ylmethoxy)benzenesulfonylamino]propionamide 1.9 g (5.1 mmol) of 4-(2-methylquinolin-4-ylmethoxy)benzenesulfonyl chloride hydrochloride (prepared as described in 32.2) are added to a solution of 1.3 g (3.6 mmol) of (S)—N-allyloxy-3-amino-2-(4-isobutyrylpiperazin-1-yl)propionamide dihydrochloride, 2.0 ml (14.5 mmol) of triethylamine in 15 ml of dichloromethane and 15 ml of dimethylformamide, cooled beforehand to 0° C. The reaction medium is then stirred at from 0° C. to ambient temperature over the course of 3 h. After the addition of water, the reaction medium is extracted with dichloromethane. The organic phase is washed with a saturated aqueous solution of sodium hydrogen carbonate and with water, dried over magnesium sulfate, filtered and concentrated.
The crude residue obtained is purified by silica column chromatography, elution being carried out with a 97/3 dichloromethane/methanol mixture. 900 mg (41%) of (S)—N-allyloxy-2-(4-isobutyrylpiperazin-1-yl)-3-[4-(2-methylquinolin-4-ylmethoxy)benzenesulfonylamino]propionamide are obtained in the form of a white solid.

23.7: (S)-N-hydroxy-2-(4-isobutyrylpiperazin-1-yl)-3-[4-(2-methylquinolin-4-ylmethoxy)-benzenesulfonylamino]propionamide 33 mg (0.06 mmol) of tetrakis(triphenylphosphine)palladium and then 920 mg (6.6 mmol) of potassium carbamate are added to a solution of 670 mg (1.1 mmol) of (S)—N-allyloxy-2-(4-isobutyrylpiperazin-1-yl)-3-[4-(2-methylquinolin-4-ylmethoxy)benzenesulfonylamino]propionamide in 15 ml of methanol and then the reaction medium is refluxed for 8 h. After the addition of ethyl acetate, the reaction medium is washed with a saturated aqueous solution of sodium hydrogen carbonate. The organic phase is then washed with water, dried over magnesium sulfate. filtered and concentrated. The crude product is taken up in 6 ml of ethanol and 12 ml of water and then heated at 80° C. until solubilization occurs. After cooling, crystallization is initiated by evaporation of a minimum amount of ethanol. 120 mg of product are obtained by filtration and are purified by preparative thin layer chromatography on silica, elution being carried out with a 97/3 dichloromethane/methanol mixture.

20 mg (3%) of (S)—N-hydroxy-2-(4-isobutyrylpiperazin-1-yl)-3-[4-(2-methylquinolin-4-yl-methoxy)benzenesulfonylamino]propionamide are finally obtained in the form of a beige solid.

$^1$H NMR (δ, DMSO): 0.84 (s, 3H); 0.85 (s, 3H); 2.30-2.44 (m, 2H); 2.52 (m, 2H); 2.67 (s, 3H); 2.77 (m, 1H); 2.85 (m, 2H); 2.95 (m, 1H); 3.35 (m, 4H); 5.71 (s, 2H); 7.33 (d, J=8.9 Hz, 2H); 7.43 (m, 1H); 7.55-7.62 (m, 2H); 7.72-7.82 (m, 3H); 7.98 (d, J=8.4 Hz, 1H); 8.11 (d, J=8.2 Hz, 1H); 8.96 (m, 1H); 10.67 (m, 1H).

Example 24

(S)-N-hydroxy-2-[4-(2-methylpropane-1-sulfonyl)piperazin-1-1]-3-[4-(2-methylquinolin-4-ylmethoxy)benzenesulfonylamino]propionamide

24.1: Methyl (S)-3-tert-butoxycarbonylamino-2-[4-(2-methylpropane-1-sulfonyl)piperazin-1-yl]propanoate 479 mg (3.0 mmol) of 2-methylpropane-1-sulfonyl chloride are added to a solution of 800 mg (2.8 mmol) of methyl (S)-3-tert-butoxycarbonylamino-2-piperazin-1-ylpropanoate (prepared as described in example 23.1) and 775 µl (5.5 mmol) of triethylamine in 8 ml of dichloromethane, cooled beforehand to 0° C. The reaction medium is stirred at ambient temperature for 18 h and then water is added and the medium is extracted with dichloromethane. The organic phase is washed with water, dried over magnesium sulfate, filtered and concentrated. The residue obtained is purified by chromatography on silica gel, elution being carried out with a 5/5 heptane/ethyl acetate mixture. 785 mg (71%) of methyl (S)-3-tert-butoxycarbonylamino-2-[4-(2-methylpropane-1-sulfonyl)piperazin-1-yl]propanoate are obtained in the form of a colorless oil.

24.2: Methyl (S)-3-amino-2-[4-(2-methylpropane-1-sulfonyl)piperazin-1-yl]propanoate Dihydrochloride In a manner analogous to example 3.3, using 785 mg (1.9 mmol) of methyl (S)-3-tert-butoxycarbonylamino-2-[4-(2-methylpropane-1-sulfonyl)piperazin-1-yl]propanoate, 621 mg (85%) of methyl (S)-3-amino-2-[4-(2-methylpropane-1-sulfonyl)piperazin-1-yl]propanoate dihydrochloride are obtained in the form of a solid.

24.3: Methyl (S)-2-[4-(2-methylpropane-1-sulfonyl)piperazin-1-yl]-3-[4-(2-methylquinolin-4-ylmethoxy)benzenesulfonylamino]propanoate In a manner analogous to example 3.6, using 621 mg (1.6 mmol) of methyl (S)-3-amino-2-[4-(2-methylpropane-1-sulfonyl)piperazin-1-yl]propanoate dihydrochloride and 876 mg (2.3 mmol) of 4-(2-methylquinolin-4-ylmethoxy)benzenesulfonyl chloride hydrochloride (prepared as described in example 17.2), 643 mg (64%) of methyl (S)-2-[4-(2-methylpropane-1-sulfonyl)piperazin-1-yl]-3-[4-(2-methylquinolin-4-ylmethoxy)benzenesulfonylamino]propanoate are obtained in the form of an oil.

24.4: (S)-2-[4-(2-methylpropane-1-sulfonyl)piperazin-1-yl]-3-[4-(2-methylquinolin-4-ylmethoxy)benzenesulfonylamino]propanoic Acid In a manner analogous to example 3.7, using 643 mg (1.0 mmol) of methyl (S)-2-[4-(2-methylpropane-1-sulfonyl)piperazin-1-yl]-3-[4-(2-methylquinolin-4-ylmethoxy)benzenesulfonylamino]propanoate, 395 mg (63%) of (S)-2-[4-(2-methylpropane-1-sulfonyl)piperazin-1-yl]-3-[4-(2-methylquinolin-4-ylmethoxy)benzenesulfonylamino]propanoic acid are obtained in the form of a white solid.

24.5: (S)-N-hydroxy-2-[4-(2-methylpropane-1-sulfonyl)piperazin-1-yl]-3-[4-(2-methylquinolin-4-ylmethoxy)benzenesulfonylamino]propionamide In a manner analogous to example 3.8, using 390 mg (0.6 mmol) of (S)-2-[4-(2-methylpropane-1-sulfonyl)piperazin-1-yl]-3-[4-(2-methylquinolin-4-ylmethoxy)benzenesulfonylamino]propanoic acid, 12 mg (3%) of (S)—N-hydroxy-2-[4-(2-methylpropane-1-sulfonyl)piperazin-1-yl]-3-[4-(2-methylquinolin-4-ylmethoxy)benzenesulfonylamino]propionamide are obtained in the form of a white solid.

$^1$H NMR (δ, DMSO): 1.01 (d, J=6.7 Hz, 6H); 2.05 (m, 1H); 2.49 (m, 4H); 2.67 (s, 3H); 2.86 (d, J=6.6 Hz, 2H); 3.00-3.10 (m, 6H); 3.31 (m, 1H); 5.71 (s, 2H); 7.34 (d, J=8.9 Hz, 2H); 7.52 (m, 1H); 7.57 (m, 2H); 7.76-7.80 (m, 3H); 7.98 (d, J=8.2 Hz, 1H); 8.10 (m, 1H); 8.93 (s, 1H); 10.66 (s, 1H).

Example 25

(S)-N-hydroxy-2-(4-methanesulfonylpiperazin-1-yl)-3-[4-(2-trifluoromethyl-pyrazolo[1,5-α]pyridin-3-ylmethoxy)benzenesulfonylamino]propionamide

25.1: Ethyl 2-trifluoromethylpyrazolo[1,5-α]pyridine-3-carboxylate

A solution of 2.1 g (38 mmol) of KOH in 20 ml of water and then 6.7 g (30 mmol) of 1-aminopyridinium iodide are added to a solution of 2.5 g (15 mmol) of ethyl 4,4,4-trifluorobut-2-ynoate in 25 ml of dichloromethane. After stirring at ambient temperature for 5 h, water is added and the reaction medium is extracted with dichloromethane. The organic phase is washed with water, dried over magnesium sulfate. filtered and concentrated. The residue obtained is purified by chromatography on silica gel, elution being carried out with an 8/2 heptane/ethyl acetate mixture. 2.8 g (73%) of ethyl 2-trifluoromethylpyrazolo[1,5-α]pyridine-3-carboxylate are obtained in the form of a yellow solid.

25.2: (2-trifluoromethylpyrazolo[1,5-α]pyridin-3-yl) methanol

A solution of 2.8 g (11 mmol) of ethyl 2-trifluoromethylpyrazolo[1,5-α]pyridine-3-carboxylate in 50 ml of tetrahydrofuran is added dropwise to a suspension of 0.5 g (12 mmol) of lithium aluminum hydride in 45 ml of tetrahydrofuran. The reaction medium is then stirred at 70° C. for 3 h. After dropwise addition of 2.5 ml of methanol and then of 1.8 ml of an aqueous solution of sodium hydroxide having a concentration of 2N, the reaction medium is stirred for 20 min at ambient temperature and then filtered. The filtrate is dried over magnesium sulfate, filtered and concentrated under vacuum. 2.3 g (100%) of (2-trifluoromethylpyrazolo[1,5-α]pyridin-3-yl)methanol are obtained in the form of a solid.

25.3: Methyl (S)-2-(4-methanesulfonylpiperazin-1-yl)-3-[4-(2-trifluoromethylpyrazolo[1,5-α]pyridin-3-ylmethoxy)benzenesulfonylamino]propanoate In a manner analogous to example 11.1, using 800 mg (1.9 mmol) of methyl (S)-3-(4-hydroxybenzenesulfonylamino)-2-(4-methanesulfonylpiperazin-1-yl)propanoate (prepared as described in 5.1) and 540 mg (2.5 mmol) of (2-trifluoromethylpyrazolo[1,5-α]pyridin-3-yl)methanol, 380 mg (32%) of methyl (S)-2-(4-methanesulfonylpiperazin-1-yl)-3-[4-(2-trifluoromethylpyrazolo[1,5-α]pyridin-3-ylmethoxy)benzenesulfonylamino]propanoate are obtained in the form of a white solid.

25.4: (S)-2-(4-methanesulfonylpiperazin-1-yl)-3-[4-(2-trifluoromethylpyrazolo[1,5-α]pyridin-3-ylmethoxy)benzenesulfonylamino]propanoic Acid In a manner analogous to example 3.7, using 380 mg (0.6 mmol) of methyl (S)-2-(4-methanesulfonylpiperazin-1-yl)-3-[4-(2-trifluoromethylpyrazolo[1,5-α]pyridin-3-ylmethoxy)benzenesulfonylamino]propanoate, 237 mg (64%) of (S)-2-(4-methanesulfonylpiperazin-1-yl)-3-[4-(2-trifluoromethylpyrazolo[1,5-α]pyridin-3-ylmethoxy)benzenesulfonylamino]propanoic acid are obtained in the form of a white solid.

25.5: (S)—N-hydroxy-2-(4-methanesulfonylpiperazin-1-yl)-3-[4-(2-trifluoromethylpyrazolo[1,5-α]pyridin-3-ylmethoxy)benzenesulfonylamino]propionamide In a manner analogous to example 3.8, using 230 mg (0.4 mmol) of (S)-2-(4-methanesulfonyl-piperazin-1-yl)-3-[4-(2-trifluoromethylpyrazolo[1,5-α]pyridin-3-ylmethoxy)benzenesulfonylamino]propanoic acid, 9 mg (4%) of (S)—N-hydroxy-2-(4-methanesulfonylpiperazin-1-yl)-3-[4-(2-trifluoromethylpyrazolo[1,5-α]pyridin-3-ylmethoxy) benzenesulfonylamino]propionamide are obtained in the form of a white solid.

¹H NMR (α, DMSO): 2.51-2.54 (m, 4H); 2.84 (s, 3H); 2.95 (m, 1H); 2.97-3.04 (m, 4H); 3.10 (m, 1H); 3.32 (m, 1H); 5.45 (s, 2H); 7.20-7.25 (m, 3H); 7.49-7.51 (m, 2H); 7.76 (d, J=8.8 Hz, 2H); 8.04 (m, 1H); 8.87 (d, J=7 Hz, 2H); 8.90 (m, 1H).

Example 26

(S)-N-hydroxy-3-[4-(2-methylquinolin-4-ylmethoxy) benzenesulfonylamino]-2-[4-(propane-2-sulfonyl) piperazin-1-yl]propionamide

26.1: Methyl (S)-3-tert-butoxycarbonylamino-2-[4-(propane-2-sulfonyl)piperazin-1-yl]propanoate In a manner analogous to example 20.2, using 800 mg (2.8 mmol) of methyl (S)-3-tert-butoxycarbonylamino-2-piperazin-1-ylpropanoate (prepared as described in example 23.1) and 342 µl (3.1 mmol) of propane-2-sulfonyl chloride, 700 mg (64%) of methyl (S)-3-tert-butoxycarbonylamino-2-[4-(propane-2-sulfonyl)piperazin-1-yl]propanoate are obtained in the form of an oil.

26.2: Methyl (S)-3-amino-2-[4-(propane-2-sulfonyl) piperazin-1-yl]propanoate Dihydrochloride In a manner analogous to example 3.3, using 700 mg (1.8 mmol) of methyl (S)-3-tert-butoxycarbonylamino-2-[4-(propane-2-sulfonyl)piperazin-1-yl]propanoate, 620 mg (86%) of methyl (S)-3-amino-2-[4-(propane-2-sulfonyl)piperazin-1-yl]propanoate dihydrochloride are obtained in the form of an oil.

26.3: Methyl (S)-3-[4-(2-methylquinolin-4-ylmethoxy)benzenesulfonylamino]-2-[4-(propane-2-sulfonyl)piperazin-1-yl]propanoate In a manner analogous to example 17.6, using 620 mg (1.5 mmol) of methyl (S)-3-amino-2-[4-(propane-2-sulfonyl)piperazin-1-yl]propanoate dihydrochloride and 830 mg (2.1 mmol) of 4-(2-methylquinolin-4-ylmethoxy)benzenesulfonyl chloride hydrochloride (prepared as described in the example 17.2), 505 mg (54%) of methyl (S)-3-[4-(2-methylquinolin-4-ylmethoxy)benzenesulfonylamino]-2-[4-(propane-2-sulfonyl)piperazin-1-yl]propanoate are obtained in the form of a white solid.

26.4: (S)-3-[4-(2-methylquinolin-4-ylmethoxy)benzenesulfonylamino]-2-[4-(propane-2-sulfonyl)piperazin-1-yl]propanoic Acid In a manner analogous to example 3.7, using 505 mg (0.8 mmol) of methyl (S)-3-[4-(2-methylquinolin-4-ylmethoxy) benzenesulfonylamino]-2-[4-(propane-2-sulfonyl)piperazin-1-yl]propanoate, 135 mg (27%) of (S)-3-[4-(2-methylquinolin-4-ylmethoxy)benzenesulfonylamino]-2-[4-(propane-2-sulfonyl)piperazin-1-yl]propanoic acid are obtained in the form of a white solid.

26.5: (S)—N-hydroxy-3-[4-(2-methylquinolin-4-ylmethoxy)benzenesulfonylamino]-2-[4-(propane-2-sulfonyl)piperazin-1-yl]propionamide In a manner analogous to example 3.8, using 135 mg (0.2 mmol) of (S)-3-[4-(2-methylquinolin-4-ylmethoxy)benzenesulfonylamino]-2-[4-(propane-2-sulfonyl)piperazin-1-yl] propanoic acid, 24 mg (17%) of (S)-N-hydroxy-3-[4-(2-methylquinolin-4-ylmethoxy)benzenesulfonylamino]-2-[4-(propane-2-sulfonyl)piperazin-1-yl]propionamide are obtained in the form of a white solid.

¹H NMR (δ, DMSO): 1.19 (d, J=6.8 Hz, 6H); 2.45 (m, 4H); 2.68 (s, 3H); 2.80-2.90 (m, 1H); 2.95-3.15 (m, 6H); 3.29 (m, 1H); 5.72 (s, 2H); 7.34 (d, J=8.9 Hz, 2H); 7.52 (m, 1H); 7.57 (m, 2H); 7.76-7.80 (m, 3H); 7.98 (d, J=8.2 Hz, 1H); 8.10 (d, J=8.1 Hz, 1H); 8.93 (s, 1H); 10.66 (s, 1H).

Example 27

(S)-2-(4-benzylpiperazin-1-yl)-N-hydroxy-3-[4-(2-trifluoromethylpyrazolo[1,5-α]pyridin-3-ylmethoxy)benzenesulfonylamino]propionamide 27.1: 4-Hydroxybenzenesulfonyl Chloride A solution of 7 g (30 mmol) of the sodium salt of 4-hydroxybenzenesulfonic acid dihydrate in 40 ml of dimethylformamide is added dropwise to a solution of 15.5 ml (181 mmol) of oxalyl chloride in 120 ml of dichloromethane cooled to −30° C. The reaction medium is slowly brought back to ambient temperature and then stirred at ambient temperature for 18 h. After the addition of 200 ml of ice, the reaction medium is extracted with ethyl acetate. The organic phase is washed with water and with a saturated aqueous solution of sodium chloride, dried over magnesium sulfate, filtered and concentrated. 6.2 g (100%) of 4-hydroxybenzenesulfonyl chloride are obtained in the form of a colorless oil.

27.2: Methyl (S)-2-(4-benzylpiperazin-1-yl)-3-(4-hydroxybenzenesulfonylamino)propanoate In a manner analogous to example 3.6, using 5.8 g (30 mmol) of 4-hydroxybenzenesulfonyl chloride and 7.7 g (20 mmol) of methyl (S)-3-amino-2-(4-benzylpiperazin-1-yl)propanoate trihydrochloride (prepared as described in example 17.5), 2.25 g (27%) of methyl (S)-2-(4-benzylpiperazin-1-yl)-3-(4-hydroxybenzenesulfonylamino)propanoate are obtained in the form of a white solid.

27.3: Methyl (S)-2-(4-benzylpiperazin-1-yl)-3-[4-(2-trifluoromethylpyrazolo[1,5-α]pyridin-3-ylmethoxy)benzenesulfonylamino]propanoate In a manner analogous to example 11.1, using 500 mg (1.1 mmol) of methyl (S)-2-(4-benzylpiperazin-1-yl)-3-(4-hydroxybenzenesulfonylamino)propanoate and 370 mg (1.7 mmol) of (2-trifluoromethylpyrazolo[1,5-α]pyridin-3-yl)methanol (prepared as described in example 25.2), 350 mg (50%) of methyl (S)-2-(4-benzylpiperazin-1-yl)-3-[4-(2-trifluoromethylpyrazolo[1,5-α]pyridin-3-ylmethoxy)benzenesulfonylamino]propanoate are obtained in the form of a colorless oil.

27.4: (S)-2-(4-benzylpiperazin-1-yl)-3-[4-(2-trifluoromethylpyrazolo[1,5-α]pyridin-3-ylmeth-oxy)benzenesulfonylamino]propanoic acid In a manner analogous to example 3.7, using 350 mg (0.5 mmol) of methyl (S)-2-(4-benzylpiperazin-1-yl)-3-[4-(2-trifluoromethylpyrazolo[1,5-α]pyridin-3-ylmethoxy)benzenesulfonylamino]propanoate, 165 mg (48%) of (S)-2-(4-benzylpiperazin-1-yl)-3-[4-(2-trifluoromethylpyrazolo[1,5-α]pyridin-3-ylmethoxy)benzenesulfonylamino]propanoic acid are obtained in the form of a white solid.

27.5: (S)-2-(4-benzylpiperazin-1-yl)-N-hydroxy-3-[4-(2-trifluoromethylpyrazolo[1,5-α]pyridin-3-ylmethoxy)benzenesulfonylamino]propionamide In a manner analogous to example 3.8, using 165 mg (0.3 mmol) of (S)-2-(4-benzylpiperazin-1-yl)-3-[4-(2-trifluoromethylpyrazolo[1,5-α]pyridin-3-ylmethoxy)benzenesulfonylamino]propanoic acid, 50 mg (29%) of (S)-2-(4-benzylpiperazin-1-yl)-N-hydroxy-3-[4-(2-trifluoromethylpyrazolo[1,5-α]pyridin-3-ylmethoxy)benzenesulfonylamino]propionamide are obtained in the form of a white solid with a melting point of 138° C.

¹H NMR (δ, DMSO): 2.20 (m, 4H); 2.38 (m, 4H); 2.65-2.75 (m, 1H); 2.86-2.98 (m, 2H); 3.35 (m, 2H); 5.37 (s, 2H); 7.10-7.25 (m, 8H); 7.35-7.44 (m, 2H); 7.68 (d, J=8.9 Hz, 2H); 7.98 (d, J=9 Hz, 1H); 8.81 (m, 2H); 10.52 (s, 1H).

Example 28

Enzymatic Assay for TACE Inhibition

Description of the Assay

The products are solubilized in DMSO at a concentration of 10 mM. A serial 3-fold dilution over 10 points is carried out so as to have a concentration range of from 10 µM to 0.5 nM final concentration.

The TACE enzyme is an internal production (carried out according to the publication "protein Eng Des Sel 2006, 19, 155-161") and is added so as to have a signal equivalent to 6 times the background noise in 2 h at 37° C. The reaction is carried out in 50 mM Tris buffered medium containing 4% glycerol, pH 7.4. The fluorescent substrate is MCA-Pro-Leu-Ala-Val-(Dpa)-Arg-Ser-Ser-Arg-NH$_2$ (R&D systems, reference: ES003). The substrate is cleaved by the enzyme between the alanine and the valine, thus releasing a fluorescent peptide (excitation: 320 nm, emission: 420 nm). The substrate is used at 40 µM. The reaction is carried out in a final volume of 10 µl (4 µl inhibitor, 4 µl substrate, 2 µl enzyme) in a low volume 384-well plate (Corning reference: 3676). The plate is incubated at ambient temperature for 2 h, and then read by fluorescence on a Pherastar reader (BMG labtech). The IC$_{50}$ is determined using mathematical processing software (XLfit).

Product Assay

| Example No. | % TACE inhibition at 10 µM | IC50 - TACE (nM) |
| --- | --- | --- |
| ex1 | 100 | 87 |
| ex2 | 100 | 32 |
| ex4 | 95 | 497 |
| ex5 | 99 | 21 |
| ex6 | 99 | 52 |
| ex8 | 100 | 127 |
| ex9 | 100 | 147 |
| ex10 | 93 | 47 |
| ex11 | 93 | 24 |
| ex13 | 96 | 108 |
| ex14 | 98 | 64 |
| ex16 | 96 | 168 |
| ex17 | 91 | 62 |
| ex18 | 90 | 67 |
| ex19 | 92 | 41 |
| ex21 | 97 | 63 |
| ex23 | 97 | 53 |
| ex24 | 98 | 86 |
| ex26 | 98 | 33 |

On the basis of the results obtained in the TACE enzymatic assay described above, the compounds claimed in the present invention are TNF-alpha converting enzyme (TACE) inhibitors and consequently may be potential active ingredients for the treatment of pathological conditions for which reducing TNF-alpha production would be of great interest.

Example 29

Selectivity Assay

Principle of the Assay:

The molecules are dose-response tested on the following enzymes: MMP1, MMP3, MMP9, ADAM9 and ADAM10, according to the same protocol as that described for the TACE enzyme in example 28, but with different substrates (MMP R&D systems, reference: P126-990, and ADAM R&D systems, reference: ES003).

The enzymes are purchased from Calbiochem.

Product Assay:

| | IC50 (nM) | | | | | |
|---|---|---|---|---|---|---|
| Example | MMP1 | MMP3 | MMP9 | ADAM9 | ADAM10 | TACE |
| 5 | 5100 | 3200 | >10000 | >10000 | >10000 | 21 |
| 18 | 670 | 849 | >10000 | 9254 | >10000 | 67 |
| 19 | 2303 | 1770 | >10000 | 3054 | >10000 | 41 |
| 20 | 3935 | 4775 | >10000 | >10000 | >10000 | 140 |
| 21 | 1166 | 887 | >10000 | >10000 | >10000 | 63 |
| 23 | 2221 | 1065 | >10000 | >10000 | >10000 | 53 |
| 24 | 2059 | 1878 | >10000 | >10000 | >10000 | 16 |
| 26 | 969 | 574 | >10000 | >10000 | >10000 | 16 |
| Apratastat | 145 | 10 | 82 | 85 | 71 | 5 |

On the basis of the results obtained in the selectivity assay described above, these compounds are also very selective for TACE compared with the other ADAMs and MMPs, i.e. they have $IC_{50}$ values for other ADAMs or MMPs that are at least 10 times higher than that obtained for TACE, and more advantageously at least 100 times higher. As it happens, insofar as it is known that the nonselective inhibition of these families of enzymes induces adverse side effects observed in vivo, the selective inhibition of TACE compared with these other enzymes should make it possible to reduce adverse side effects when these molecules are administered for the treatment of pathological conditions for which reducing TNF-alpha production would be of great interest.

The invention claimed is:

1. A compound of formula (I), a salt thereof, or an enantiomer thereof,

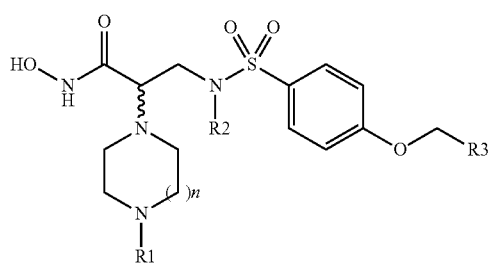

(I)

in which:
R$_1$ represents a hydrogen, an alkyl radical, a substituted alkyl radical, an alkenyl radical, a substituted alkenyl radical, an alkynyl radical, a substituted alkynyl radical, an aralkyl radical, a substituted aralkyl radical, a heteroaralkyl radical, a substituted heteroaralkyl radical, a —C(O)—R$_4$ radical, a —SO$_2$—R$_4$ radical, or a C(O) OR$_4$ radical, with R$_4$ having the meanings given hereinafter;

R$_2$ is a hydrogen atom or a lower alkyl radical;

R$_3$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, a substituted aralkyl radical, a heterocyclic radical, a substituted heterocyclic radical, a cycloalkyl radical, a substituted cycloalkyl radical, a heteroaryl radical, a substituted heteroaryl radical, a heteroaralkyl radical, or a substituted heteroaralkyl radical;

R$_4$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, or a substituted aralkyl radical; and, n is 1.

2. The compound as claimed in claim 1, a salt thereof, or an enantiomer thereof, wherein R$_1$ represents a hydrogen, an alkyl radical, a substituted alkyl radical, an alkenyl radical, a substituted alkenyl radical, an alkynyl radical, a substituted alkynyl radical, an aralkyl radical, a substituted aralkyl radical, a heteroaralkyl radical, a substituted heteroaralkyl radical, a —C(O)—R$_4$ radical, a —SO$_2$—R$_4$ radical, or a C(O) OR$_4$ radical, with R$_4$ having the meanings given hereinafter;

R$_2$ is a hydrogen atom or a lower alkyl radical;

R$_3$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical, or a substituted heteroaralkyl radical;

R$_4$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, or a substituted aralkyl radical; and, n is 1.

3. The compound as claimed in claim 1, a salt thereof, or an enantiomer thereof, wherein R$_1$ represents a hydrogen, an alkyl radical, a substituted alkyl radical, an alkenyl radical, a substituted alkenyl radical, an alkynyl radical, a substituted alkynyl radical, an aralkyl radical, a substituted aralkyl radical, a —C(O)—R$_4$ radical, or a —SO$_2$—R$_4$ radical, with R$_4$ having the meanings given hereinafter;

R$_2$ is a hydrogen atom or a lower alkyl radical;

R$_3$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;

R$_4$ is an alkyl radical, a substituted alkyl radical, an aryl radical, a substituted aryl radical, an aralkyl radical, or a substituted aralkyl radical; and, n is 1.

4. The compound as claimed in claim 1, a salt thereof, or an enantiomer thereof, wherein R$_1$ represents an alkyl radical, a substituted alkyl radical, an aralkyl radical, a substituted aralkyl radical, a —C(O)—R$_4$ radical, or a —SO$_2$—R$_4$ radical, with R$_4$ having the meanings given hereinafter;

R$_2$ is a hydrogen atom;

R$_3$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical, or a substituted heteroaralkyl radical;

R₄ is an alkyl radical, a substituted alkyl radical, an aryl radical, a substituted aryl radical, an aralkyl radical, or a substituted aralkyl radical; and, n is 1.

5. The compound as claimed in claim 1, a salt thereof, or an enantiomer thereof, wherein R₁ represents an alkyl radical, a substituted alkyl radical, an aralkyl radical, a substituted aralkyl radical, a —C(O)—R₄ radical, or a —SO₂—R₄ radical, with R₄ having the meanings given hereinafter;

R₂ is a hydrogen atom;

R₃ is a heterocyclic radical, a substituted heterocyclic radical, a heteroaryl radical, a substituted heteroaryl radical, a heteroaralkyl radical, or a substituted heteroaralkyl radical;

R₄ is an alkyl radical, a substituted alkyl radical, an aryl radical, a substituted aryl radical, an aralkyl radical or a substituted aralkyl radical; and, n is 1.

6. The compound as claimed in claim 1, a salt thereof, or an enantiomer thereof, wherein R₁ represents an alkyl radical, a substituted alkyl radical, an aralkyl radical, a substituted aralkyl radical, a —C(O)—R₄ radical, or a —SO₂—R₄ radical, with R₄ having the meanings given hereinafter;

R₂ is a hydrogen atom;

R₃ is a heteroaryl radical or a substituted heteroaryl radical;

R₄ is an alkyl radical, a substituted alkyl radical, an aryl radical, a substituted aryl radical, an aralkyl radical, or a substituted aralkyl radical; and, n is 1.

7. The compound as claimed in claim 1, a salt thereof, or an enantiomer thereof, wherein the compound is selected from the group consisting of:

1) 3-[(4-but-2-ynyloxybenzenesulfonyl)methylamino]-N-hydroxy-2-(4-methanesulfonylpiperazin-1-yl)propionamide;
2) (S)-3-(4-but-2-ynyloxybenzenesulfonylamino)-N-hydroxy-2-(4-methanesulfonylpiperazin-1-yl)propionamide;
3) (S)-3-(4-benzyloxybenzenesulfonylamino)-N-hydroxy-2-(4-methanesulfonylpiperazin-1-yl)propionamide;
4) (S)-3-[(4-benzyloxybenzenesulfonyl)methylamino]-N-hydroxy-2-(4-methanesulfonylpiperazin-1-yl)propionamide;
5) (S)—N-hydroxy-2-(4-methanesulfonylpiperazin-1-yl)-3-[4-(2-methylquinolin-4-ylmethoxy)benzenesulfonylamino]propionamide;
6) (S)—N-hydroxy-2-(4-methanesulfonylpiperazin-1-yl)-3-[4-(naphthalen-1-ylmethoxy)benzenesulfonylamino]propionamide;
7) (S)—N-hydroxy-2-(4-methanesulfonylpiperazin-1-yl)-3-(4-propoxybenzenesulfonylamino)propionamide;
8) (S)-3-[4-(3-cyanobenzyloxy)benzenesulfonylamino]-N-hydroxy-2-(4-methanesulfonylpiperazin-1-yl)propionamide;
9) (S)-3-[4-(4-cyanobenzyloxy)benzenesulfonylamino]-N-hydroxy-2-(4-methanesulfonylpiperazin-1-yl)propionamide;
10) benzyl 4-{(S)-1-hydroxycarbamoyl-2-[4-(2-methylquinolin-4-ylmethoxy)benzenesulfonylamino]ethyl}piperazine-1-carboxylate;
11) (S)—N-hydroxy-2-(4-methanesulfonylpiperazin-1-yl)-3-[4-(2-phenylpyridin-4-ylmethoxy)benzenesulfonylamino]propionamide;
12) (R)—N-hydroxy-2-(4-methanesulfonylpiperazin-1-yl)-3-[4-(2-methylquinolin-4-ylmethoxy)benzenesulfonylamino]propionamide;
13) (S)—N-hydroxy-3-[4-(2-methylquinolin-4-ylmethoxy)benzenesulfonylamino]-2-piperazin-1-ylpropionamide;
14) (S)—N-hydroxy-2-(4-methanesulfonylpiperazin-1-yl)-3-[4-(2-methylquinolin-4-ylmethoxy)benzenesulfonylamino]propionamide hydrochloride;
15) tert-butyl 3-{4-[(S)-2-hydroxycarbamoyl-2-(4-methanesulfonylpiperazin-1-yl)ethylsulfamoyl]phenoxymethyl}-2-methylindole-1-carboxylate di(trifluoroacetate);
16) (S)—N-hydroxy-2-(4-methanesulfonylpiperazin-1-yl)-3-[4-(quinolin-4-ylmethoxy)benzenesulfonylamino]propionamide;
17) (S)-2-(4-benzylpiperazin-1-yl)-N-hydroxy-3-[4-(2-methylquinolin-4-ylmethoxy)benzenesulfonylamino]propionamide;
18) (S)-2-[4-(4-fluorobenzyl)piperazin-1-yl]-N-hydroxy-3-[4-(2-methylquinolin-4-ylmethoxy)benzenesulfonylamino]propionamide;
19) (S)-2-(4-ethylpiperazin-1-yl)-N-hydroxy-3-[4-(2-methylquinolin-4-ylmethoxy)benzenesulfonylamino]propionamide;
20) (S)—N-hydroxy-3-[4-(2-methylquinolin-4-ylmethoxy)benzenesulfonylamino]-2-[4-(4-trifluoromethyl-benzyl)piperazin-1-yl]propionamide;
21) (S)—N-hydroxy-2-[4-(4-methylbenzyl)piperazin-1-yl]-3-[4-(2-methylquinolin-4-ylmethoxy)benzenesulfonylamino]propionamide;
22) (S)-3-[4-(benzoisoxazol-3-ylmethoxy)benzenesulfonylamino]-N-hydroxy-2-(4-methanesulfonylpiperazin-1-yl)propionamide;
23) (S)—N-hydroxy-2-(4-isobutyrylpiperazin-1-yl)-3-[4-(2-methylquinolin-4-ylmethoxy)benzenesulfonylamino]propionamide;
24) (S)—N-hydroxy-2-[4-(2-methylpropane-1-sulfonyl)piperazin-1-yl]-3-[4-(2-methylquinolin-4-ylmethoxy)benzenesulfonylamino]propionamide;
25) (S)—N-hydroxy-2-(4-methanesulfonylpiperazin-1-yl)-3-[4-(2-trifluoromethylpyrazolo[1,5-a]pyridin-3-ylmethoxy)benzenesulfonylamino]propionamide;
26) (S)—N-hydroxy-3-[4-(2-methylquinolin-4-ylmethoxy)benzenesulfonylamino]-2-[4-(propane-2-sulfonyl)piperazin-1-yl]propionamide;
27) (S)-2-(4-benzylpiperazin-1-yl)-N-hydroxy-3-[4-(2-trifluoromethylpyrazolo[1,5-a]pyridin-3-ylmethoxy)benzenesulfonylamino]propionamide;
28) (S)-2-(4-acetylpiperazin-1-yl)-N-hydroxy-3-[4-(2-methylquinolin-4-ylmethoxy)benzenesulfonylamino]propionamide;
29) (S)—N-hydroxy-2-(4-methanesulfonylpiperazin-1-yl)-3-{propyl-[4-(quinolin-4-ylmethoxy)benzenesulfonyl]amino}propionamide;
30) (S)-2-(4-benzenesulfonylpiperazin-1-yl)-N-hydroxy-3-[4-(pyrazolo[1,5-a]pyridin-3-ylmethoxy)benzenesulfonylamino]propionamide;
31) (S)-2-(4-benzylpiperazin-1-yl)-N-hydroxy-3-[4-(1-methylpiperidin-4-ylmethoxy)benzenesulfonylamino]propionamide;
32) (S)-2-[4-(4-fluorobenzoyl)piperazin-1-yl]-N-hydroxy-3-[4-(3-m-tolyl-propoxy)benzenesulfonylamino]propionamide;
33) (S)—N-hydroxy-3-[4-(2-methylnaphthalen-1-ylmethoxy)benzenesulfonylamino]-2-(4-propionylpiperazin-1-yl)propionamide;

34) (S)—N-hydroxy-3-[4-(4-methylpentyloxy)benzenesulfonylamino]-2-(4-phenylacetylpiperazin-1-yl)propionamide;

35) (S)—N-hydroxy-2-(4-methanesulfonylpiperazin-1-yl)-3-[4-(2-methylpyridin-4-ylmethoxy)benzenesulfonylamino]propionamide;

36) (S)—N-hydroxy-3-[4-(2-methylbenzofuran-3-ylmethoxy)benzenesulfonylamino]-2-[4-(propane-2-sulfonyl)piperazin-1-yl]propionamide; and 37)(S)-2-(4-benzylpiperazin-1-yl)-N-hydroxy-3-[4-(2-isopropyl-1H-indol-3-ylmethoxy)benzenesulfonylamino]propionamide.

8. A compound as claimed in claim 1 or a salt thereof, wherein the compound is (S)—N-hydroxy-3-[4-(2-methylquinolin-4-ylmethoxy)benzenesulfonylamino]-2-[4-(propane-2-sulfonyl)piperazin-1-yl]propionamide.

9. A composition comprising the compound as claimed in claim 1, a salt thereof, or an enantiomer thereof, and a carrier.

10. A pharmaceutical composition comprising the compound as claimed in claim 1, a salt thereof, or an enantiomer thereof, and a pharmaceutically acceptable carrier.

11. A method of treating a disease, wherein the method comprises administering the pharmaceutical composition as claimed in claim 10, to a subject in need thereof, wherein the disease is selected from the group consisting of an inflammatory bowel disease (IBD), an inflammatory bone disease, transplant rejection, an autoimmune disease, osteoarthritis, rheumatoid arthritis, ankylosing spondylitis, juvenile chronic arthritis, multiple sclerosis, non-insulin-dependent diabetes mellitus, an allergic disease, asthma, chronic obstructive pulmonary disease (COPD), inflammatory skin disease, and ocular inflammation.

12. The method as claimed in claim 1, wherein the inflammatory skin disease is psoriasis, atopic dermatitis, or psoriatic arthritis.

13. The method as claimed in claim 1, wherein the inflammatory bowel disease (IBD) is Crohn's disease or ulcerative colitis.

14. A method of inhibiting the activity of TACE (TNFα-converting enzyme), wherein the method comprises contacting a TACE with the pharmaceutical composition as claimed in claim 10.

15. The method of claim 14, wherein the TACE is in a subject.

16. A method of inhibiting the production of TNFα, wherein the method comprises contacting a cell producing TNFα with the pharmaceutical composition as claimed in claim 10.

17. The method of claim 16, wherein the cell is in a subject.

* * * * *